United States Patent
Thomson et al.

(10) Patent No.: US 11,739,341 B2
(45) Date of Patent: Aug. 29, 2023

(54) FRUIT-SPECIFIC PROMOTERS

(71) Applicant: The United States of America, as represented by the Secretary of Agriculture, Washington, DC (US)

(72) Inventors: James G. Thomson, El Cerrito, CA (US); Roger L. Thilmony, El Cerrito, CA (US); Kasturi Dasgupta, Fremont, CA (US); Christopher D. Dardick, Shenandoah Junction, WV (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 17/366,517

(22) Filed: Jul. 2, 2021

(65) Prior Publication Data
US 2022/0042027 A1    Feb. 10, 2022

Related U.S. Application Data

(62) Division of application No. 16/421,348, filed on May 23, 2019, now Pat. No. 11,091,768.

(60) Provisional application No. 62/675,637, filed on May 23, 2018.

(51) Int. Cl.
*C12N 15/82*    (2006.01)

(52) U.S. Cl.
CPC ....... *C12N 15/8235* (2013.01); *C12N 15/825* (2013.01)

(58) Field of Classification Search
None
See application file for complete search history.

(56) References Cited

U.S. PATENT DOCUMENTS 5,608,150 A * 3/1997 Conner .............. C12N 15/8235
536/23.6

OTHER PUBLICATIONS

Kim et al. A 20 nucleotide upstream element is essential for the nopaline synthase (nos) promoter activity. Plant Molecular Biology, 1994, vol. 24, pp. 105-117. (Year: 1994).*

* cited by examiner

*Primary Examiner* — Cynthia E Collins
(74) *Attorney, Agent, or Firm* — John D. Fado; Maria Restrepo-Hartwig

(57) ABSTRACT

The present disclosure provides genetic constructs containing a promotor that is useful in driving fruit-specific expression in plants. Further provided are expression vectors, transgenic plants, and plant parts containing such genetic constructs, as well as uses thereof.

12 Claims, 38 Drawing Sheets
Specification includes a Sequence Listing.

CitSEPp

CitWAXp

CitUNKp

CitJuSacp

PfeMybAp

FRUIT-SPECIFIC PROMOTERS

CROSS-REFERENCE TO RELATED APPLICATIONS

This application claims the benefit of U.S. Provisional Application No. 62/675,637, filed May 23, 2018, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: SequenceListing, date recorded: Jun. 28, 2021, size: 19 KB).

FIELD OF THE DISCLOSURE

The present disclosure relates generally to the field of plant breeding and biotechnology. More specifically, it relates to fruit-specific promoters and uses thereof.

BACKGROUND

Fruits are an important source of nutrients, minerals, vitamins, and dietary fiber, and as such, significant efforts have been made to breed for fruits with higher yield and better quality. Traditional methods of fruit breeding have been hampered by a number of challenges, including large size of the plant, long juvenile phase, and limited genetic gains. Recently, advances in genomics and genetic engineering have been used to genetically improve fruit crops by affording new sources of characteristics and shortened breeding cycles. Genetic engineering of fruit crops involves directly manipulating the genome of a fruit species, typically by introducing into the genome a genetic construct carrying exogenous genetic information, e.g., a foreign gene. Once successfully integrated into the host genome, the exogenous genetic information may express and result in a favorable change in the physiological and morphological properties of the organism, leading to an improvement of the desired trait.

To express exogenous genetic information in the host organism, the genetic construct needs to contain certain regulatory sequences, such as a promoter. During the various stages of the growth and development of the plant, and as to the various parts and organs of the plant, it is often desirable to direct the effect of the genetic construct to a particular plant part and/or to a particular growth stage, such that the exogenous genetic information is expressed with minimum adverse side effects on normal plant growth and development. Accordingly, it would be advantageous for the promoter of a genetic construct to be able to direct transgene expression in the appropriate cell types (tissue-specific expression) and/or at the appropriate time in development (development-specific expression). Therefore, promoters that are capable of driving fruit-specific expression would be valuable genetic tools for engineering fruit traits of agronomic importance, such as growth, ripening, nutritional quality, and post-harvest shelf life.

To date, a number of fruit-specific promoters have been isolated and characterized from various plant species, mostly from tomato. For instance, the tomato E4 and E8 promoters have been found to be fruit-specific that are coordinately regulated by ethylene during fruit ripening (Deikman, et al. (1992) Plant Physiol. 100:2013-2017; Xu et al. (1996) Plant Mol. Biol. 31: 1117-1127). Additional tomato fruit-specific promoters include the promoter of the polygalacturonase gene (PG), which plays a role in cell wall degradation during fruit ripening (Bird et al. (1988) Plant Mol. Biol. 11:651-662; Lau et al (2009) Plant Mol. Biol. Rep. 27:250-256); the promoter of the T-proline-rich protein F1 (TPRP-F1) gene, which is specifically expressed in the ovary and young fruit (Salts et al. (1992) Plant Mol. Biol. 18:407-409); and the promoter of ACC synthase (Lin et al. (2007) Chin. Sci. Bull. 52:1217-1222). A few fruit-specific promoters have also been isolated from non-tomato plant species, such as the promoter of the ripening-upregulated gene ACC-oxidase in apple and peach, the promoter of PG from apple, and the promoter of expansin from sour cherry (Atkinson et al. (1998) Plant Mol. Biol. 38:449-460; Rasori et al. (2003) Plant Sci. 165:523-530). However, in many fruit species the availability of frit-specific promoters suitable for use in genetic engineering is still limited.

Global demand for fruit products is continuously on the rise. Thus, a need exists for the identification of novel promoters providing robust and reliable fruit-specific expression and for their use in the engineering of fruit crops towards improved agronomic traits and nutritional quality.

SUMMARY

In order to meet the above and other needs, the present disclosure provides genetic constructs containing a promoter driving fruit-specific expression in plants. The present disclosure also provides expression vectors, transgenic plants and plant parts containing the genetic constructs described herein. Further provided are methods of using the disclosed genetic constructs in fruit breeding.

Accordingly, one aspect of the present disclosure relates to a genetic construct containing a promoter operably linked to a heterologous nucleotide sequence encoding a product of interest, where the promoter comprises a sequence selected from SEQ ID NOs: 1-5, or a sequence having at least 90% identity thereto. In some embodiments, the product of interest is an RNA molecule. In some embodiments, the product of interest is a polypeptide. In some embodiments, the product of interest is in an anthocyanin metabolic pathway, in a tocopherol metabolic pathway, in a fatty acid metabolic pathway, in a carotenoid metabolic pathway, in a lycopene metabolic pathway, in a betalain metabolic pathway, and/or in a flavonoid metabolic pathway. In some embodiments, the product of interest is a MYB transcription factor, a phytoene synthase (PSY), a lycopene cyclase (LCY), or a DXP synthase (DXS).

Another aspect of the present disclosure relates to expression vectors, transgenic plants and plant parts containing a genetic construct of any of the preceding embodiments. In some embodiments, the present disclosure relates to an expression vector having a genetic construct of any of the preceding embodiments. In some embodiments, the present disclosure relates to a transgenic plant having a genetic construct of any of the preceding embodiments. In some embodiments, the present disclosure relates to a plant part of the transgenic plant, where the plant part contains a genetic construct of any of the preceding embodiments. In some embodiments, the plant part is a stem, a branch, a root, a leaf, a flower, a fruit, a seed, a cutting, a bud, a cell, or a portion thereof.

Yet another aspect of the present disclosure includes a method of modifying a fruit phenotype in a plant, the method having the steps of: i) transforming a plant cell with a genetic construct of any of the preceding embodiments, where expression of the product of interest is associated with modification of the fruit phenotype; ii) regenerating a plant from the transformed plant cell; and iii) growing the regenerated plant to produce fruit of the modified phenotype. In some embodiments, the fruit phenotype is selected from size, weight, color, shape, firmness, glossiness, flavor, aroma, secondary metabolite content, peel thickness, seed number, juice quality, juice sugar content, juice acid content, juice taste, juice color, and juice yield. In some embodiments, the fruit phenotype is selected from anthocyanin content, tocopherol content, fatty acid content, carotenoid content, lycopene content, betalain content, and flavonoid content.

In some embodiments that may be combined with any of the preceding embodiments, the plant is selected from orange (*Citrus sinensis*), mandarin (*Citrus reticulata*), lime (*Citrus aurantifolia*), grapefruit (*Citrus paradisi*), lemon (*Citrus limon*), pomelo (*Citrus maxima*), citron (*Citrus medica*), papeda (*Citrus micrantha*), and *Prunus* sp.

The present disclosure is based, at least in part, on the unexpected discovery that tomato plants expressing a genetic construct described herein, where the genetic construct comprises a promoter sequence of SEQ ID NO: 4 or a sequence having at least 90% identity thereto, produce seedless fruit. Accordingly, another aspect of the present disclosure provides a method of creating a tomato plant with seedless fruit, the method having the steps of 1) transforming a tomato plant cell with a genetic construct described herein, where the promoter comprises the sequence of SEQ ID NO: 4, or a sequence having at least 90% identity thereto; ii) regenerating a tomato plant from the transformed tomato plant cell; and iii) growing the regenerated tomato plant to produce seedless fruit.

It is to be understood that one, some, or all of the properties of the various embodiments described above and herein may be combined to form other embodiments of the present disclosure. These and other aspects of the present disclosure will become apparent to one of skill in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows the various sequence elements identified in the candidate fruit-specific promoter CitSEPp. FIG. 3B shows the various sequence elements identified in the candidate fruit-specific promoter CitWAXp. FIG. 3C shows the various sequence elements identified in the candidate fruit-specific promoter CitUNKp. FIG. 3D shows the various sequence elements identified in the candidate fruit-specific promoter CitJuSacp. FIG. 3E shows the various sequence elements identified in the candidate fruit-specific promoter PfeMybAp.

FIG. 9A shows the quantitative GUS analysis on leaf (L) in representative transgenic tomato lines transformed with the Promoter:: GUS constructs as compared to wild type. FIG. 9B shows the quantitative GUS analysis on unripe fruit (UR) in representative transgenic tomato lines transformed with the Promoter::GUS constructs as compared to wild type. FIG. 9C shows the quantitative GUS analysis on ripe fruit (R) in representative transgenic tomato lines transformed with the Promoter::GUS constructs as compared to wild type. FIG. 9D shows the quantitative GUS analysis on leaf (L), unripe fruit (UR) and ripe fruit (R) in representative transgenic tomato lines transformed with the CitSEPp::GUS construct as compared to wild type.

FIG. 15A shows the results of RT-PCR for transgenic citrus plants transformed with the CitWAXp::MoroMybA construct as compared to wild type. FIG. 15B shows the results of RT-PCR for transgenic citrus plants transformed with the CitUNKp::MoroMybA construct as compared to wild type. FIG. 15C shows the results of RT-PCR for transgenic citrus plants transformed with the CitJuSacp::MoroMybA construct as compared to wild type. FIG. 15D shows the results of RT-PCR for transgenic citrus plants transformed with the PfeMybAp::MoroMybA construct as compared to wild type. FIG. 15E shows the results of RT-PCR for transgenic citrus plants transformed with the E8p::MoroMybA construct as compared to wild type.

DETAILED DESCRIPTION

Figure 1:
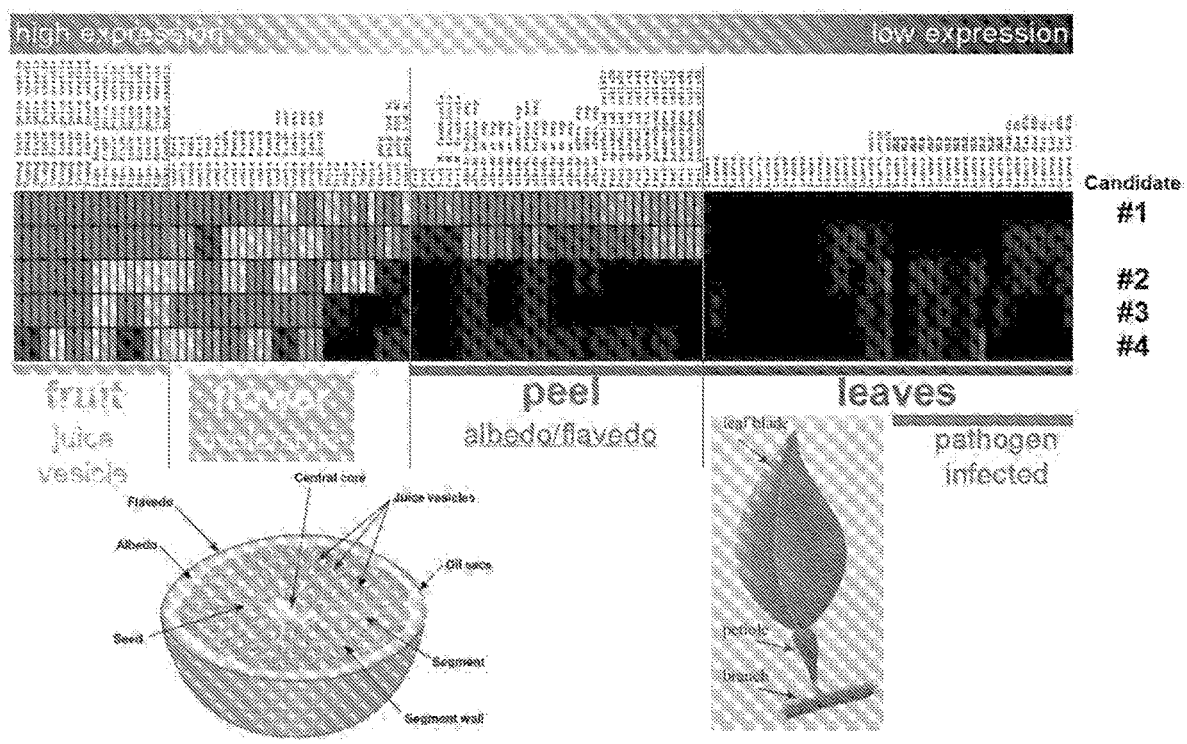
FIG. 1 shows the expression patterns of tissue specificity for the candidate fruit-specific citrus genes #1-#4.

The following description is presented to enable a person of ordinary skill in the art to make and use the various embodiments. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the broadest scope consistent with the claims.

The present disclosure relates generally to genetic constructs containing a promoter allowing for tissue-specific expression in plants. Further embodiments relate generally to expression vectors, transgenic plants and transgenic plant parts containing a genetic construct disclosed herein, as well as methods of use thereof.

Genetic Constructs of the Disclosure

In one aspect, the present disclosure provides a genetic construct containing a promoter operably linked to a heterologous nucleotide sequence encoding a product of interest, where the promoter comprises a sequence selected from SEQ ID NOs: 1-5, or a sequence having at least 90% identity thereto.

As used herein, a "genetic construct" or "construct" refers to an artificially assembled nucleic acid molecule containing one or more genetic elements in a deliberately arranged order. A genetic construct may be generated from any type of nucleic acid, e.g., DNA, RNA or variants thereof. For instance, a genetic construct that is artificially assembled from DNA is referred to as a "DNA construct". A genetic construct may also contain any type of genetic element, including but not limited to, an enhancer, a silencer, a promoter, a 5' untranslated region (5' UTR), an open reading frame (ORF), an exon, an intron, a protein-coding region, a functional RNA-coding region, a 3' untranslated region (3' UTR), a terminator, and fragments thereof.

In some embodiments, the genetic construct of the present disclosure is an expression construct. As used herein, an "expression construct" is a genetic construct that contains necessary genetic elements that are positioned in a way capable of conferring transcription and/or translation in a host cell. As used herein, the term "transcription" refers to the synthesis of RNA molecules from DNA templates, and the term "translation" refers to the synthesis of polypeptide molecules from RNA templates. As used herein, the term "expression" or "gene expression" refers to transcription of a DNA template (e.g., gene, genetic construct) into RNA (e.g., mRNA, tRNA, rRNA, non-coding RNA), with or without subsequent translation of the RNA into a polypeptide. Expression may include both transcription and translation, as well as any modification and processing of the products therein.

As used herein, "expression pattern" of a gene or genetic construct relates to its being transcribed at a certain time during plant growth and development (temporal expression pattern), and/or in a certain location in the plant (spatial expression pattern). It may be desirable for a gene or genetic construct to have a particular expression pattern to achieve optimal effect. For example, constitutive expression of a gene product may be beneficial in one location of the plant but less beneficial in another part of the plant; in other cases, it may be beneficial to have a gene product produced at a certain developmental stage of the plant or in response to certain environmental or chemical stimuli. As used herein, the terms "tissue-specific expression", "tissue-preferred expression" and "tissue-preferential expression" are used interchangeably to refer to a pattern of expression that is substantially limited to certain tissue types. Tissue-specific expression is not necessarily limited to expression in a single tissue but may include expression limited to one or more specific tissues, such as the specific tissues within one organ. For example, an expression pattern that is substantially limited to the specific tissues within a fruit is referred to as tissue-specific expression in fruit. As used herein, the terms "tissue-specific expression in fruit" and "fruit-specific expression" are used interchangeably and refer to expression that is substantially limited to fruit of a plant.

Promoters

As used herein, the term "promoter" refers to a nucleotide sequence capable of controlling the expression of a particular nucleotide sequence of interest. A promoter may include one or more promoter elements. As used herein, a "promoter element" or "cis-element" means an element that influences the characteristics and/or activities of the promoter, such as temporal and spatial expression patterns. Examples of a promoter element include, without limitation, TATA box. CAAT box, GC box, and CAP site. Methods of identifying promoter elements are well known in the art. For example, a promoter sequence may be analyzed for known promoter elements using tools such as Plant Promoter Analysis Navigator (PlantPAN, see Chang et al. (2008) BMC Genomics 9(1):561-561), PLAnt Cis-acting regulatory DNA Elements (PLACE, see Higo et al. (1999) Nucleic Acids Research 27(1):297-300), and Plant Cis-acting Regulatory Elements (PlantCARE, see Lescot et al. (2002) Nucleic Acids Research 30(1):325-327).

In one aspect, the present disclosure provides promoters that are capable of directing tissue-specific expression in fruit. In some embodiments, the promoter comprises a nucleotide sequence of SEQ ID NO: 1. In some embodiments, the promoter comprises a nucleotide sequence of SEQ ID NO: 2. In some embodiments, the promoter comprises a nucleotide sequence of SEQ ID NO: 3. In some embodiments, the promoter comprises a nucleotide sequence of SEQ ID NO: 4. In some embodiments, the promoter comprises a nucleotide sequence of SEQ ID NO: 5. As used herein, the terms "fruit-specific", "fruit-preferred", and "fruit-preferential" are used interchangeably to refer to a pattern of expression that is predominantly in fruit of a plant.

Homologs, orthologs, and paralogs of the promoter of the present disclosure may be identified by sequence identify and isolated using methods known in the art. As used herein, the term "sequence identity" refers to the state of having identical residues in the same locations when two or more nucleic acid or amino acid sequences are aligned. In some embodiments, the promoter of the present disclosure comprises a nucleotide sequence having a certain degree of sequence identify to any one of the SEQ ID NOs: 1-5. The term "% identical" or "% identity" as used herein, refers to the percentage or level of nucleotide or amino acid sequence identity between two or more aligned sequences. The determination of percent sequence identity and/or similarity between any two sequences may be accomplished using a mathematical algorithm. Examples of such mathematical algorithms are the algorithm of Myers and Miller. CABIOS 4:11-17 (1988): the local homology algorithm of Smith et al., Adv. Appl. Math. 2:482 (1981); the homology alignment algorithm of Needleman and Wunsch, J. Mol. Biol. 48:443-453 (1970); the search-for-similarity-method of Pearson and Lipman, Proc. Natl. Acad. Sci. 85:2444-2448 (1988); the algorithm of Karlin and Altschul. Proc. Natl. Acad. Sci. USA 87:2264-2268 (1990), modified as in Karlin and Altschul. Proc. Natl. Acad. Sci. USA 90:5873-5877 (1993). Computer implementations of these mathematical algorithms can be utilized for comparison of sequences to determine sequence identity and/or similarity. Such implementations include, for example: CLUSTAL in the PC/Gene program (Intelligenetics. Mountain View, Calif.); the AlignX program, version 10.3.0 (Invitrogen. Carlsbad, Calif.) and GAP. BESTFIT, BLAST, FASTA, and TFASTA in the Wisconsin Genetics Software Package. Version 8 (Genetics Computer Group, Madison, Wis.).

Alignments using these programs can be performed using the default parameters. The CLUSTAL program is well described by Higgins et al. Gene 73:237-244 (1988); Higgins et al. CABIOS 5:151-153 (1989); Corpet et al., Nucleic Acids Res. 16:10881-90 (1988); Huang et al. CABIOS 8:155-65 (1992); and Pearson et al., Meth. Mol. Biol. 24:307-331 (1994). The BLAST programs of Altschul et al. J. Mol. Biol. 215:403-410 (1990) are based on the algorithm of Karlin and Altschul (1990) supra.

Thus, accordingly, in some embodiments, the promoter of the present disclosure comprises a nucleotide sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO: 1. In some embodiments, the promoter of the present disclosure has a nucleotide sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO: 2. In some embodiments, the promoter of the present disclosure has a nucleotide sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO: 3. In some embodiments, the promoter of the present disclosure has a nucleotide sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO: 4. In some embodiments, the promoter of the present disclosure has a nucleotide sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO: 5.

A plant promoter typically comprises a core promoter, and often, additional regulatory elements. The core promoter is the minimal sequence that is required for directing basal level of expression, comprising a TATA box region where RNA polymerase, TATA-binding protein (TBP), and TBP-associated factors may bind to initiate transcription. In addition to the core promoter, further sequence elements are often necessary for initiating transcription that has a tissue- or developmental stage-specific expression pattern. For instance, the TGTCACA motif has been found to be a cis-regulatory enhancer element necessary for fruit-specific expression in melon species (Yamagata et al. (2002) J. Biol. Chem. 277:11582-11590). Accordingly, in some embodiments, the promoter of the present disclosure comprises critical sequences from SEQ ID NOS: 1, 2, 3, 4, or 5 that are necessary for promoting fruit-specific expression.

Heterologous Nucleotide Sequence

In some embodiments, the promoter of the present disclosure is operably linked to a heterologous nucleotide sequence.

In the context of the present disclosure, the term "operably linked" means that one genetic element of a genetic construct is in a functional relationship with another genetic element of the genetic construct. For example, a promoter or enhancer is operably linked to a coding sequence if it affects the transcription of the coding sequence; or a ribosome binding site is operably linked to a coding sequence if it is positioned so as to facilitate translation. In some embodiments, the genetic elements being linked are contiguous. In other embodiments, the operably linked genetic elements are not contiguous, e.g., enhancers may not be contiguous with a coding sequence.

In genetic constructs of the present disclosure, the heterologous nucleotide sequence encodes a product of interest. As used herein, a "heterologous nucleotide sequence" refers to a DNA or RNA sequence that is from a different origin than the nucleotide sequence of the promoter. Thus, a nucleotide sequence that has been isolated from an organism different from that of the promoter is considered a heterologous nucleotide sequence with respect to the promoter, a nucleotide sequence that has been isolated from a gene that is different from that of the promoter is also considered a heterologous nucleotide sequence with respect to the promoter. In some embodiments, the heterologous nucleotide sequence encodes an RNA molecule. In some embodiments, the heterologous nucleotide sequence encodes a polypeptide. The encoding heterologous nucleotide sequence may be any type of nucleotide sequence, including but not limited to, complementary DNA (cDNA), genomic DNA (gDNA), nuclear DNA, organellar DNA, mitochondrial DNA, chloroplast DNA, plastid DNA, plasmid DNA, viral DNA, isolated DNA, purified DNA, and synthetic DNA.

As used herein, the term "product of interest" refers to any biological product resulting from expression of a nucleotide sequence. For example, the product of interest may be a transcriptional product of the heterologous nucleotide sequence of the genetic construct (e.g., mRNA, tRNA, rRNA, antisense RNA, interfering RNA, ribozyme, structural RNA or any other type of RNA), or it may be a polypeptide produced by translation of the mRNA transcribed from the heterologous nucleotide sequence of the genetic construct.

Polypeptide

In certain embodiments, the product of interest encoded by the heterologous nucleotide sequence is a polypeptide. As used herein, the terms "polypeptide" and "protein" are used interchangeably to refer to an amino acid sequence that includes a plurality of consecutive polymerized amino acid residues. The product of interest may include polypeptides as direct products from translation, or it may include polypeptides modified by, for example, methylation, acetylation, phosphorylation, ubiquitination, and glycosylation.

In one embodiment, the product of interest is a MYB transcription factor. The term "MYB transcription factor" or "MYB protein" is well understood by those skilled in the art to refer to a large class of transcription factors characterized by a structurally conserved MYB domain which is a DNA-binding domain that contains single or multiple imperfect repeat sequences. For the purpose of this disclosure, the terms "MYB". "MYB-like" and "MYB-related" are interchangeable. For example, "MYB domain" may be used interchangeably with "MYB-like domain", and "MYB transcription factor" may be used interchangeably with "MYB-related transcription factor" or "MYB-related protein". In plants, MYB transcription factors are involved in various processes of plant growth and development, including regulation of secondary metabolism as well as response to biotic and abiotic stresses. In particular, specific MYB transcription factors have been suggested as a major determinant of anthocyanin activation and accumulation in plants (Du et al., Biochemistry (2009)74:1-11. Dubos et al., Plant J. (2008) 55:940-953).

In another embodiment, the product of interest is a phytoene synthase (PSY). Phytoene synthase is an enzyme involved in the biosynthesis of carotenoids. Carotenoid biosynthesis is initiated by phytoene synthase, which catalyzes a tail-to-tail condensation of geranylgeranyl pyrophosphate (GGPP) to form phytoene, which after successive desaturation reactions is converted into lycopene. Two main types of PSY exist in plants. PSY1 and PSY2; the former being more responsible for carotenoid synthesis in fruit ripening, whereas the latter being predominantly responsible for carotenoid synthesis in chloroplast-containing tissues. Manipulation of PSY expression in many plants has been shown to dramatically enhance formation of carotenoids and their metabolic intermediates, including lycopene (Liu et al. (2004) Proc. Natl. Acad. Sci. 101:9897-9902, Kolotilin et al. (2007) Plant Physiol. 145:389-401, Galpaz et al. (2008) Plant J. 53:717-730).

In yet another embodiment, the product of interest is a lycopene cyclase (LCY). Lycopene cyclase is an enzyme involved in cyclization of lycopene, which is an important branching step in carotenoid biosynthesis. In plants, there are two types of LCY, lycopene β-cyclase (β-LCY) and lycopene ε-cyclase (ε-LCY), both of which are involved in the conversion of lycopene into carotenoids. Because LCY is involved in breaking down of lycopene, reducing expression of LCY has been suggested to increase the accumulation of lycopene. For a more detailed description of LCY, see Cunningham, et al. (1996) Plant Cell 8(9):1613-1626.

In still another embodiment, the product of interest is a DXP synthase (DXS). 1-deoxy-D-xylulose 5-phosphate (DXP) synthase (DXS) is an enzyme that catalyzes the first biosynthetic step of the 2-C-methyl-D-erythritol 4-phosphate (MEP) pathway. In plants, the MEP pathway is involved in the synthesis of the common precursors to the plastidic isoprenoids, isopentenyl diphosphate and dimethylallyl diphosphate, in plastids. DXS is recognized as limiting this pathway and is a potential target for manipulation to increase various isoprenoids such as carotenoids. For a more detailed description of DXS, see Lang et al. (1998) Proc. Natl. Acad. Sci. 95:2100-2104.

In other embodiments, the product of interest of the present disclosure may be a polypeptide useful in genome editing. As used herein, the term "genome editing" or "gene editing" refers to the process of altering the target genomic DNA sequence by inserting, replacing, or removing one or more nucleotides. Genome editing may be accomplished by using nucleases, which create specific double-strand breaks (DSBs) at desired locations in the genome, and harness the cell's endogenous mechanisms to repair the induced break by homology-directed repair (HDR) (e.g., homologous recombination) or by nonhomologous end joining (NHEJ). Any suitable nuclease may be introduced into a cell to induce genome editing of a target DNA sequence including, but not limited to, CRISPR-associated protein (Cas, e.g., Cas9) nucleases, zinc finger nucleases (ZFNs, e.g. FokI), transcription activator-like effector nucleases (TALENs, e.g., TALEs), meganucleases, and variants thereof (Shukla et al. (2009) Nature 459: 437-441; Townsend et al (2009) Nature 459: 442-445). In some embodiments, the product of interest of the present disclosure is Cas9.

RNAs

In certain embodiments, the product of interest encoded by the heterologous nucleotide sequence of the present disclosure is an RNA molecule. The RNA molecule may be a coding RNA, such as messenger RNA (mRNA), transfer RNA (tRNA) and ribosomal RNA (rRNA); alternatively, the RNA molecule may be one that is capable of regulating gene expression, such as a small RNA. The product of interest of the present disclosure may also be an RNA molecule that has been modified, by processes such as capping, polyadenylation, methylation, and editing.

As used herein, the term "small RNA" refers to several classes of non-coding ribonucleic acid (ncRNA). Small RNA molecules usually include about 20 to 30 nucleotides. The small RNA sequences may be derived from longer precursors. The precursors form structures that fold back on each other in self-complementary regions, which are then processed by the nuclease Dicer in animals or DCL1 in plants. Many types of small RNA exist either naturally or produced artificially, including microRNA (miRNA), short interfering RNA (siRNA), antisense RNA, short hairpin RNA (shRNA), and small nucleolar RNA (snoRNA). Small RNA sequences do not directly code for a protein, and differ in function from other RNAs in that small RNA sequences are only transcribed and not translated. Certain types of small RNA, such as microRNA and siRNA, are important in the process RNA interference (RNAi). RNAi is a process of genetic regulation in which a target gene that would otherwise normally express is suppressed from expression due to interference of small RNAs through post-transcriptional degradation or inhibition of translation. For detailed description of RNAi techniques, see, e.g., U.S. Pat. Nos. 5,034,323; 6,326,527; 6,452,067; 6,573,099; 6,753,139; and 6,777,588.

Accordingly, the product of interest of the present disclosure that is an RNA molecule may silence expression of a native DNA sequence within a plant's tissues to achieve a desired phenotype, for example, increased lycopene content in a fruit. In such case, gene silencing may be accomplished, for example, by transforming into a plant the genetic construct disclosed herein containing a fruit-specific promoter operably linked to a heterologous nucleotide sequence, which encodes an siRNA molecule that binds to and cleavages transcripts of lycopene cyclase (LCY), whereby silencing the gene expression thereof. Because LCY is responsible for breaking down lycopene, the resulting transgenic plant with fruit-specific silencing of LCY expression would therefore have increased accumulation of lycopene in the fruit.

In addition, the product of interest of the present disclosure may also be an RNA molecule that is useful in genome editing. Examples of such RNA molecules include, but are not limited to, CRISPR RNA (crRNA), trans-activating crRNA (tracrRNA), guide RNA (gRNA), and single guide RNA (sgRNA). In some embodiments, the product of interest of the present disclosure is a single guide RNA.

Metabolic Pathways

In certain embodiments, the product of interest encoded by the heterologous nucleotide sequence of the present disclosure is involved in a metabolic pathway. The term "metabolic pathway" refers to the series of linked biochemical reactions involved in the synthesis, conversion and breakdown of a compound in an organism. Genetic engineering of metabolic pathways and pathway components is also known as "metabolic engineering". A metabolic pathway can be part of either primary or secondary metabolism.

Primary metabolism refers to the sum of metabolic activities that are common to most, if not all, living cells and are necessary for basal growth and maintenance of the cells. A metabolic pathway in primary metabolism is known as a "primary metabolic pathway". In some embodiments, the product of interest is involved in a primary metabolic pathway. In the context of genetic engineering in fruit crops, modifications in primary metabolic pathways may lead to changes in sugar, protein and lipid content in a plant, for example, fruit with improved flavor and nutrition profile.

Fatty acids are the most abundant form of reduced carbon chains available from nature and have diverse uses ranging from food to industrial feedstocks. In recent years, long chain polyunsaturated omega-3 fatty acids (LC-PUFAs) such as eicosapentaenoic acid (EPA), and docosahexaenoic acid (DHA) have received considerable attention for their health-promoting benefits. However, EPA and DHA are typically sourced from marine fish only. Reconstitution of the omega-3 LC-PUFA biosynthetic pathway in plants by producing transgenic plants engineered to accumulate omega-3 LC-PUFA would be advantageous. Accordingly, in some embodiments, the product of interest of the present disclosure is in a fatty acid metabolic pathway. In some further embodiments, the product of interest of the present disclosure is in the LC-PUFA biosynthetic pathway. Fruit-specific expression of such a product of interest may result in increased levels of omega-3 LC-PUFAs, including EPA and DHA, to levels similar to those found in fish oil in the fruit.

Secondary metabolism refers to the biological pathways that are not absolutely required for the survival of the organism. Compared to primary metabolism which is more conserved throughout a wide variety of taxa, secondary metabolism is more species-specific or organ-specific. Thus, secondary metabolism is also sometimes known as "specialized metabolism". A metabolic pathway in secondary metabolism is referred to as a "secondary metabolic pathway". Compounds such as substrates, intermediates and products of secondary metabolic pathways are accordingly referred to as "secondary metabolites". Many of the secondary metabolites, such as anthocyanins, lycopene, and tocopherols have been shown to be powerful antioxidants that could be incorporated into human diet for potential health benefits. One way of accomplishing this objective is to genetically engineer plants to have proper accumulation of these beneficial secondary metabolites to a level that is health-promoting. Thus, the genetic constructs of the present disclosure may be used to specifically increase the contents of these secondary metabolites in fruit for human consumption.

Accordingly, in some embodiments, the product of interest is involved in a flavonoid metabolic pathway. Flavonoids are among the best-characterized plant secondary metabolites in terms of chemistry, coloration mechanism, biochemistry, genetics and molecular biology. Flavonoids, with a basic structure of C6-C3-C6, are widely distributed among land plants. Flavonoids in plants are mainly classified into six major subgroups: chalcones, flavones, flavonols, flavandiols, anthocyanins, and proanthocyanidins or condensed tannins. Modification of flavonoids with hydroxyl, methyl, glycosyl and acyl groups results in several thousand structures. The flavonoid biosynthetic pathway has been well studied among higher plants. Flavonoids are synthesized in the cytosol. It has been proposed that the biosynthetic enzymes form a super-molecular complex (metabolon) via protein-protein interaction and are anchored in the endoplasmic reticulum (ER) membrane. The biosynthetic enzymes belong to various enzyme families, such as 2-oxo-glutarate-dependent dioxygenases (OGD), cytochromes P450 (P450) and glucosyltransferases (GT), which suggests that plants recruited these enzymes from pre-existing metabolic pathways. Accordingly, the product of interest of the present disclosure may be an enzyme in the flavonoid metabolic pathway or a regulator thereof. Examples of such product of interest may include, without limitation, glucosyltransferases (GT), acyltransferases (AT) and methyltransferases (MT), CHS, chalcone synthase; THC2'GT, UDP-glucose:tetrahydroxychalcone 2'GT; CHI, chalcone isomerase; THC4'GT, UDP-glucose:tetrahydroxychalcone 4'GT; AS, aureusidin synthase; F3H, flavanone 3-hydroxylase; F3'H, flavonoid 3'-hydroxylase; F3'5'H, flavonoid 3',5'-hydroxylase; DFR, dihydroflavonol 4-reductase; ANS, anthocyanidin synthase; FNS, flavone synthase; FLS, flavonol synthase, and R2R3 Myb transcriptional factor, basic helix-loop-helix (bHLH) transcriptional factor, and WD40-type transcriptional factor. For a more detailed description of the flavonoid metabolic pathway, see Winkel-Shirley (2001) Plant Physiol. 126(2):485-493.

In some embodiments, the product of interest is involved in the anthocyanin metabolic pathway. Anthocyanins form a large subclass of flavonoids conferring different colors typically red, purple, or blue in fruits and flowers. The structural genes involved in the anthocyanin biosynthetic pathway of plants include chalcone synthase, chalcone isomerase, flavanone 3-hydroxylase, flavonoid 3,5-hydroxylase, dihydroflavonol 4-reductase, anthocyanidin synthase, leucoanthocyanidin dioxygenase and UDP-glucose: flavonoid 3-O-glucosyltransferase. These genes are well characterized in model plants as well as fruit species including grape, apple and litchi (Litchi chinensis). In addition, a number of studies have demonstrated that anthocyanin accumulation is largely regulated by MYB transcriptional factors, which manipulate the expression of the structural genes in the anthocyanin biosynthetic pathway (Boss et al., 1996 Plant Physiol. 111: 1059-1066; Niu et al., 2010 Planta 231:887-899; Petroni et al., 2011 Plant Sci. 181:219-22). Thus, in some embodiments, the product of interest of the present disclosure is an enzyme in the anthocyanin metabolic pathway. In some other embodiments, the product of interest of the present disclosure is a transcription factor regulating the anthocyanin metabolic pathway. In some particular embodiments, the product of interest of the present disclosure is a MYB transcription factor regulating the anthocyanin metabolic pathway.

In yet some other embodiments, the product of interest is involved in a tocopherol metabolic pathway. Tocopherols are a class of lipophilic antioxidants, and together with tocotrienols belong to the vitamin E family. The four forms of tocopherols (α-, β-, γ- and δ-tocopherols) consist of a polar chromanol ring and lipophilic prenyl chain with differences in the position and number of methyl groups. The biosynthesis of tocopherols takes place mainly in plastids of higher plants from precursors derived from two metabolic pathways: homogentisic acid, an intermediate of degradation of aromatic amino acids, and phytyldiphosphate, which arises from methylerythritol phosphate pathway. The regulation of tocopherol biosynthesis in photosynthetic organisms occurs, at least partially, at the level of key enzymes including p-hydroxyphenylpyruvate dioxygenase (HPPD), homogentisate phytyltransferase (HPT), tocopherol cyclase (TC), and methyltransferases. Accordingly, in some embodiments, the product of interest of the present disclosure is an enzyme in a tocopherol metabolic pathway. In certain other embodiments, the product of interest of the present disclosure is a regulator of a tocopherol metabolic pathway that is selected from p-hydroxyphenylpyruvate dioxygenase (HPPD), homogentisate phytyltransferase (HPT), tocopherol cyclase (TC), and methyltransferase.

In still other embodiments, the product of interest is involved in a carotenoid metabolic pathway. Carotenoids are a diverse group of isoprenoid pigments widely distributed in nature. The vivid yellow, orange, and red colors of many fruits are attributed to the accumulation of carotenoids. This physical property of carotenoids is due to a polyene chain with a number of conjugated double bonds that functions as a chromophore. Carotenoids are synthesized by all photosynthetic organisms including plants, as well as some non-photosynthetic bacteria and fungi. Plant carotenoids are tetraterpenes derived from the 40-carbon isoprenoid phytoene. In plants, carotenoids are synthesized in all types of differentiated plastids but accumulate in high levels in the chloroplasts of green tissues and the chromoplasts of roots, fruits, and flower petals. Accordingly, the genetic constructs of the present disclosure may be used to genetically engineer a carotenoid metabolic pathway by containing a heterologous nucleotide sequence encoding an enzyme in the carotenoid metabolic pathway, or a regulator regulating the carotenoid metabolic pathway. Examples of the enzyme and regulator include, but are not limited to, the three upstream enzymes belonging to the methylerthritol-4-phosphate (MEP) pathway that provides carotenogenesis building blocks: deoxy-d-xylulose 5-phosphate (DXP) synthase (DXS), DXP reductoisomerase (DXR) and geranylgeranyl diphosphate synthase (GGPPS); the carotenogenesis enzymes: phytoene synthase (PSY); phytoene desaturase (PDS); ζ-carotene isomerase (Z-ISO); ζ-carotene desaturase (ZDS); carotene isomerase (CRTISO); lycopene ε-cyclase (ε-LCY); lycopene β-cyclase (β-LCY); β-carotene hydroxylase (β-OHase) carotenoid cleavage dioxygenases (CCDs); 9-cis-epoxycarotenoid dioxygenases (NCEDs); and the transcription factors regulating carotenogenesis: RIN, TAGL1, AP2a, ERF6, DET1, APRR2-Like, SGR and BZR1-1D. For a more detailed description of the carotenoid metabolic pathway, see Schmidt-Dannert et al. (2000) Nature Biotechnology 18(7):750-754.

In some embodiments, the product of interest is involved in the lycopene metabolic pathway. Lycopene, which derives its name from the neo-Latin Lycopersicum—the tomato species, is a bright red carotene and carotenoid pigment and phytochemical found in tomatoes and other red fruits and vegetables, such as red carrots, watermelons, gac, and papayas. Lycopene is a key intermediate in the biosynthesis of many carotenoids, thus the lycopene metabolic pathway overlaps with that of carotenoids. Generally, synthesis of lycopene begins with mevalonic acid, which is converted into dimethylallyl pyrophosphate. Dimethylallyl pyrophosphate is then condensed with three molecules of isopentenyl pyrophosphate (an isomer of dimethylallyl pyrophosphate), to give the twenty-carbon geranylgeranyl pyrophosphate. Two molecules of this product are then condensed in a tail-to-tail configuration to give the forty-carbon phytoene, the first committed step in carotenoid biosynthesis. Through several desaturation steps, phytoene is converted into lycopene, which concludes the biosynthesis of lycopene. Breakdown of lycopene involves the two terminal isoprene groups of lycopene being cyclized by lycopene cyclase (LCY) to produce alpha- and beta-carotene, which can then be transformed into lutein and xanthophylls, respectively. Accordingly, the genetic constructs of the present disclosure may be used to genetically engineer the lycopene metabolic pathway, by containing a heterologous nucleotide sequence encoding an enzyme in the lycopene metabolic pathway or a regulator thereof. Examples of the enzyme and regulator include, but are not limited to, the three upstream enzymes belonging to the methylerthritol-4-phosphate (MEP) pathway that provides building blocks for lycopene biosynthesis: deoxy-d-xylulose 5-phosphate (DXP) synthase (DXS), DXP reductoisomerase (DXR) and geranylgeranyl diphosphate synthase (GGPPS); the lycopene biosynthesis enzymes: phytoene synthase (PSY); phytoene desaturase (PDS); ζ-carotene isomerase (Z-ISO); ζ-carotene desaturase (ZDS); carotene isomerase (CRTISO); the lycopene degradation enzymes: lycopene ε-cyclase (ε-LCY); lycopene β-cyclase (β-LCY); β-carotene hydroxylase (β-OHase) carotenoid cleavage dioxygenases (CCDs); 9-cis-epoxycarotenoid dioxygenases (NCEDs); and the transcription factors regulating lycopene metabolic pathway: RIN, TAGL1, AP2a, ERF6, DET1, APRR2-Like, SGR and BZR1-1D. For a more detailed description of the lycopene metabolic pathway, see Schmidt-Dannert et al. (2000) Nature Biotechnology 18(7): 750-754.

In yet other embodiments, the product of interest is involved in the betalain metabolic pathway. Betalains are a class of red and yellow indole-derived pigments found in plants of the Caryophyllales and some higher order fungi. Originally found from red beet (*Beta vulgaris*), betalains are widely used as a natural colorant. The advantage of betalain color is that the color does not depend on the pH and is more stable than that from certain other pigments such as anthocyanins. Betalains are classified into red (crimson) betacyanins and yellow betaxanthins. They are immonium conjugates of betalamic acid with cyclo-dihydroxyphenylalanine (cDOPA) glucoside and amino acids or amines, respectively. Only betacyanins are modified by glycosyl or acyl moieties. More than 50 molecular species of betacyanins and several betaxanthins have been isolated and identified, and novel betalain molecules are being reported in accordance with the progress in development of analytical equipment. The biosynthetic pathways of betalains and the enzymes and genes involved in the pathway are generally less well understood than those of flavonoids and carotenoids. More recently, betalains have been recognized as powerful dietary antioxidants (Kanner et al. (2001) J Agric Food Chem 9(11):5178-5185). Thus, expression of betalains in fruits would be desirable. Accordingly, the genetic constructs of the present disclosure may be used to genetically engineer the betalain metabolic pathway, by containing a heterologous nucleotide sequence encoding an enzyme in the betalain metabolic pathway or a regulator thereof. Examples of such product of interest may include, without limitation, tyrosine hydroxylase, dihydroxyphenylalanine (DOPA) dioxygenase, DOPA oxidase, DOPA 4,5-dioxygenase (DOD), cDOPA 5-O-GT (cDOPA5GT), and glucosyltransferase. For a more detailed description of the betalain metabolic pathway, see Polturak et al. (2016) New Phytologist 210(1):269-283.

In some embodiments, the product of interest of the present disclosure may be involved in a combination of the metabolic pathways described herein.

Other Construct Elements

Genetic constructs of the present disclosure, in addition to the promoter and the heterologous nucleotide sequence, may include additional construct elements that may be helpful in expressing a product of interest in plants. Examples of such additional construct elements include, without limitation, enhancers, silencers, promoters, 5' untranslated regions (5' UTRs), open reading frames (ORFs), exons, introns, protein-coding regions, functional RNA-coding regions. 3' untranslated regions (3' UTRs), terminators, transit peptides and localization signals, and fragments thereof. Genetic constructs incorporating these additional construct elements may be assembled using methods known in the art, including Sambrook et al., Molecular Cloning: A Laboratory Manual, 2nd Ed. Cold Spring Harbor Press, 1987 and Ausubel et al., Current Protocols in Molecular Biology, Greene Publishing, 1987.

In some embodiments, the genetic construct further contains an intron. As used herein, the term "intron" refers to any nucleic acid sequence comprised in a gene that is transcribed but not translated. Introns include untranslated nucleotide sequence within an expressed sequence of DNA, as well as the corresponding sequence in RNA molecules transcribed therefrom. A construct described herein can also contain sequences that enhance translation and/or mRNA stability such as introns. The intron on the genetic construct may be located within a genetic element or outside a genetic element. In some embodiments, the intron is located in the promoter of the genetic construct. The intron may be used in combination with the promoter to enhance expression, such as increased mRNA stability and enhanced translation efficiency.

In some embodiments, the genetic construct further contains a terminator. The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase (NOS), the octopine synthase (OCS) genes, and the 35S terminator of cauliflower mosaic virus (CaMV).

In some embodiments, the genetic construct further contains a selectable marker. "Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptll that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to bialaphos and glufosinate; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilization of xylose, or antinutritive markers such as the resistance to 2-deoxyglucose). Expression of visual marker genes results in the formation of color (for example β-glucuronidase. GUS or β-galactosidase with its colored substrates, for example X-Gal), luminescence (such as the luciferin/luciferase system) or fluorescence (green fluorescent protein. GFP, and derivatives thereof).

Expression Vectors

In one aspect, an expression vector containing a genetic construct of the present disclosure is provided. As used herein, the term "vector" refers to a nucleic acid molecule capable of transporting another nucleic acid to which it has been linked. Examples of vector include, but are not limited to, plasmid, cosmid, bacteriophage, bacterial artificial chromosome (BAC), yeast artificial chromosome (YAC), or virus that carries exogenous DNA into a cell. One type of vector is a "plasmid", which refers to a circular double stranded DNA loop into which additional DNA segments can be ligated. As used herein, "plasmid" and "vector" may be used interchangeably as the plasmid is the most commonly used form of vector. A vector may be a binary vector or a T-DNA that comprises the left border and the right border and may include a gene of interest in between. The term "expression vector" as used herein means a vector capable of directing expression of a particular nucleotide sequence in an appropriate host cell. Thus, a vector containing an expression construct is considered an expression vector.

Methods for producing and using expression vectors are well known in the art and are described generally in Sambrook et al., Molecular Cloning: A Laboratory Manual, 2nd Ed. Cold Spring Harbor Press, 1987, and Ausubel et al., Current Protocols in Molecular Biology. Greene Publishing, 1987.

Transgenic Plants of the Disclosure

In other aspects, transgenic plants and transgenic plant parts containing a genetic construct of the present disclosure are provided.

As used herein, a "transgenic plant" refers to a plant that has incorporated a heterologous or exogenous nucleotide sequence. i.e., a nucleotide sequence that is not present in the native (non-transgenic or "untransformed") plant or plant cell. "Transgenic" is used herein to include any cell, cell line, callus, tissue, plant part or plant, the genotype of which has been altered by the presence of heterologous nucleotide sequence including those transgenics initially so altered as well as those created by sexual crosses or asexual propagation from the initial transgenic plant. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

Plant Transformation

Improvement of plant varieties through genetic transformation has become increasingly important for modern plant breeding. Genes of potential commercial interest, such as genes conferring to a plant trait of disease resistance, insect resistance or improved quality, may be incorporated into crop species through various gene transfer technologies. The development of an efficient transformation system is necessary for the analysis of gene expression in plants. The requirements for such a system include a proper target plant tissue that will allow efficient plant regeneration, a gene delivery vehicle that delivers foreign DNA efficiently into the target plant cells, and an effective method for selecting transformed cells. In genetic transformation of dicotyledonous species, for example, transformation systems utilizing the bacterium *Agrobacterium tumefaciens* have been frequently used as vehicles for gene delivery. The preferred target tissues for *Agrobacterium*-mediated transformation presently include cotyledons, leaf tissues, and hypocotyls. High velocity microprojectile bombardment offers an alternative method for gene delivery into plants.

As used herein, the term "transformation" and "transforming" a plant cell encompasses all techniques by which a nucleic acid molecule may be introduced into such a cell. Examples include, but are not limited to: transfection with viral vectors; transformation with plasmid vectors; electroporation; microinjection; *Agrobacterium*-mediated transfer; direct DNA uptake; Whiskers-mediated transformation; and microprojectile bombardment. These techniques may be used for both stable transformation and transient transformation of a plant cell. The term "stable transformation" refers to the introduction of a nucleic acid fragment into a genome of a host organism resulting in genetically stable inheritance over two or more generations. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

Methods for transforming plant cells, plants and portions thereof are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants, Springer-Verlag, Berlin; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

The following are representative publications disclosing genetic transformation protocols that may be used to genetically transform the following plant species: citrus (Pena et al., 1995, Plant Sci. 104, 183); *Prunus* (Ramesh et al., 2006. Plant Cell Rep. 25(8):821-8; Song and Sink 2005, Plant Cell Rep. 2006; 25(2):117-23; Gonzalez Padilla et al., 2003, Plant Cell Rep. 22(1):38-45); apple (Yao et al., 1995, Plant Cell Reports 14, 407-412); tomato (U.S. Pat. No. 5,159, 135); banana (U.S. Pat. No. 5,792,935); pineapple (U.S. Pat. No. 5,952,543); strawberry (Oosumi et al., 2006, Planta 223(6):1219-30; Folta et al., 2006, Planta. 2006 Apr. 14; PMID: 16614818); *Rubus* (Graham et al., 1995, Methods Mol. Biol. 1995; 44:129-33). Transformation of other species is also contemplated by the disclosure. Suitable methods and protocols for transformation of other species are available in the scientific literature and known to those of skill in the art.

As used herein, a transgenic "event" or "line" is produced by transformation of plant cells with a genetic construct containing a heterologous nucleotide sequence, regeneration of a population of plants resulting from the insertion of the heterologous nucleotide sequence into the genome of the plant, and selection of a particular plant characterized by insertion into a particular genome location. The term "event" refers to the original transformant and progeny of the transformant, where the genetic construct is inserted in a particular genome location. Multiple transgenic events or lines may be produced from one transformation process. Different transgenic events or lines may possess different characteristics (e.g. transgene expression, desired phenotypes), depending on the copy of the genetic constructs being inserted into the plant genome and the location of the genetic construct being inserted into the plant genome.

Transgenic Plant Parts

In some embodiments, the present disclosure relates to a plant part of the transgenic plant, where the plant part contains a genetic constructs of the present disclosure.

As used here in, a "plant part" refers to any part of a plant, including cells, tissues and organs. Examples of plant parts include, but are not limited to, pollen, ovules, leaves, embryos, roots, root tips, anthers, flowers, fruits, stems, shoots, scions, rootstocks, seeds, protoplasts, and calli. In some embodiments, the plant part of the present disclosure is a stem, a branch, a root, a leaf, a flower, a fruit, a seed, a cutting, a bud, a cell, or a portion thereof.

A plant part may be in planta (i.e., in a non-laboratory environment), or it may be in culture (e.g., cell culture, tissue culture and organ culture). Plant parts include harvestable plant parts, as well as plant parts useful for propagation of progeny plants. A "harvestable part" is a plant part that may be collected for consumption and/or further use, including fruits, seeds, flowers, leaves, seeds, roots, etc. For citrus plants, the harvestable part is typically a fruit.

As used herein, the terms "propagation" and "reproduction" are used interchangeably to refer to the process of a progeny plant being generated from a plant part of a parent plant. There are two main types of propagation in plants: sexual propagation and asexual propagation. The term "sexual propagation" refers to generating a new plant from a seed. The term "asexual propagation", "vegetative propagation" or "clonal propagation" refers to generating a new plant from a part of a plant of a parent plant that is not a seed. A citrus plant may be propagated by sexual propagation or asexual propagation. The term "propagation material" or "propagating material" refers to a plant part that is used to propagate plants. For sexual propagation, the propagating material is a seed. For asexual propagation, the propagating material may be any non-seed plant part that is capable of regenerating into a new plant. For a more detailed description of plant propagation, see Hartmann and Kester (1975) Plant propagation: principles and practices (No. SB119 H3 1975).

Transgenic Detection

After a genetic construct is transformed into a plant, a plant part, or plant cell, testing may take place to confirm that the transformation has occurred and to assess the quality of the transformation. For example, when selecting among multiple transgenic events or lines that had been transformed with the same construct, the event or line selected should ideally have the intact target sequences of interest without rearrangements, insertions, deletions, or extraneous flanking sequences. As described below, methods and techniques of detecting the genetic construct of the present disclosure contained in a transgenic plant or transgenic plant part are known to those of skill in the art.

Presence

Methods for detecting the presence of a genetic construct in a plant, a plant part, or plant cell include traditional methods such as the polymerase chain reaction (PCR) and DNA hybridization using nucleotide probes (e.g. Southern blot; Southern (1975) J. Mol. Biol. 98(3):503-517), and the more recent methods such as thermal asymmetric interlaced-PCR (TAIL-PCR; Liu et al (1995) The Plant J. 8(3):457-463), droplet digital PCR (ddPCR; Hindson et al (2011) Anal. Chem. 83(22):8604-8610), and next generation sequencing (NGS; Varshney, et al. (2009). Trends Biotechnol. 27(9):522-530). In addition, methods for transgenic plant event-specific DNA detection are described in U.S. Pat. Nos. 6,893,826; 6,825,400; 6,740,488; 6,733,974; 6,689,880; 6,900,014 and 6,818,807.

Copy Number, Zygosity and Expression

For most plant transformation methods, integration of a genetic construct into the host plant genome occurs randomly, i.e., the genetic construct may be inserted into any location of any chromosome, and any number of genetic constructs may be inserted. As a result, the expression of the integrated genetic construct may be influenced by its chromosomal position, perhaps due to chromatin structure (e.g., heterochromatin) or the proximity of transcriptional regulation elements (e.g., enhancers) close to the integration site (Weising et al., 1988 Ann. Rev. Genet 22:421-477). In addition, the first generation of plants after transformation ("$T_0$ generation") are normally hemizygous (e.g., only one of the two genomes of a diploid somatic cell contains the integrated genetic construct). It is only after sexual reproduction could homozygous plants be obtained, i.e., in $T_1$ generation and above. Therefore, a large number of independent transgenic events are typically generated to compensate for the aforementioned uncertainties. The resulting collection of transgenic lines can then be screened to prioritize lead events that possess targeted transgene expression levels coupled with low-copy integrations.

Methods for detecting the copy number of the integrated genetic construct as well as the zygosity of a transgenic plant may include, without limitation, quantitative PCR (qPCR; Ingham et al. (2001) Biotechniques 31(1):132-141), ddPCR (supra), and NGS (supra). Methods for detecting the expression of a genetic construct in a transgenic plant may include, without limitation, reverse transcription PCR (RT-PCR; Stone-Marschat et al. (1994). J. Clin. Microbiol. 32(3):697-700), qPCR (Brunner et al. (2004) BMC plant biology 4(1):14-14). Northern blot (Alwine et al. (1977) Proc. Natl. Acad. Sci. 74(12):5350-5354) and Western blot (Burnette (1981) Anal. Biochem. 112 (2):195-203).

Methods of the Disclosure

Further aspects of the present disclosure relate generally to methods of using the genetic constructs disclosed herein.

Method for Modifying a Fruit Phenotype

Genetic improvement of plants through transgenic technology enables introduction of a specific trait of interest into a desirable plant variety. In conventional breeding approaches, the trait of interest is delivered through cross-pollination, which limits the trait to be within the same species or a close relative due to reproductive incompatibility (i.e., biological species boundaries); whereas transgenic technology allows transfer of a selected trait to be across the boundaries of genera or higher classifications. Further, in contrast to conventional breeding where introduction of a trait of interest often requires multiple generations of crossing and selection, the transfer of selected trait through transgenic technology is achieved in a single generation, which is especially important for breeding of fruit trees such as citrus trees and plums that have long breeding cycles.

Accordingly, in one aspect, the present disclosure provides a method of modifying a fruit phenotype in a plant, the method having the steps of: i) transforming a plant cell with a genetic construct of the present disclosure, where expression of the product of interest is associated with modification of the fruit phenotype; ii) regenerating a plant from the transformed plant cell; and iii) growing the regenerated plant to produce fruit of the modified phenotype.

Regeneration and Growth of Transgenic Plants

The processes of transformation, regeneration, and growth are required to modify a fruit phenotype in a plant. Methods and techniques of transformation, where a genetic construct of the present disclosure is delivered to a plant cell and incorporated into the plant genome, have been described above in other aspects of the disclosure. Following transformation, steps of regeneration and growth are necessary in order to recover a whole and fertile plant from the transformed plant cell, as described below.

As used herein, the terms "regenerate". "regenerating" and "regeneration" refer to the process of developing a plant from a transformed plant cell. This is typically accomplished through plant tissue culture, which is a collection of techniques used to grow plant cells, tissues or organs under sterile conditions on a nutrient culture medium of known composition. Plant tissue culture relies on the fact that many plant cells have the ability to regenerate a whole plant, a property known as "totipotency". Single plant cells, unorganized growths of plant cells ("calluses"), plant cells without cell walls (protoplasts), and other plant parts (e.g., leaves, stems or roots) can often be used to generate a new plant on culture media given the required nutrients and plant hormones. The plant part (e.g., cell, protoplast, tissue and organ) removed from a plant to be cultured is known as an "explant". During transformation, not all the explant's cells are transformed; typically a selectable marker is used to differentiate transformed from untransformed cells. In some embodiments, the genetic construct of the present disclosure comprises a selectable marker, such that the cells that have been successfully transformed with the genetic construct would contain the selectable marker. By growing the cells in the presence of an antibiotic or chemical that selects or marks the cells expressing the selectable marker, it is possible to separate transformed from untransformed cells. The transformed plant cell are then placed onto the surface of a sterile solid culture medium, which typically comprises inorganic salts, organic nutrients, vitamins, and plant hormones for plant regeneration. The composition of the medium, particularly the plant hormones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As shoots emerge from a culture, they may be sliced off and treated with auxin to produce roots, and develop into a plantlet.

The subsequent step is to grow the regenerated plantlets into mature plants that are able to produce fruit of the modified phenotype. Plantlets regenerated from tissue culture are very fragile as they have been cultured on nutrient media under aseptic conditions and grown in high humidity (nearly 100%). Under those conditions, the regenerated plantlets tend to have: i) fewer palisade cells, i.e., less photosynthetic capability; ii) poorer vascular connection between roots and shoots and thus reduced water conduction; and iii) less developed cuticle or waxy layer, which results in greater water loss through evaporation when the plantlet is transferred to a less humid environment. Since the regenerated plantlets are highly vulnerable to environmental stress, carefully controlled acclimation procedures are necessary for their survival. As used herein, the terms "acclimation", "acclimatization", and "hardening-off" are used interchangeably to refer to the transitional process in which a plantlet gradually adjusts to the changes in its environment (such as a change in temperature, humidity, and/or photoperiod). The initial regenerated plants are called $T_0$ plants and the seeds obtained from the $T_0$ plants belong to the $T_1$ generation. For more details regarding regeneration and growth of a transgenic plant, see Teng, et al., HortScience. 1992, 27: 9, 1030-1032. Teng, et al., HortScience. 1993, 28: 6, 669-1671, Zhang, et al., Journal of Genetics and Breeding. 1992, 46: 3, 287-290, Webb, et al., Plant Cell Tissue and Organ Culture. 1994, 38: 1, 77-79, Curtis, et al., Journal of Experimental Botany. 1994, 45: 279, 1441-1449. Nagata, et al., Journal for the American Society for Horticultural Science. 2000, 125: 6, 669-672, and Ibrahim, et al., Plant Cell. Tissue and Organ Culture. (1992), 28(2): 139-145.

Fruit Phenotypes

As used herein, the term "phenotype" may be used interchangeably with the term "trait", which refers a plant characteristic that is readily observable or measurable and is a result of the interaction of the genetic makeup of the plant with the environment in which it develops.

The phenotypes that impart distinctive quality in a fruit may be categorized into 1) appearance. 2) flavor, 3) texture and 4) nutritional value. Appearance may be determined by physical factors including, without limitation, size, shape, wholeness, presence of defects (blemishes, bruises, spots, etc.), finish or gloss, and consistency. Flavor is typically described by aroma (e.g. odor) and taste (e.g., sweetness and acidity). Texture may be measured by percentage of water, percentage of soluble solids, and percentage of insoluble solids. Fruits are a major source of both "macro" nutrients such as fiber and carbohydrates, and "micro" nutrients such as vitamin C, vitamin B complex (thiamin, riboflavin, B6, niacin, folate), vitamin A, vitamin E, minerals, polyphenolics, carotenoids, and glucosinolates. In addition, parameters related to juice quality are also important fruit traits, which include, without limitation, juice yield, total soluble solids (TSS), total acidity (TA). TSS/TA ratio, pectin content, pulp content, and fiber content. Further, characteristics related generally to the growth and development of fruit trees are also considered important fruit traits, which include, without limitation, fruit yield, fruit ripening and senescence (e.g., post-harvest shelf life), resistance to diseases and insects, tolerance to environmental stress (e.g. drought, heat, salinity), and resistance to herbicides.

In some embodiments, the fruit phenotype is selected from the group consisting of size, weight, color, shape, firmness, glossiness, flavor, aroma, secondary metabolite content, peel thickness, seed number, juice quality, juice sugar content, juice acid content, juice taste, juice color, and juice yield.

Types of Fruit

The method disclosed herein is applicable to a number of different fruit species. As used herein, the term "fruit" refers to its botanical meaning, i.e., the seed-bearing structure in flowering plants (angiosperms) formed from the ovary after flowering. Thus, in additional to the culinary fruits, fruits as used herein also include structures that are not commonly regarded fruits by culinary or common meanings, such as bean pods, corn kernels, tomatoes, and wheat grains.

Examples of culinary fruits include, but are not limited to, apples, pears, grapes, drupe fruits (e.g., peaches, apricots, nectarines, plums, pluots, cherries, greengages, apriums, and peacotums), citrus fruits (e.g., mandarin, tangelo, orange, lime, lemon, meyer lemon, clementine, grapefruit, pomelo, blood orange, and calamansi), berries (e.g., raspberries, strawberries, blueberries, blackberries, loganberries, lingonberries, cranberries, red currants, black currants, acai, *gogi*, bilberries, boysenberries, huckleberries, salmonberries, and acerola), *papaya*, cactus fruits (e.g., pitaya, prickly pear), melons (e.g., honeydew, cantaloupe, canary, watermelon, and *galia*), pumpkin, avocado, guava, cherimoya, pomegranate, banana, kiwi fruits, palm fruits, persimmon, tamarind, mangoes, pineapples.

Examples of fruits that are often considered vegetables in a culinary sense may include, but are not limited to, cucumbers, tomatoes, peppers, eggplants, pumpkin, beans, nuts and cereal grains tomatoes, cucumbers, squash, zucchinis, pumpkins, peppers, eggplant, tomatillos, okra, and avocado.

In some embodiments, the fruit of the present disclosure is selected from orange (*Citrus sinensis*), mandarin (*Citrus reticulata*), lime (*Citrus aurantifolia*), grapefruit (*Citrus paradisi*), lemon (*Citrus limon*), pomelo (*Citrus maxima*), citron (*Citrus medica*), papeda (*Citrus micrantha*), citrange (*Citrus sinensis×Poncirus trifoliate*), and *Prunus* sp.

Secondary Metabolites and Nutraceuticals

"Secondary metabolites" refer to compounds such as substrates, intermediates and products of secondary metabolism. Secondary metabolites usually do not appear to participate directly in growth and development. They are a group of chemically very diverse products that often have a restricted taxonomic distribution. Secondary metabolites normally exist as members of closely related chemical families, usually of a molecular weight of less than 1500 Dalton. Secondary metabolites in plants include e.g. alkaloid compounds (e.g. terpenoid indole alkaloids, tropane alkaloids, steroid alkaloids), phenolic compounds (e.g. quinines, lignans and flavonoids), terpenoid compounds (e.g. monoterpenoids, iridoids, sesquiterpenoids, diterpenoids and triterpenoids). In addition, secondary metabolites include small molecules, such as substituted heterocyclic compounds which may be monocyclic or polycyclic, fused or bridged.

In some embodiments, the fruit phenotype relates to the content of secondary metabolites in a fruit, including anthocyanin content, tocopherol content, fatty acid content, carotenoid content, lycopene content, betalain content, and flavonoid content.

Many plant secondary metabolites have value as pharmaceuticals or nutraceuticals. For example, plant phenolic compounds such as anthocyanins and flavonoids have been shown to have antioxidant and anti-cancerous properties. The antioxidant activity of these compounds is attributed to their ability to transfer hydrogen atoms or electrons of an aromatic hydroxyl group into a free radical, generating a more stable phenoxyl radical (Duthie et al., 2003), or to their ability to chelate metal ions such as iron and copper thereby acting as scavengers of singlet oxygen and free radicals (Rice-Evans et al., 1997). Today, this group of plant compounds is of great nutraceutical interest for their contribution to human health. As used herein, the term "nutraceutical" refers to a food or food component considered to provide medical or health benefits, including the prevention or treatment of disease. In some embodiments, the fruit phenotype is increased nutraceutical content.

Method for Creating Seedless Tomato

The present disclosure is based, at least in part, on the surprising finding that transgenic tomato plants (*Solanunm lycopersicum*) that have been transformed with genetic constructs comprising a promoter sequence of SEQ ID NO: 4 produce fruits that are without seeds or with small non-viable seeds. Thus, in one aspect, the present disclosure provides a method of creating a tomato plant with seedless fruit, the method having the steps of 1) transforming a tomato plant cell with a genetic construct of the present disclosure, where the promoter comprises the sequence of SEQ ID NO: 4, or a sequence having at least 90% identity thereto; ii) regenerating a tomato plant from the transformed tomato plant cell; and iii) growing the regenerated tomato plant to produce seedless fruit. Methods of transforming, generating and growing a transgenic plant are well known in the art, as described above in other aspects of the disclosure.

As used herein, the term "seedless" refers to the state of containing no viable seed. Thus, a seedless fruit may contain no seeds, or it may contain non-viable seeds. As used herein, the term "fruit" refers to its botanical meaning, i.e. the seed-bearing structure in flowering plants (angiosperms) formed from the ovary after flowering. Thus, fruits as used herein include structures that are not commonly regarded fruits by culinary or common meanings, such as tomatoes, bean pods, and cereal grains.

Seedlessness may be an important trait to meet the preference of consumers. Examples of plants where varieties producing seedless fruits have been selected and popularized include watermelons, grapes, citruses, pineapples, bananas, tomatoes, and peppers. Two main mechanisms have been suggested to be responsible for the formation of seedless fruits: (i) parthenocarpy, where the fruit develops in the absence of fertilization, as in cultivated pineapples, some Citrus cultivars, and bananas; and (ii) stenospermy, where pollination and fertilization are required, but embryos either do not form or they abort before completion of seed formation, as in seedless watermelons and many seedless grapes. In both cases, the plant must have an inherent or acquired ability to sustain fruit development in the absence of seed formation.

Without wishing to be bound by theory, it is thought that the mechanism of the seedless fruit of the present disclosure is related to genome duplication. Without wishing to be bound by theory, it is thought that the promoter sequence disclosed as SEQ ID NO: 4 interacts with the tomato genome, leading to genome duplication (see Example 4 and FIG. 7), which either triggers the known parthenocarpy or stenospermy mechanism, or acts through a novel mechanism to result in formation of seedless tomato fruits.

Accordingly, in some embodiments, a promoter comprising the sequence of SEQ ID NO: 4 may be used to produce seedless tomato. In some embodiments, the genetic construct used to create a seedless tomato may comprise a promoter sequence that is not completely identical to SEQ ID NO: 4, but has a certain degree of sequence identity, such as at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO: 4.

A plant promoter typically comprises a core promoter, and often, additional regulatory elements. The core promoter is the minimal sequence that is required for directing basal level of expression, comprising a TATA box region where RNA polymerase. TATA-binding protein (TBP), and TBP-associated factors may bind to initiate transcription. In addition to the core promoter, further sequence elements are often necessary for initiating transcription that has a tissue- or developmental stage-specific expression pattern. For instance, the TGTCACA motif has been found to be a cis-regulatory enhancer element necessary for fruit-specific expression in melon species (Yamagata et al. (2002) J. Biol. Chem. 277:11582-11590). In some embodiments, a promoter comprising critical sequences from SEQ ID NOS: 1, 2, 3, 4, or 5 that are necessary for promoting fruit-specific expression may be used to produce seedless tomato.

EXAMPLES

The present disclosure will be more fully understood by reference to the following examples. It is understood that various other embodiments may be practiced, given the general description provided above. They should not, however, be construed as limiting any aspect or scope of the present disclosure in any way.

Example 1: Identification of Candidate Fruit-Specific Promoters

The following example describes the identification of candidate fruit-specific promoters in citrus and plum.
Materials and Methods
In Silico Identification of Candidate Fruit-Specific Promoters Candidate citrus genes with fruit-specific or fruit-preferential expression patterns were identified from analysis of microarray gene expression data at the Gene Expression Omnibus (GEO) data repository (www.ncbi.nlm.nih.gov/geo). GEO is a public functional genomics data repository supporting MIAME-compliant data submissions, where array- and sequence-based data are accepted and tools are provided to help users query and download experiments and curated gene expression profiles. The promoter sequence for the corresponding genes was predicted and obtained from the *Citrus sinensis* annotation project (http://citrus.hzau.edu.cn/cgi-bin/blast/blast.cgi) and plexdB.org. The 'Microplatform citrus' program was utilized for BLAST analysis of the Affymetrix IDs. The 'GBrowse' program was used for predicting exon and intron sequences of the candidate genes, and the 1-2 kb sequence upstream of the start codon was predicted to be the promoter sequence.

Sequence data for candidate plum genes with fruit-specific or fruit-preferential expression patterns were obtained from the USDA plum genome sequence database. Briefly, leaves of the European plum (*Prunus domestica*) variety 'Improved French' were ground in liquid nitrogen, from which genomic DNA was extracted using the EZNA™ High Performance (HP) DNA Kit (Omega Bio-Tek, Norcross, Ga.) with the addition of 2% Polyvinylpyrrolidone-40 (PVP-40) (w/v) to CPL buffer and 2-mercaptoethanol. Genomic DNA quantity was assessed using the Quant-iT PicoGreen kit (Invitrogen, Carlsbad. Calif.). A total of 2 µg of purified DNA was provided to David H Murdock Research Institute. Kannapolis, N.C. for library construction and sequencing. A paired-end and a mate-pair library were constructed with an average insert size of 375 bp and 2,950 bp, respectively.

These libraries were sequenced using an Illumina HiSeq 2000 sequencer. A total of 194,856,870 100-bp paired-end sequence reads and 158,319,386 mate-pair sequence reads were obtained. Sequence reads were assembled against the peach (*Prunus persica*) genome version 2 (Verde et al., BMC Genomics (2017) 18:225, https://www.rosaceae.org/species/prunus_persica/genome_v2.0.a1) using the CLC Genomics Workbench reference assembly tool (Qiagen, Valencia. Calif.) with two modifications to the default settings: length fraction=0.7 and similarity fraction=0.85. The ~2000 bp assembled sequence upstream of the known *Prunus domestica* MybA gene was predicted to be the promoter of the gene. Primers were designed based on the assembled *Prunus domestica* genomic sequence (with the reverse primer positioned inside the open reading frame of MybA) to amplify across the predicted region for isolation of the candidate plum promoter PfeMybAp from the wild/feral plum *Prunus americana*.

Results

To obtain candidates for novel fruit-specific promoters with unique activities, novel fruit-specific genes were identified. Genes that showed fruit-specific expression were selected using gene expression data from www.ncbi.nlm-.nih.gov/geo/. The microarray databases from several different citrus tissues were used to identify candidate citrus genes for fruit-specific expression. Consequently, four citrus genes were selected based on this analysis (candidates #1-4), which show a high level of expression in fruit and flower with some degree of expression in peel but not in leaves (FIG. 1). The target description and Affymetrix ID of these four candidate citrus genes are shown in Table 1. Additionally, one candidate plum gene (candidate #5) was identified and included in further studies.

TABLE 1

Candidate fruit-specific citrus genes

| Candidate | Gene ID | Affymetrix Probe Set ID | GenBank Accession | Target Description |
|---|---|---|---|---|
| #1 | Cs7g10980 | Cit.144.1S1_s_at, Cit.29312.1.S1_s_at | CB293157 | Sepallata3 MADS-box protein 4 |
| #2 | Cs1g02750 | Cit.11241.1.S1_s_at | CX049273 | Aldehyde decarboxylase, WAX2, CER1 fatty acid hydroxylase |
| #3 | Cs5g31450 | Cit.29634.1.S1_at | CK935639 | Unknown |
| #4 | Cs6g16160 | Cit.12380.1.S1_at | CF509979 | Cl111 juice sac promoter |

Candidate Fruit-Specific Genes and their Promoters

Citrus-derived candidate #1 has a target description of sepallata3 MADS-box protein 4 and is hereinafter referred to as CitSEP. The 3.56-kb sequence upstream of the start codon contains the promoter plus the first intron fragment of the gene, hereinafter referred to as CitSEPp. Because the first intron of the *Arabidopsis* SEP3 ortholog has been shown to be important for floral specificity when tested by the promoter fused to a reporter gene, it is likely that the citrus first intron is required as well.

Citrus-derived candidate #2 has a target description of aldehyde decarboxylase/WAX2/CER1 fatty acid hydroxylase, hereinafter referred to as CitWAX. The corresponding promoter is hereinafter referred to as CitWAXp.

Citrus-derived candidate #3 has an unknown target description, and is hereinafter referred to as CitUNK, with its promoter referred to as CitUNKp. The orientation of the gene in the genome was confirmed based on presence of poly-A tail on an EST, despite this orientation being in conflict with the annotated *C. sinensis* genome sequence. Based on the bioinformatics data, promoter CitUNKp should control fruit specific transcription although the encoded protein has an unknown function.

Citrus-derived candidate #4 has a target description of C1111 juice sac promoter (Sorkina et al. Plant Cell Rep. (2011) 30:1627-1640). This promoter is hereinafter referred to as CitJuSacp.

Plum-derived candidate #5 has a promoter sequence obtained from the feral plum MybA gene (PfeMybA). The promoter is hereinafter referred to as PfeMybAp.

Conclusion

Taken together, the results indicate that novel fruit-specific promoters were successfully identified from analysis of microarray expression data. Candidate fruit-specific promoters include four derived from citrus (*Citrus sinensis*: CitSEPp, CitWAXp, CitUNKp and CitJuSacp) and one from plum (*Prunus americana*: PfeMybAp).

Example 2: Isolation and Sequence Characterization of the Fruit-Specific Promoters As described in Example 1, four citrus promoters and one plum promoter were chosen for further studies. The following example describes the isolation of nucleotide sequence, generation of genetic construct, and comparison and annotation of the various elements of the fruit-specific promoters.

Materials and Methods

Promoter Isolation 5 grams of young leaves were harvested from trees and frozen in liquid nitrogen. Tissue was ground to fine powder from which genomic DNA was isolated. The Gentra Puregene DNA Purification Kit (Qiagen, Valencia, Calif.) was used following manufacturer's extraction protocol for 'Frozen Leaf Tissue'. Primers used for PCR amplification of the promoter sequences are summarized in Table 2.

TABLE 2

Primers used for PCR amplification of the promoter sequences

| Promoter | Primer | Sequence | SEQ ID NO. |
| --- | --- | --- | --- |
| CitSEPp | CitSEP_FOR1_KpnISbfI 61 | 5'-ttttGGTACCCCTGCAGGGCCATGGGAGAAGGTGCACATACTTTAG-3' | 6 |
|  | CitSEP_Rev1_XmaIClaI55 | 5'-ttttCCCGGGATCGATTTTCTTCTCCTTTCTTTCTTCTTCTATCAC-3' | 7 |
|  | CitSEP_INT FOR2 ClaI54 | 5'-ttttATCGATCTCCAATAGAGGAAAGCTGTACG | 8 |
|  | CitSEP_REV10_NotIPmeI55 | 5'-ttttGCGGCCGCGTTTAAACGTTGCACTTCTGGTACCTCTC-3' | 9 |
| CitWAXp | CitWAX_REV1_NcoI 61 | 5'-tttCCATGGTGCACTTTGAGGTAATGCAACATGCAATTGCTAG-3' | 10 |
|  | CitWAX_INT FOR2_EcoRI 59 | 5'-tttGAATTCGAGAGGAAGAGAACAACAAATTAATAAAGGCGG-3' | 11 |
| CitUNKp | CsUNK_FOR EcorI 58 | 5'-aaaaCCATGGTTGTCTGTGGCATTCACTGGAGAGAT-3' | 12 |
|  | CsUNK_REV NcoI 59 | 5'-aaaaCCATGGTTGTCTGTGGCATTCACTGGAGAG-3' | 13 |
| CitJuSacp | CitSin_JuSac_FOR2_EcoRI 52 | 5'-tttGAATTCGAGAGGAAGAGAACAACAAATTAATAAAGGCGG-3' | 14 |
|  | CitSin_JuSac_REV1 NcoI 53 | 5'-tttCCATGGTTTTTTCTATTTCATTCTTTCAGATTTTAAGC-3' | 15 |
| PfeMybAp | PfeMybA SbfI F61 | 5'-agtcCCTGCAGGGATTTTCCACCTAATTGCACATCGATCCAAACG-3' | 16 |
|  | PfeMybA NcoI R59 | 5'-agtcCCATGGTTTCTTTGGGCAGCGTTGTATGCTTGCAGC-3' | 17 |

Molecular Constructs

Figure 2:
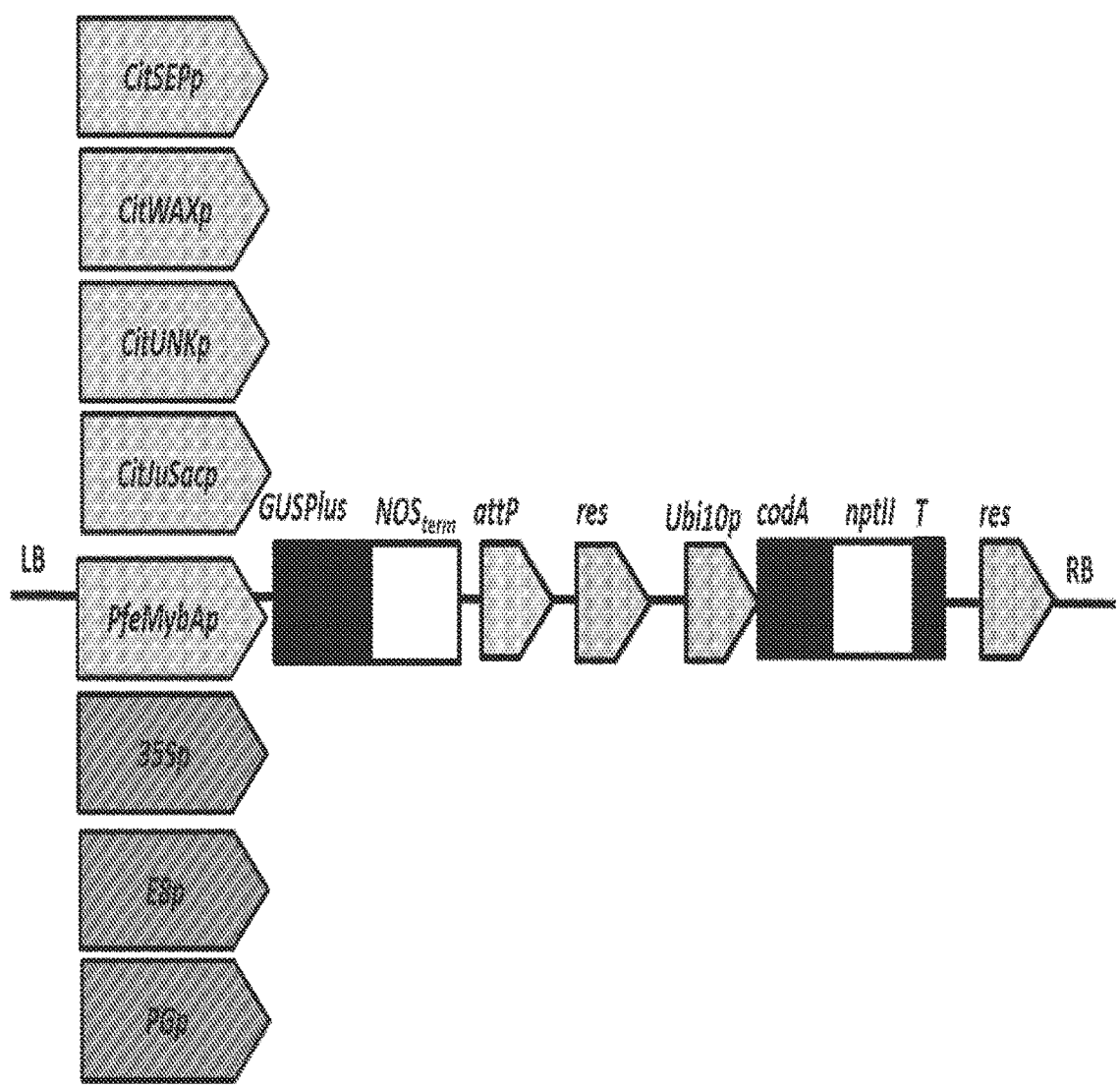
FIG. 2 shows the genetic constructs containing selected candidate fruit-specific promoters from citrus (CitSEPp, CitWAXp, CitUNKp, CitJuSacp) and plum (PfeMybAp), as well as fruit-specific promoters from tomato (E8p and PGp) and constitutive promoter 35Sp as controls.

The fruit-specific promoters, together with control promoters (i.e. the double enhanced CaMV 35S promoter 35Sp. the E8 promoter E8p, and the PG promoter PGp), were PCR amplified, digested, and cloned into pCTAGII-GUSPlus vector (deposited in GenBank at NCBI with accession number MG818373) for DNA sequencing. A diagram showing the molecular constructs is presented in FIG. 2.

DNA Sequencing

Molecular constructs that contain the fruit-specific promoters were processed for DNA sequencing. 1 milliliter of E. coli liquid culture is centrifuge-harvested with supernatant disposed. Tissue was ground to fine powder from which genomic DNA was isolated. ZR plasmid miniprep-classic (Zymo Research Corp.) was used following the manufacturer's extraction protocol.

Analysis of Promoter Elements

Analysis of putative cis-regulatory elements within the fruit-specific promoters was performed with the Plant Promoter Analysis Navigator, the Plant Cis Acting Regulatory Element (PlantCARE) search tool, and the Database of Plant Cis acting Regulatory DNA Elements. Additional known cis elements that were not included within the above websites' databases were queried and annotated manually. Websites of the tools used in this study are listed below:
http://plantpan.mbc.nctu.edu.tw/index.php
http://bioinformatics.psb.ugent.be/webtools/plantcare/html/
http://www.dna.affrc.go.jp/PLACE/
http://133.66.216.33/ppdb/cgi-bin/index.cgi
http://element.mocklerlab.org/
http://www.mocklerlab.org/tools
http://element.mocklerlab.org/motif_finders/new.

Results

Promoter Isolation and Sequencing

Approximately 1.0-3.0 kb of the region immediately upstream of a translation initiation codon (ATG) was predicted to be the promoter region in each case. The promoter sequences were PCR amplified from sweet orange and feral plum genomic DNA, and cloned into the pCTAG2 vector series. Promoter sequences based on DNA sequencing of these vectors were used for further element characterization. Nucleotide sequences of the isolated promoters CitSEPp, CitWAXp, CitUNKp, CitJuSacp and PfeMybAp are included herein as SEQ ID NO: 1, SEQ ID NO: 2, SEQ ID NO: 3, SEQ ID NO: 4 and SEQ ID NO: 5, respectively. Sequences are listed below.

SEQ ID NO: 1; *Citrus sinensis*; Name: CitSEPp (SEQ ID NO: 1)

5'

GCCATGGGAGAAGGTGCACATACTTTAGGCATCTGATGCAAATCACAACTAAAAAATGa

AGAGAAATCTGGATTTATATATATATACTGATCTATTCTTATCTTTGTACCTTGTTTTATT

TTATTTTATTAAGTAAAATCAATCACTTGTTATCTTTATTTTTCAGACAATCCCGAGGGGT

AAACCAGTGAATTTATATAGAAAACAACGGAACTACGAAGCTGTTCTGTTTCAGCTTTAC

ACGTAATTGGCCGAAGGAAATAGTCAGGTGGGGATAATCAAAAACCTCGTTCACTTCTC

ATCTCGACACGTGTCAATGTCCATTTATTTAATTACCTCACCTCTCCTCTTCTAAGTCTGG

GATTTCCCTTATTTATTTTTTAAGAAAAAAAATGTCTAAGGTTCCCCCCCCCCCCtAT

GGCCTCTCCACCGTCTGATCAAAGAAATAGGGTATAATAATAACAACAATAAAAGTAAA

AATAAAGGAATGCAAAGCTAAAAGCAAAATAACGCTCCATAATATTCGTTTTGTTTTAC

ATTTATATTTTTTTTGATAcATTAAATCAtCTaGTATTTGAAAATCACATTgGACCCTGATT

AATTCAaATTCGAGCtAAGTAGGACCACTAGGACGGTAAAGTTCTCTCCCGACTAATCTA

AATTCGAGTCGAGTAAGATCACTAAGGCAAATTCGAGCCGAGTAAGATCACTCGGCGGC

AAAATTCTCCCAACAAGTATTTaATGCAtTTGTATTCTcAAGTCTCGAATCGAAGACTTTG

GTTAAGTTAGAACAACCTCATACTAGTTGActcACGCGCTTGTTaGTTTGTTATACACTTAT

ATGATAACAATAAGAGTCAAAATGAAGTCATACaGACCtaaTAATAATAATAATAATAATA

ATAATAGGGCAAAAAGAAAAGGTATAGGAAAGAGATCGAAGAaGCAATAGCGGAGGCA

ATATAATATAATACTAGAAGTGATAGATTATAAATAGATATATGAATATATAGTGATAG

AAGAAGAAAGAAAGGAGAAGAAAgacgtcGCTCTCATCATTTTCTCCAATAGAGGAAAGCT

GTACGAGTTTTGCAGTAGTTCAAGgtatacgcatatgcacacagatatgttatcaccaaaacaactaaacagctacaattaaat gaaaattatgaaacacaacacaaaaagctctctctttctctctctctctctcttctcacttggcttagctagggggggtctatgggagattctttcttt tgcttggtttcttgttttgaattccgactttggatcttgaaaccataagaaatattattttttgctgtttttgatcatcccaaagaaaaaaatattgataa agaggagaaagtattgtttctttggagactggagttgagttttttgcccttttggtgaatgtctcggcgttttagcagcttcactgtttccctcttctta ttcttgtttagatctgcaactgcaaaattcatcaaaagaagatactcacacacctcactcttacatcttttaatgtattattatcactgttatattcactc taattaatttcctctctttgttttctttttctccctgtcttttttctttttccatttgttttcgcctattcacactttcatttccattttgtttcctt cttttccgttttgcttcatttttttttcttcttacttcgaaaaagttcacctgatctattaatattcaattttccaaagcaaatcaaacctaatttc -continued

```
aagtagtcaccttatttttgttctttataagtaaatttactggttcttccaaatagttcaagctatttctttattttagtttaattagatctcatgaag
cttaaacatacaaattctgatagagggagagcgattttttttttttttgggtattttatttcatgctttctgcagttttcagccaaaaaaaaaaaaaa
atcatgcttaatttctgttttgatgagtctgaccaaatcaagccaaatatttaagacatttattagtgatttacccagctcaaattgtgttcttgatcaag
gttagttctttctgttgtatgagagttttggttctttccagtggatcatagcgttgttctttttatggagacatctccatatctgctgctgctgctgc
tttcagagcttaagctagggtttcatcttcccaaagttacttttgattttaagcttccttctttctcacacaaacacacacatgattcagatctgaactat
ttatgatgaattgactattgacatgttaagactgatttaactacatcaatctttaacttcttttttataatttttatcattattatgtatgaaaaaaatagg
gttttttttatttgtacattcactggattagaagttaatatttatcatgttcttttctgtcttttattttattttacttttattttttcttggggttaaat
tcggatggcatacaatctacacaataacttctgagttgtgtggaatacaaaatggattaacaaagagattttaaggaaattggaaaaggtgattataacct
agatataATTCCcctcccccccccccccaaaaaaaaaaacactttcttacaatacttcgctagataatttgatgttttattaattttaatgtacaat
gagggaaattaaagacagcttgatttacagtccccatatgttatttaacttttaaaaaaaaattgagggacataaaaatctcaagattaaacctaaagat
ttaggccttttgaattgaggcctatatcttcttttctttctctcccattctaatttaaaacttatcaataattccttgccagtgcaaacactagctagt
gactgatgttcatgtccatgcatttgtggagggttaattaataatgtattccttttttcattaataaattttatgcagatggaaacataatactagaaact
gaatatttattttctatcaaattgtttcctaagaactgaaacaggctctaaagcattaaccaaaccgatcctattgggttccaaaattttcttccttcc
tttccagtttcacccaatatatattaatctattgtgtggtttcattcaaagtcaaaattgtttttggtataacctttcatgcaatagttttcaattatttg
ttctctcattgtgattgattgttcagtaataatagttaatataactatcagtgcgtgagtgcgttcatttaatttgatgtgttatataatgcctttttttt
ttttttttttcaattcatctttcattgttgactaatatatttatgcaatttgcggagggctaatgtattccttttctttgataacccatgcgaaaattta
ttagCAT
```

SEQ ID NO: 2; *Citus sinensis*; Name: CitWAXp (SEQ ID NO: 2)

5'

```
GAGAGGAAGAGAACAACAAATTAATAAAGGCGGAGCAATGAATGCATGACGTCAAAAA
ATTCCTGCAGAGGTTAAGACAGAGTGCACAAGCACAGAAGCGAGCAGGTATCTGAAAA
CATGTATTTGATCTTTATTGGGGTAGCAAAAGCCGGTGAGAACAATAAATGGTTGTCGGT
GACAATTATAAACAATTGGGCCTAGTTGCACCTGCACTGTATGCTTTTATTATTGTTTTAC
TTTTTACTCTAGCACAATTTTACTGAAAAATGTCTTTTGCCCTCACAATACTCTTTATTCT
TTATGCTTAATTATCATATTATCATTTCTTTCATTTTTTTTGAAAAAAAAATAATTCTTAT
TTAAGAATTTAAATCAACTACAATATTTGTTTAATAGGACAATAACAGTTTTATATAAAT
TTTTTTCACTCCTAATTTTATTTTTTGAGATAAGATTTAAAAAAGAAACACCAATACACC
ATTATTATTTTTAACTTCTTATTTTAACTCCTCTATTTTATTATGATATTTACAAGTAATT
TAAAGTTAATACGTCCTCTTAATTATCAATGAGAGTGGATTTAACTTATTTTGAACTTAA
ATTTTGATTTAGATATTCAAACTAATTCGTATAATTGATTTAGTATATTCAAATAATTTAC
TTGTATAATTTTTTTTTAAATTTAATGTATAGTAATGACTCTATATTTTTATTCATAAACC
TTTATTTTTTTGATTAATTATTTTCTTAAGGAAAAAATTAAACAAATATATAAAGGACGA
TTGTGTTACAGAGAGCATTTAATAAAGCACCAATGGAGAAAAGGAACACTTGTCGCAGG
AGCGACTGACCCTAGCACTGCTCCTATTATTCCTTAGAAGAAGGGAGCGACTGACGCTA
GCACTGCTCCTATTATTAATTGTATTTTTTTTTTAAAAAAAAGAAAAGAACCTTAATTGC
TGCTACACACTTTAATGTGATAATTAAATAATCACGTGAGAGCTGGGGGTCAGCTAGCT
GTAGCTGTGACATTTTTAATTGAGGCCAACAAAATATCTCCACGTGTAACCGTAATGTTG
AATACCCAATTGGGCTTCGGGAAAGAAAAATTCCCCATTGATTGATCTCTCATTTGACTT
GACCGTCCTGATGATGACACGACATCTAACTTGAATCCATCATCCGAATGAACAAGAAC
```

ATTATATAATTAGCACCCCTCCAGCTCTACTAGCAATTGCATGTTGCATTACCTCAAAGT
GCAAACAAAGA

SEQ ID NO: 3; *Citrus sinensis*; Name: CitUNKp (SEQ ID NO: 3)

5'- cctcaatctgcaccactaagacgaatgacaagtgagctgaaacaataatataaaaatgtaaaactgtgaatcaattacaacaattgcatctaattagat gcacagatagactttgaaagtttgcaaagtccagccactcttggtaaactaataacggcattaadatgtttattaataacattaaaataatataagcaata tgactcataatctaaaataattttgagctaagacctttagaataaactctggtcgaatagtaattcaggattataactaattaagtaggctcaaaattttt ataacagatttgtataaaatattttgatatttttatttatactgatatttaatattttataatttaaatttcattattcatttattaataattatagaaa taaaatcaaaattaaaaatgaatacaaggaaatggggcaatgggtaggggatggggattccacctcgttctcgtcccttcctcgaataagaaattgagtat agacacacatgtatacatacatacatatatcctctttttagaaatctggaacaactggtattattttatttcttttccattgaaaaaaatgagacacga atatggagtaaatgtgagaaactaattagggaaatttggctagtttttatgataaactacttacatcagtccaaagaaacatttatgggacataccctta ttctctagccatgcattgtttgttttctttcataaaagtgtgcatgactgaaatttgtcatgtgatcggccatgtcttgtatctcaaactagattaaattg caaaacaattcatcacgtcgttttctttgtttaatttattgtcgtataaggatttatttctactgtaatgattcatatacagaaaaagaaactgttgcaat tagggctgcaataatggatcgatcgaaatgacaataagacaaattatgaagtaaaggctgttttttttttttctaaatgaaacataagctatttaatttt ccttttgttttatgtaaattggacttttactattagagttggactattggccattggcactcagctaatctcttcatgaatccttttttttttgttatag ttattttattttcaaaaatatcattttcttaaacgcactactctaaatattttatttaaatttttttattgttataactcaaagtagtttcgtactatatt tcattttttttgcactcttattgttactgtatatacatattaaaaagtattatgagtgataaaattttcaagtgaagttttataaggataacaaagggatg ccagtaactttactcttactgttatagcgattcagcccaaagtaaatgtatatatattatttatttaaaaaaataagagagagaaatttagtgggtcaaaa cgcattacctcaatatcttttaagcagataagttagatgagtcctttaatgagacccatcaacttaaattgatagaattttgaggaagtattgatgttcgt gaagcaatgctattatccatttactattaacttctcgtatatgatattagcattattaattaaaatatacatatgccaaatagtgaattgtaaagaattat ttcatgaatatccaataattttttaatttcttaaaattagtgggactcagcaaccctacccaagtgatagctttaattagtaggcacaccatccaaacat gatactctgattattattgtttaaagagtgagaattacttacatgggttaggggtcaccacctcaacatattaaaatgatgtgtaGGCTAATAAAAACTTA
CTAGTTTAGTGGGTACACTCCGAAACCCACTAATTTTTTATTTTAAATAAAGCCTACCGAATTAAATTGGATGAGTCCCGCGGCAGCACCTATCTAATCG
AGTCTAATGACAAAATAGAGTAAAATGAAGGATTAATCTGAAGTCTGCTTTACTGTTTCGGCTATAAGTAAAGGAGTAGTGACCAAGACTCTCCAGTGAAT
GCCACAGACAA SEQ ID NO: 4; *Citrus sinensis*; Name: CitJuSacp (SEQ ID NO: 4)

5'

AATGATTTGCAGATGCACTATAACATGGCTAATTGTTATAAAGGGCATAAATCCACCGA

TCACGTGATACCTTGTACTTTTATGAAATATTCATTAATTTITTTTCTTTATAATGTCTATC

TGAAATTTATAAAGTATATCACTTTTTTTACCTTTTCATTAACATCCTTAAAAGATTTAACA

TAATATTCACAAAATTTTTCTTCTGGATGTAAAAAGGATATTTAATCTTCTTTAAACGAT

AAAAAAGATTTCATCTTGCAGTTGTTGGGATTAATAATAATTACAAAACTATCTATAAAA

ACTCATCAAATTACGTATATAAAATCATAAAATTACCAAAAGAAGCACTGTAACTAATT

TGTAGCTTATTTACAACATAAATCAAGAACTCATGCTCATATAATTCATCTTAAATGACA

CGTCTTTGTCAACAGTAACAAAGTTTAACAGAAATAAATAAAAATGATCATAGTTATCTA

AAATGCATTCGAAATAATCATAAAATCATTTATGAGAAATCTTGAACATTATACTTTACT

TCCATAAAAAAAAAAATAATAGTATAAAACTAGTTAAGATAATCTTGGAGTTTACAGCT

TATTCCCATCAATCCAAAATAATAATACATTCTCGAAGCATTGAAAATAATAATCAATGA

ATACTCTTTTTATATTTAGGGATAAAATAATTATTTTTTAACATGTTGTTAACCCTCTAAT

GGTGCTAATTAAAAAAATAAAAACTAATAAATTTTATAAACTTCACATAAAAAGCTGTA

-continued

```
AAATAAAAAATATTTAATATAATTTTATAAAATATAAAGTATTAGATGATAGTATAAAA

GCAGTAAATATAATGGAGTTACTTCACTGTAAATTACAAATTTAATATTTATTTCTATAA

TTATACAGTCGTTAATAATGCTGCATCGTAAAACAGTTATAACATGATTAGATTCCAGTA

TGAAATATCGTCTATGTGGCTCCAATAGAGTAATGACAGCCACCCTTCCGGAGAAAAAG

GCAGAGAGCGGACGATTCGAATCTGGACATCTTGTTGGCGACTGGAGTGGGGAACGTGT

AACAATGTCATCAACTCGTCAAACCAAACTTTCATTAAATCAATTAATTACATGGTAGTT

TTGATGCCTTAAAGTCTTTGTGGTAAGTAGGAACTACCTACCAACTCTTCCCCCATATTTT

ATAAGAAGAATAAGAACAGCATGCGCCAGTGTTGCTCTTCTTACTTCTGCTTAAAATCTG

AAAGAATGAAATAGAAAAAA
```

SEQ ID NO: 5; *Prunus Americana*; Name: PfeMybAp (SEQ ID NO: 5)

```
5'
CCAAGCTTGATTTTCCACCTAATTGCACATCGATCCAAACGCTATCCCTCTATCCCTCCA

ATTAAATTATGTAGCTTCCTCTTGTTCTTCACGGGCTAAAATTCTATGTTTGCTATAGTGT

AGTTTCCACCAATGCCCCGTTTAAACTACAAATCAATCGGTCGTGTTTGAGCTTTTTGAA

TATTATCTTTTTACTTCATGTAAATTATTGTTTTCCTCTTTCAACTTAATCATATATCGTCC

AATATTATTCTTGTTGAAGTTTTGTCCCTTTTTTTAACTCTAAAGCTGAATTCCTATAAAG

GCTTGTAGTTTAAGTGGTTAAGAACACTTACTCATACACAAGTCCTTGCTTCGATTCCCC

CTCTCCCAATATTTACGTTAACATTCCACCAACTTTAGCTCAAGTAAGTATTACAATAAT

TTGAGGAAACAATGTTTAGGTGTTTTAGTTTAGTGGTTTGGTACTTCAATTGTCACGCGA

ATCnTGTTTTCATTTTCGTAAACCAGACACAACAAATTACAAACTAACACTTCAAAAGT

AAGGCAGACTGTTGGGAACATGCAGACGAAAAATCAAAAGCAGGATTGCAGGTGGGTA

ATCTGTTTTGACTATTAGACAATTTTATGCCAGTTGAAAACTGACTTTTCTGCGCATGTG

GAAATTGCACATATATATATGAGTGGACATCATCATCTGCAGACAAATCCAGATCCTGTT

TCATCATTAGCTTAGCTAAAGTGGAATAGTATGAAGATTACAGCCTAGTAGTTGGTGGA

GGCACGAAAGATTACAGCTACGCATGGGAAGTCTCGGTTAATGGGATGCCGGGTCCCCT

TTGAGTGTAGAAAAGCTGCTGCTCGACAAATAGGATACCAGCGGAGTCTAACATCCTAC

GAATAAACCGTTAACGCAGCAGCGCATATATATATGAGTTAGGTTGCCTATGAGTTATTT

ACACTAAGGTTTTCTACTTTTTCACAAAATTCTTTAAGGTTTTAGAAATTACACAAACAC

CCCCTTGAGGTTTTAAATTGTTTTCACAAAATTCATTTTCATTGATTTTTCAACCAAAGATT

GATGGATTTTATACAAAAAAAATTCTCCAAATGACAAAGTTGACCTTTGAGATTGGATTG

TAGATACTTTATTGAGGTTAATTTTCTCATTTGCATAAGTGTTTTTTTCAATGAAATCATC

AATTTTTGGACAAACAATCAACGAAAAAGGGATTTGTGAAAATAAACTTAAATCTCAGG

GGGTGTTCGTGTAATGTTTGAGACATGATGGAAGTTTTGTGAAAACACAAGAAACCTCA

GAGGGTGTTAGTGTAAATAGAAATATATTTAATAGTTTGACTGGTAGCTAATTTATGACA

GAATTAATAACTGTTGCAATCTTTTAAACTTCGTCACTTTTTGCTTATGTGGATATGAGGC

ATGCACGTCACTGGCCTGGTAAGGTTTAATTTGATGGTCTCCATGCGGTCGGAGACCCTT

TATTTATAATGCTAGGTGGCTTCTGGACGCTTAACTAACAGGCACAAAATAAGCTGGCTG

CAAGCATACAACGCTGTTCCAAAAGAAAACGGCGCG
```

Promoter Elements

FIGS. 3A-3E show the various sequence elements identified in the candidate fruit-specific promoters. Citrus is non-climacteric (i.e., it ripens without ethylene and respiration bursts), therefore no ethylene responsive element (ERE) sites were identified in any of the citrus promoter sequences, even though ERE is the most common fruit-specific element.

Figure 3A:
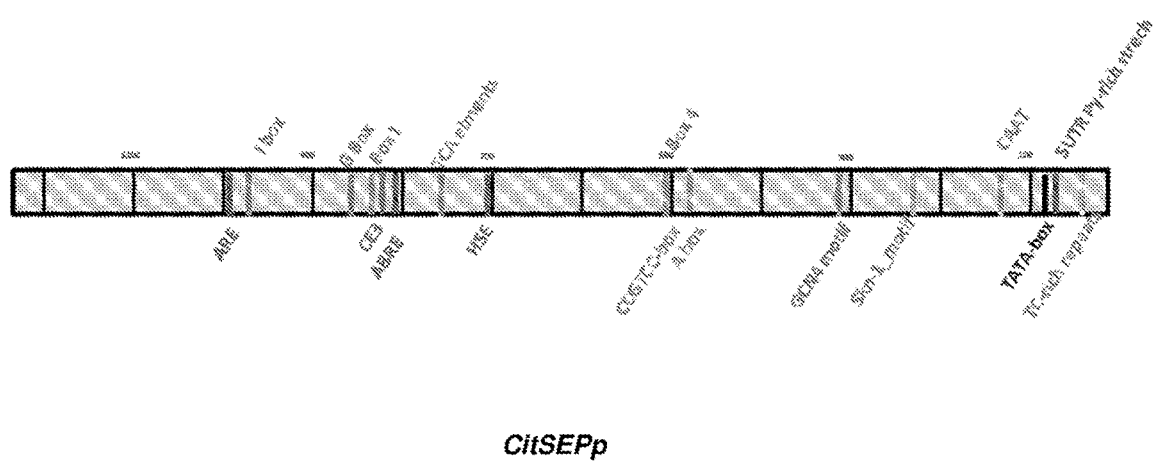
FIGS. 3A-3E show the various sequence elements identified in the candidate fruit-specific promoters.

FIG. 3A presents the sequence elements identified in the citrus promoter CitSEPp. CitSEPp was shown to have a cis-acting element that confers high transcription levels (5'UTR Py-rich stretch). Other interesting elements identified were the CCGTCC-box and CE3, which are responsible for ABA and VP1 responsiveness. Sequence analysis predicted TATA box and CAAT boxes. A summary of the promoter elements identified in CitSEPp is shown in Table 3.

TABLE 3

Promoter elements identified in CitSEPp

| Element | Function |
| --- | --- |
| 5UTR Py-rich stretch | cis-acting element conferring high transcription levels |
| A-box | cis-acting regulatory element |
| ABRE | cis-acting element involved in the abscisic acid responsiveness |
| ARE | cis-acting regulatory element essential for the anaerobic induction |
| Box 4 | part of conserved DNA module involved in light responsiveness |
| BOX I | light responsive element |
| CCGTCC-box | cis-acting element involved in ABA and VP1 responsiveness |
| CE3 | cis-acting element involved in ABA and VP1 responsiveness |
| G Box | cis-acting regulatory element involved in light responsiveness |
| GARE-motif | gibberellin-responsive element |
| GCN4_motif | cis-regulatory element involved in endosperm expression |
| HSE | cis-acting element involved in heat stress responsiveness |
| I-box | part of a light responsive element |
| Skn-1_motif | cis-acting regulatory element required for endosperm expression |
| TC-rich repeats | cis-acting element involved in defense and stress responsiveness |
| TCA-element | cis-acting element involved in salicylic acid responsiveness |

Figure 3B:
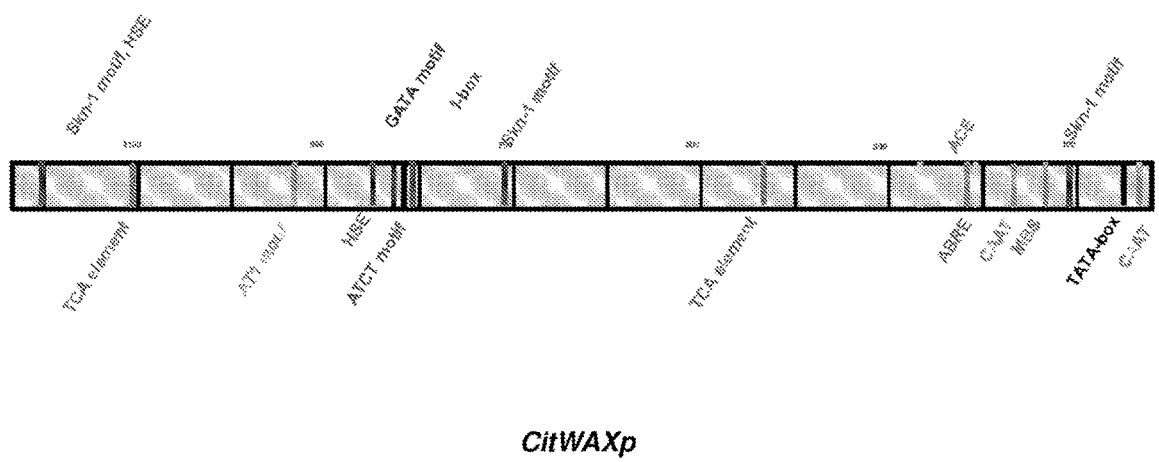

FIG. 3B presents the sequence elements identified in the citrus promoter CitWAXp. CitWAXp showed common potential regulatory elements associated with hormone, light and stress related responses. The presence of these putative cis elements indicates that the gene could be regulated by physiological (hormones) and environmental (light and stress) factors. A summary of the promoter elements identified in CitWAXp is shown in Table 4.

TABLE 4

Promoter elements identified in CitWAXp

| Element | Function |
| --- | --- |
| ABRE | cis-acting element involved in the abscisic acid responsiveness |
| ACE | cis-acting element involved in the light responsiveness |
| ATCT-motif | part of a conserved DNA module involved in light responsiveness |
| G-Box | cis-acting regulatory element involved in light responsiveness |
| HSE | cis-acting element involved in heat stress responsiveness |
| MBS | MYB binding site involved in drought-inducibility |
| O2-site | cis-acting regulatory element involved in zein metabolism regulation |
| TCA-element | cis-acting element involved in salicylic acid responsiveness |
| TGA element | auxin-responsive element |
| Box 4 | part of a conserved DNA module involved in light responsiveness |
| Box I | light responsive element |
| Box-W1 | fungal elicitor responsive element |
| AT1-motif | part of a light responsive module |
| TC-rich repeats | cis-acting element involved in defense and stress responsiveness |

Figure 3C:
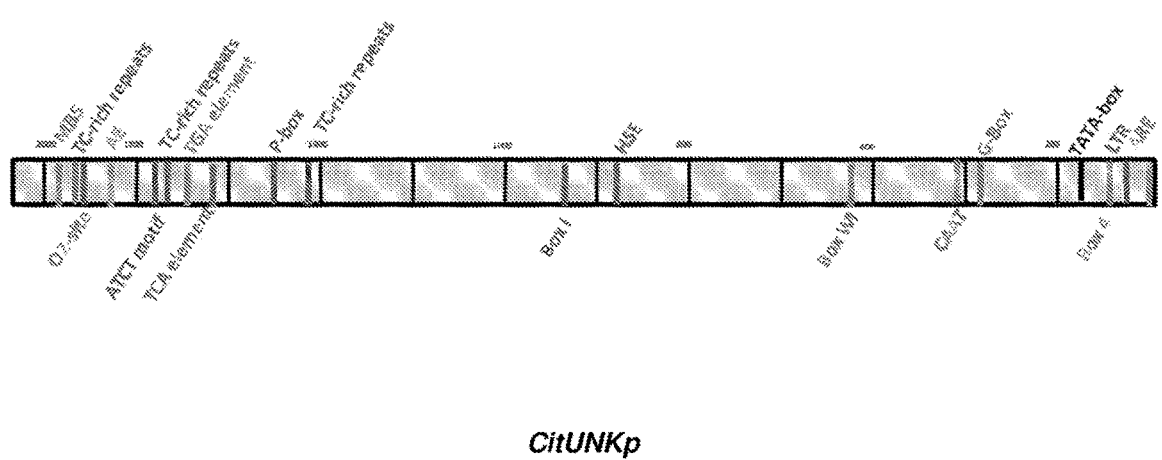

FIG. 3C presents the sequence elements identified in the citrus promoter CitUNKp. CitUNKp showed putative hormone responsive elements in the promoter region, including an ARE motif (involved in the abscisic acid responsiveness) and a TCA-element (involved in salicylic acid responsiveness). Also identified were cis-acting elements involved in light responses including an ATCT motif and a G-box. In addition, the promoter sequence was found to contain a number of cis-elements related to stress responses, including an HSE motif (involved in heat stress responses), an LTR motif (involved in low-temperature responses), an MBS site (MYB binding site involved in drought-induction) and TC-rich repeats (involved in defense and stress responses). A summary of the promoter elements identified in CitUNKp is shown in Table 5.

TABLE 5

Promoter elements identified in CitUNKp

| Element | Function |
| --- | --- |
| AE | part of a module for light response |
| ARE | cis-acting regulatory element essential for the anaerobic induction |
| ATCT-motif | part of a conserved DNA module involved in light responsiveness |
| G-Box | cis-acting regulatory element involved in light responsiveness |
| HSE | cis-acting element involved in heat stress responsiveness |
| MBS | MYB binding site involved in drought-inducibility |
| O2-site | cis-acting regulatory element involved in zein metabolism regulation |
| TCA-element | cis-acting element involved in salicylic acid responsiveness |
| TC rich repeats | cis-acting element involved in defense and stress responsiveness |
| TGA element | auxin-responsive element |
| Box 4 | part of a conserved DNA module involved in light responsiveness |
| Box I | light responsive element |
| Box-W1 | fungal elicitor responsive element |
| LTR | cis-acting element involved in low- temperature responsiveness |
| P-box | gibberellin-responsive element |
| TC-rich repeats | cis-acting element involved in defense and stress responsiveness |

Figure 3D:
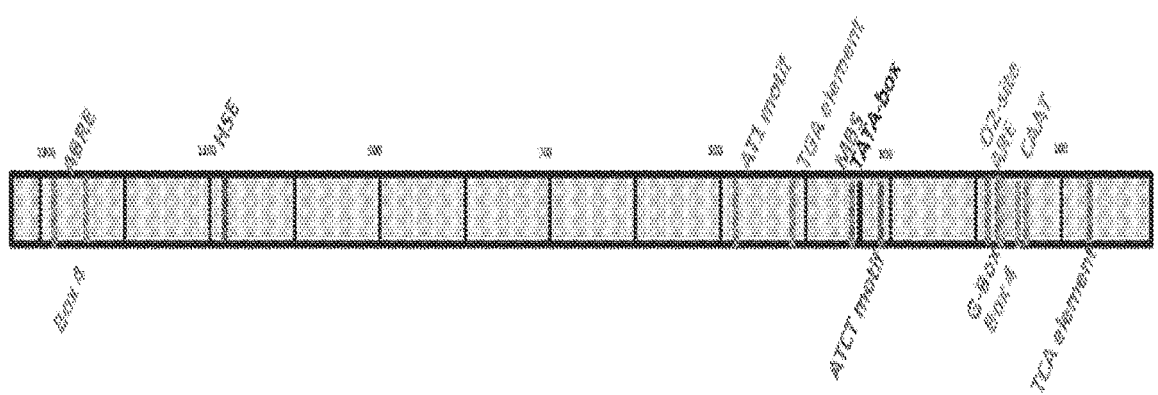

FIG. 3D presents the sequence elements identified in the citrus promoter CitJuSacp. CitJuSacp showed common potential regulatory elements associated with hormone, light and stress related responses. A summary of the promoter elements identified in CitJuSacp is shown in Table 6.

TABLE 6

Promoter elements identified in CitJuSacp

| Element | Function | Strand | Position | Sequence |
|---|---|---|---|---|
| ABRE | cis-acting element involved in the abscisic acid responsiveness | + | 61 | CACGTG |
| ARE | cis-acting regulatory element essential for the anaerobic induction | - | 1098 | TGGTTT |
| ATCT-motif | part of a conserved DNA module involved in light responsiveness | - | 944 | AATCTAATCT (SEQ ID NO: 32) |
| G-Box | cis-acting regulatory element involved in light responsiveness | + - | 61, 1071 | CACGTG, CACGTT |
| HSE | cis-acting element involved in heat stress responsiveness | + | 245 | AAAAAATITC (SEQ ID NO: 33) |
| MBS | MYB binding site involved in drought-inducibility | - | 26.1, 933 | CAACTG, TAACTG |
| O2 site | cis-acting reiulatory element involved in zein metabolism regulation | - - | 1080 | GATGACATGG (SEQ ID NO: 34) |
| TCA-element | cis-acting element involved in salicylic acid responsiveness | + | 1201 | GAGAAGAATA (SEQ ID NO: 35) |
| TGA element | auxin-responsive element | - | 907 | AACGAC |

Figure 3E:
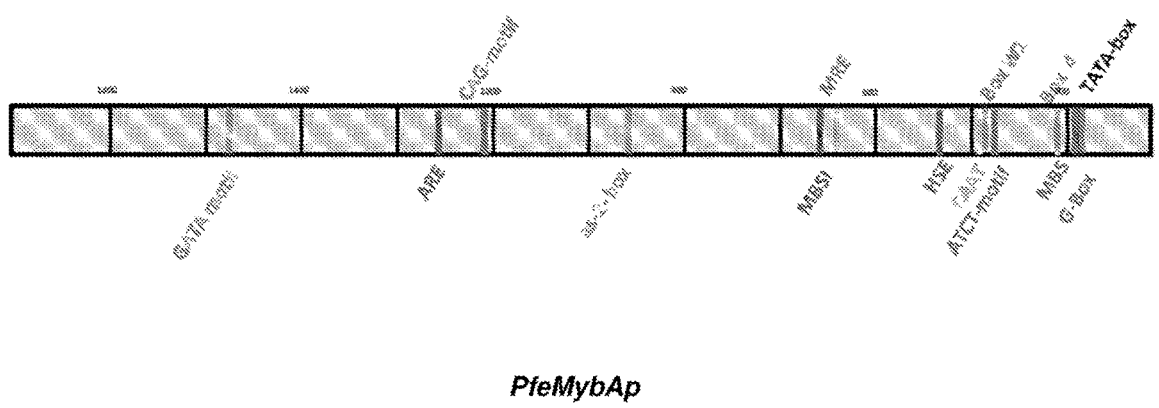

FIG. 3E presents the sequence elements identified in the plum promoter PfeMybAp. PfeMybAp was shown to contain putative cis elements such as MBSI, MRE and an as-2-box involved in flavonoid and light responsive signaling. A summary of promoter elements identified in PfeMybAp is shown in Table 7.

TABLE 7

Promoter elements identified in PfeMybAp

| Element | Function |
|---|---|
| ATCT-motif | part of a conserved DNA module involved in light responsiveness |
| ARE | cis-acting regulatory element essential for the anaerobic induction |
| ABRE | cis-acting element involved in the abscisic acid responsiveness |
| G-Box | cis-acting regulatory element involved in light responsiveness |
| HSE | cis-acting element involved in heat stress responsiveness |
| MBS | MYB binding site involved in drought-inducibility |
| Box-W1 | fungal elicitor responsive element |
| Box 4 | part of a conserved DNA module involved in light responsiveness |
| CAG-motif | part of a light response element |
| MBSI | MYB binding site involved in flavonoid biosynthetic genes regulation |
| MRE | MYB bindng site involved in light responsiveness |
| as-2-box | involved in shoot-specific expression and light responsiveness |

Conclusion

Taken together, the results provide successful isolation of the identified fruit-specific promoters and characterization of their sequences. Identification of the various regulatory elements of the candidate promoters from this study promotes a better understanding of mechanisms underlying gene expression specificity in fruit.

Example 3: Functional Characterization of the Fruit-Specific Promoters Using Agrobacterium-Mediated Transient Expression Assay The following example describes the functional analysis of the fruit-specific promoters using an Agrobacterium-based transient expression assay.

Materials and Methods

Molecular Constructs

The Promoter::GUSPlus molecular constructs used in this study are as described in Example 2. The vector contains the GUSPlus and Nos terminator sequences, as well as the attP and res recombination sites for future recombinase mediated construct exchange (RMCE) genomic targeting. The attP and res are recombinase recognition sites for the Bxb1 and CinH recombinase enzymes respectively. LB and RB designate the Agrobacterium left border and right borders, respectively. The vector also contains the nptll gene for kanamycin selection. In addition to the citrus and plum candidate promoter sequences, two fruit-specific promoters from tomato, E8p and PGp, along with the constitutive promoter 35Sp were used as controls for this study.

Agrobacterium Suspension

Agrobacterium cultures (5 mL) were grown overnight from individual colonies at 28° C. in LB medium plus selective antibiotics, transferred to 50 mL induction medium (0.5% beef extract, 0.1% yeast extract, 0.5% Peptone, 0.5% Sucrose. 2 mM MgSO4, 20 mM acetosyringone. 10 mM MES, pH 5.6) plus antibiotics, and grown again overnight. Next day, cultures were recovered by centrifugation, resuspended in infiltration medium (10 mM MgCl2, 10 mM MES, 200 mM acetosyringone, pH 5.6; optical density 0.5 to 1.0 unless stated otherwise), and incubated at room temperature with gentle agitation (20 rpm) for a minimum of 2 h. Cultures were combined when required, collected with a syringe, and injected into fruits as described below.

Agrobacterium Injection (Agroinjection)

Tomato fruits (*Solanum lycopersicum* cv Micro-Tom) were infiltrated using a 1-mL syringe with a 0.5-316-mm needle (BD Pastipak). Needle was introduced 3 to 4 mm in depth into the fruit tissue through the stylar apex, and the infiltration solution was gently injected into the fruit. The total volume of solution injected varied with the size of the fruit, with a maximum of 600 mL in mature green tomatoes. The progress of the process could be followed by a slight change in color in the infiltrated areas. Once the entire fruit surface has been infiltrated, some drops of infiltration solution begin to show running off the hydathodes at the tip of the sepals. Only completely infiltrated fruits were used in the experiments.

GUS Staining

β-glucuronidase (GUS) was detected using a GUS staining solution (0.1 M sodium phosphate pH 7.0, 0.5 mM potassium ferrocyanide. 0.5 mM potassium ferricyanide, 1.5 g/L X-Gluc, and 0.5% v/v Triton X-100) generally for 4 to 20 h at 37° C. The incubation time was adjusted based on the strength of the staining observed. After staining, green tissues were passed through several changes of 70% and 95% ethanol to remove chlorophyll.

Imaging

The Agroinjection images in petri plates were observed and photographed in a Leica MZ16-F (Leica Microsystems, Inc., Buffalo Grove, Ill.) stereo zoom light microscope equipped with a QImaging Retiga 2000 R fast cooled, digital color camera.

Results

To investigate the ability of the candidate promoter fragments to confer gene activity, the *Agrobacterium*-mediated transient expression assay was performed in tomato fruit tissue. Tomato fruits at mature green and ripe stages (22-25 d after anthesis) were Agroinjected using *Agrobacterium* suspensions containing the previously described Promoter:: GUSPlus molecular constructs (FIG. 3). Agroinjected fruits were then treated with GUS staining solution and visualized for qualitative analysis of the GUS expression, which reports the activity of the candidate promoter.

Candidate Promoters Drive Expression of the GUS Reporter Gene in Fruit

Figure 4:
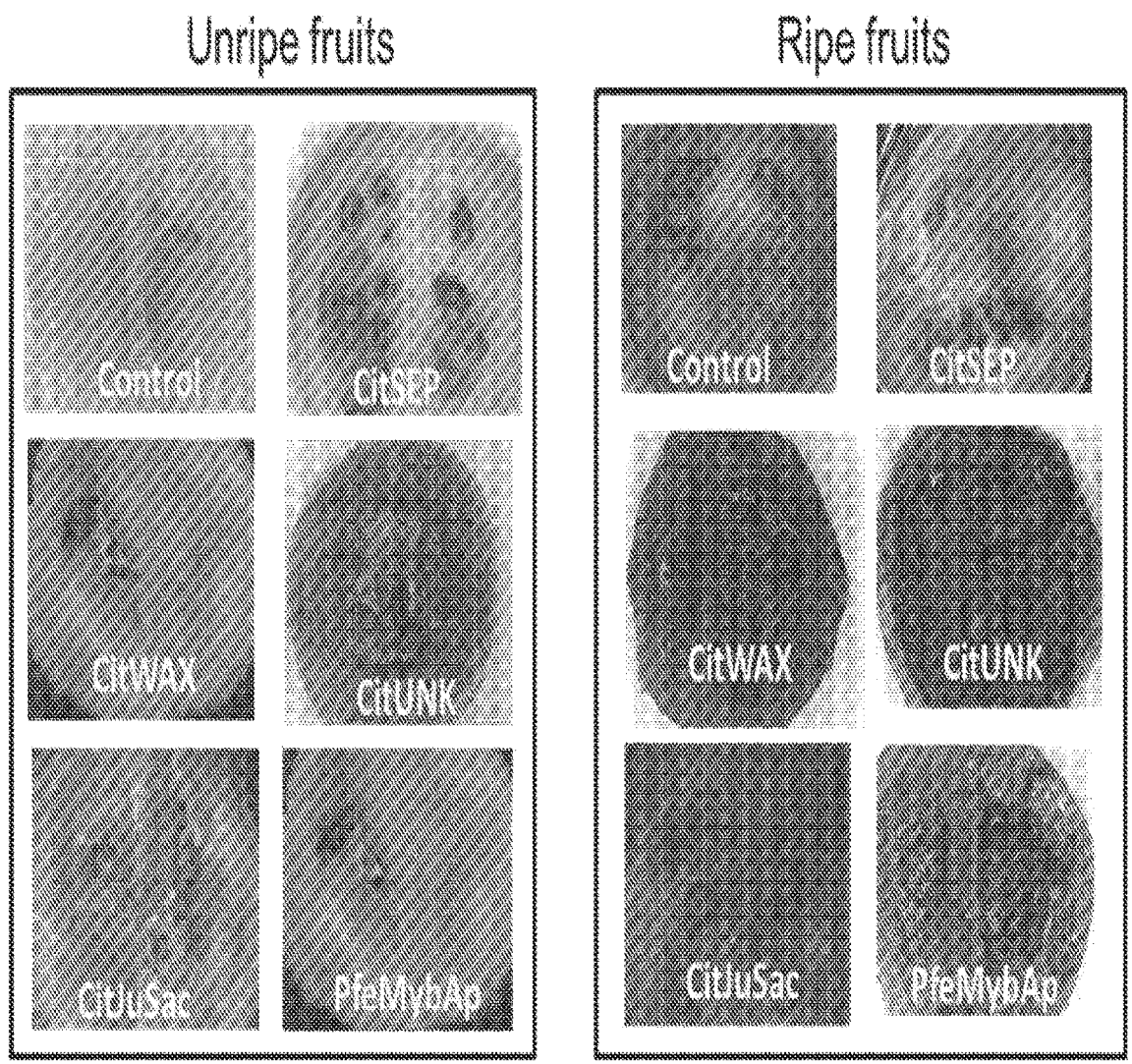
FIG. 4 shows the results of the *Agrobacterium*-mediated transient expression assay for testing the functionality of the candidate fruit-specific promoter::GUS constructs in unripe (left) and ripe (right) tomato fruits as compared to control (wide type tomato Agroinjected with empty vector).

GUS staining patterns of the Agroinjected tomato fruits are shown in FIG. 4. From the results, high levels of GUS activity (blue staining) were detected in fruits 4 d after Agroinjection. GUS expression was not detected in wild type tomato fruit Agroinjected with empty vector control, whereas strong and varied expression patterns were detected in fruits injected with various candidate promoter constructs. Different candidate promoters showed different intensities of GUS expression in immature versus ripe fruits. Similar amounts of *Agrobacterium* were injected into each fruit tested. CitSEPp lines showed very weak expression both in immature and ripe fruits; the staining was mostly the mucosal sack around the seeds. CitWAXp lines showed strong expression both in immature and ripe fruits. Cit-UNKp gave rise to the strongest GUS expression among all fruits both in young immature tomato fruits as well as in mature ripe fruits. CitJuSacp lines showed stronger expression in mature fruits compared to immature fruits, whereas PfeMybAp lines showed similarly strong expression in both unripe and ripe fruits.

Conclusion

Together, these observations demonstrated that the candidate promoters successfully drove expression of reporter gene in tomato fruit tissue via Agroinjection, indicating that the promoter candidates from citrus and plum contain active promoter elements regulating GUS expression patterns in tomato fruit.

Example 4: Functional Characterization of the Fruit-Specific Promoters Using Stable Transgenic Tomato Plants The following example illustrates the functional analysis of the fruit-specific promoters using stable transgenic tomato plants.

Materials and Methods

Transgenic Tomato Plants

Transgenic Micro-Tom Rg1 tomato plants were produced using pCTAGII-derived binary vectors (GenBank accession number MG818373) and kanamycin selection with an established *Agrobacterium*-mediated transformation method (Pino et al., 2010).

Droplet Digital PCR

Genomic DNA was extracted by grinding a 1-$cm^2$ piece of tomato leaf in 400 μL of buffer (200 mm Tris-HCl pH 7.8, 250 mm NaCl, 25 mm EDTA, 0.5% SDS). After centrifugation and isopropanol precipitation, the pellet was washed with 70% ethanol and resuspended in 50 μL of water with 1 mM RNase A. PCR amplification was performed using 2 μL of genomic DNA in reactions with a total volume of 25 μL. Presence of the transgene was confirmed by PCR using transgene specific primers. Droplet digital PCR (ddPCR) was performed following the methods in Collier et al., The Plant Journal (2017) 90, 1014-1025. Sequences of the ddPCR primers and probes that were used for detecting reference gene (CsUBC) are:

```
CsUBC_ddPCR-F2:
                                         (SEQ ID NO: 18)
5'-CGCTCAGGTGATATAAGAGG-3',

CsUBC_ddPCR-R2:
                                         (SEQ ID NO: 19)
5'-TGAATAGGGCTTCGTCAATC-3',
and CsUBC probe:
                                         (SEQ ID NO: 20)
5'-AAGGATGTACACTAGACTTGCGGC-3'.
```

GUS Staining

β-glucuronidase (GUS) was detected as using a GUS staining solution (0.1 M sodium phosphate pH 7.0, 0.5 mM potassium ferrocyanide, 0.5 mM potassium ferricyanide, 1.5 g/L X-Gluc, and 0.5% v/v Triton X-100) generally for 4 to 20 h at 37° C. The incubation time was adjusted based on the strength of the staining observed. After staining, green tissues were passed through several changes of 70% and 95% ethanol to remove chlorophyll.

Imaging of Transgenic Plants

The photographs of the plants were recorded using a Nikon D7000 digital camera with an AF Micro Nikkor 60 mm 1:2.8 D lens or AF-S Nikkor 18-70 mm DX lens (Nikon Inc., Melville, N.Y.) under tungsten lamps (Philips, 120 V. 300 W). The camera was set manually for all parameters including ISO sensitivity, focus, f-stop and time. A photography gray card was used as a reference to get the correct exposure.

Quantitative GUS Expression Assay

GUS expression was quantitated using the method described below and in *Cold Spring Harb. Protoc.*

(Blázquez, 2007). *Arabidopsis: A Lab. Manual. Cold Spring Harb. Lab. Press.* (Weigel and Glazebrook, 2002), and Jefferson et al., *EMBO J* (1987) 6:3901-3901. The expression of β-glucuronidase (GUS) can be accurately determined in extracts of plant tissue using 4-methylumbelliferyl β-D-glucuronide (4-MUG) as a substrate. Upon hydrolysis by GUS, the fluorochrome 4-methyl umbelliferone (4-MU) is produced. Using excitation at 365 nm and measuring emission at 455 nm, the amount of 4-MU produced can be quantified. Under these conditions, background fluorescence from the substrate is negligible, especially if the appropriate filter is selected.

Results

Generation of Transgenic Tomato Lines

A total of 15-20 independent T0 transgenic lines were obtained for each promoter construct using the *Agrobacterium*-mediated transformation method and were grown to maturity in a greenhouse. All tissue culture was done on kanamycin selection. The individual lines were PCR tested and were found to be kanamycin positive.

Figure 5:
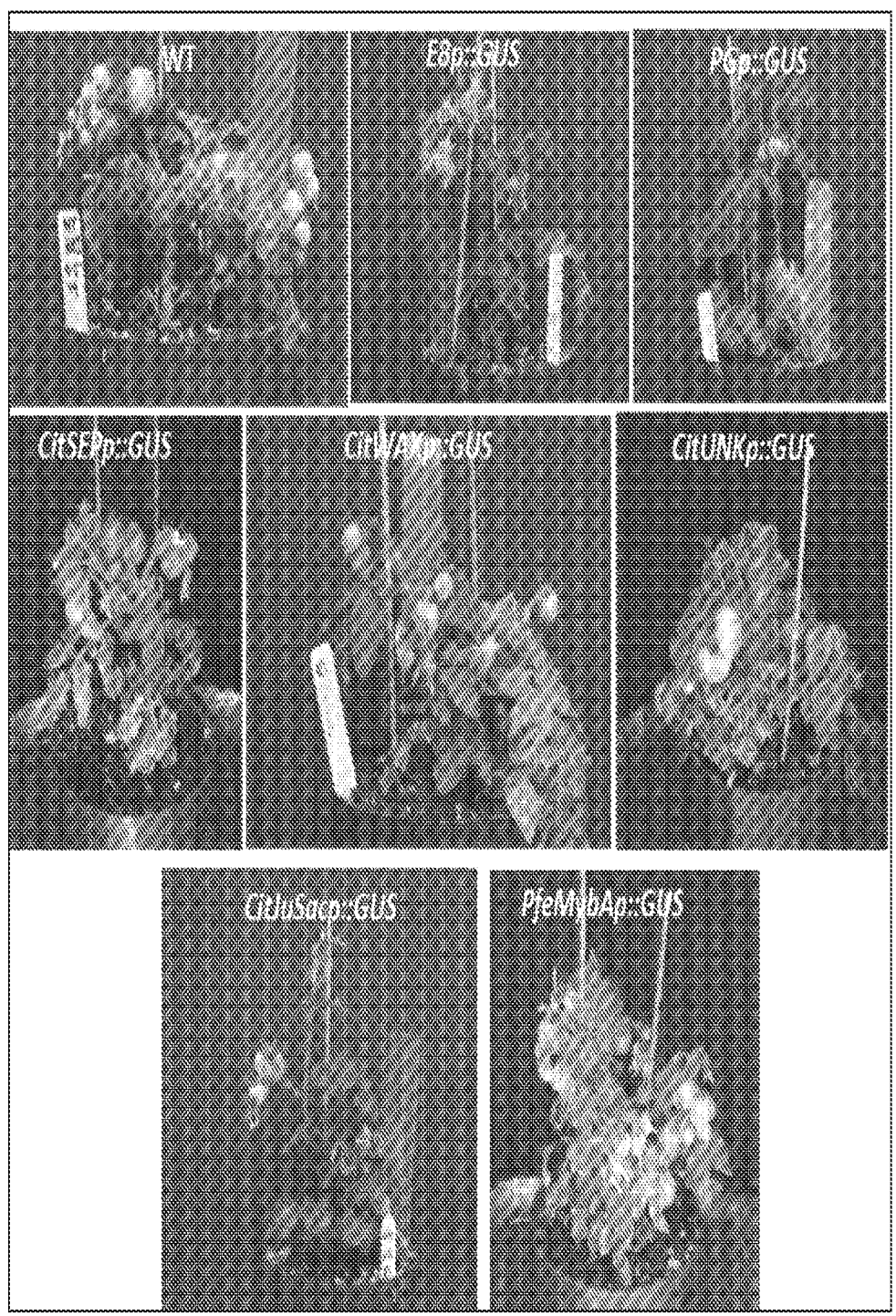
FIG. 5 shows the phenotypes of the transgenic tomato plants stably transformed with various Promoter::GUS constructs.

The individual lines were grown to maturity, with overall growth and development monitored. Compared to wild type (WT), the transgenic plants showed no significant difference in either vegetative or reproductive growth patterns, with the exception of the CitJuSacp lines (FIG. 5). Based on the kanamycin positivity and initial GUS analysis on vegetative and reproductive tissues, seeds were collected from selected T0 lines for further analysis in the T1 generation.

Seedless Fruit Phenotype of the CitJuSacp Transgenic Lines

Figure 6:
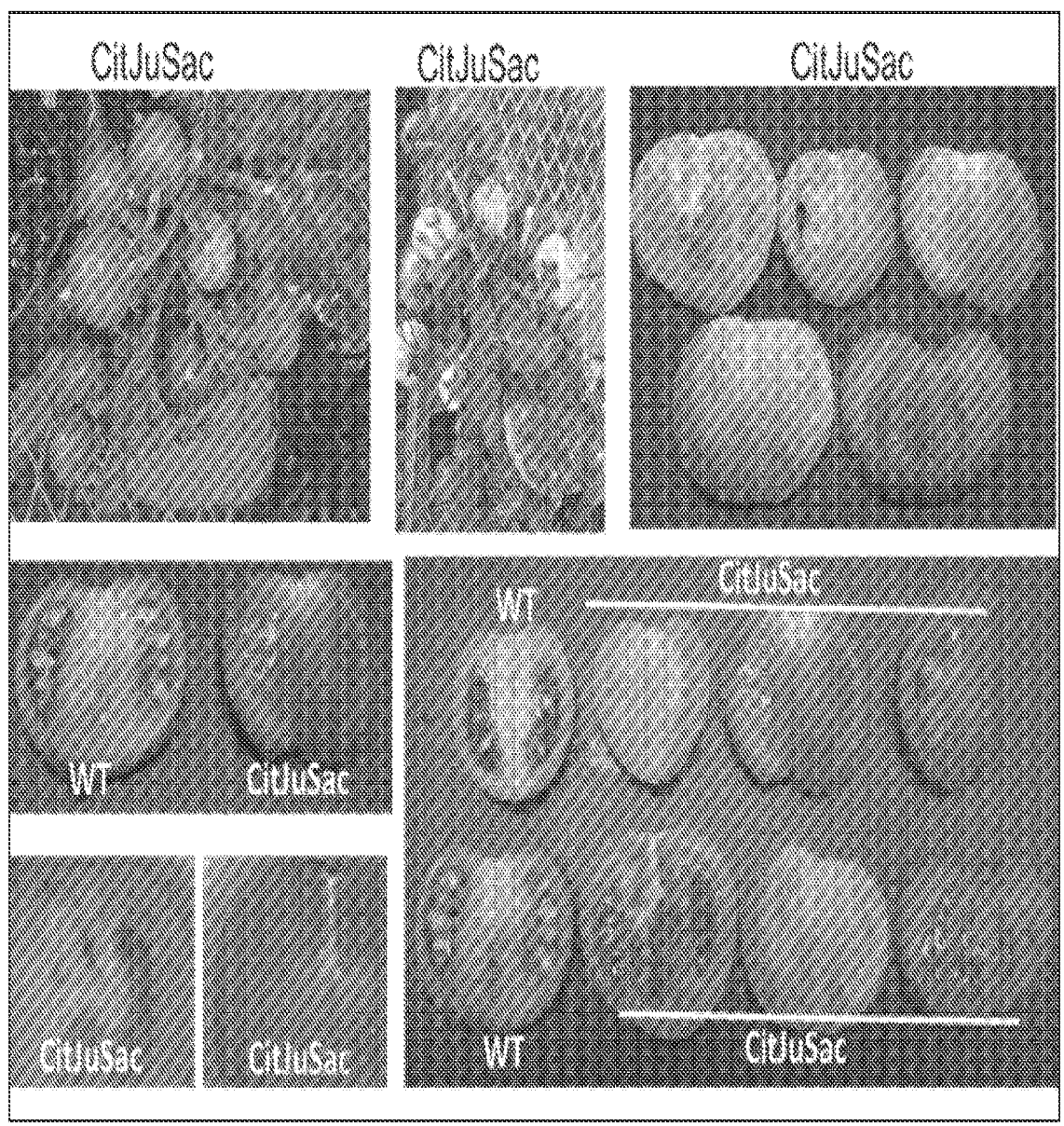
FIG. 6 shows the seedless fruit phenotype in the transgenic CitJuSacp tomato plants as compared to wild type.
Figure 7:
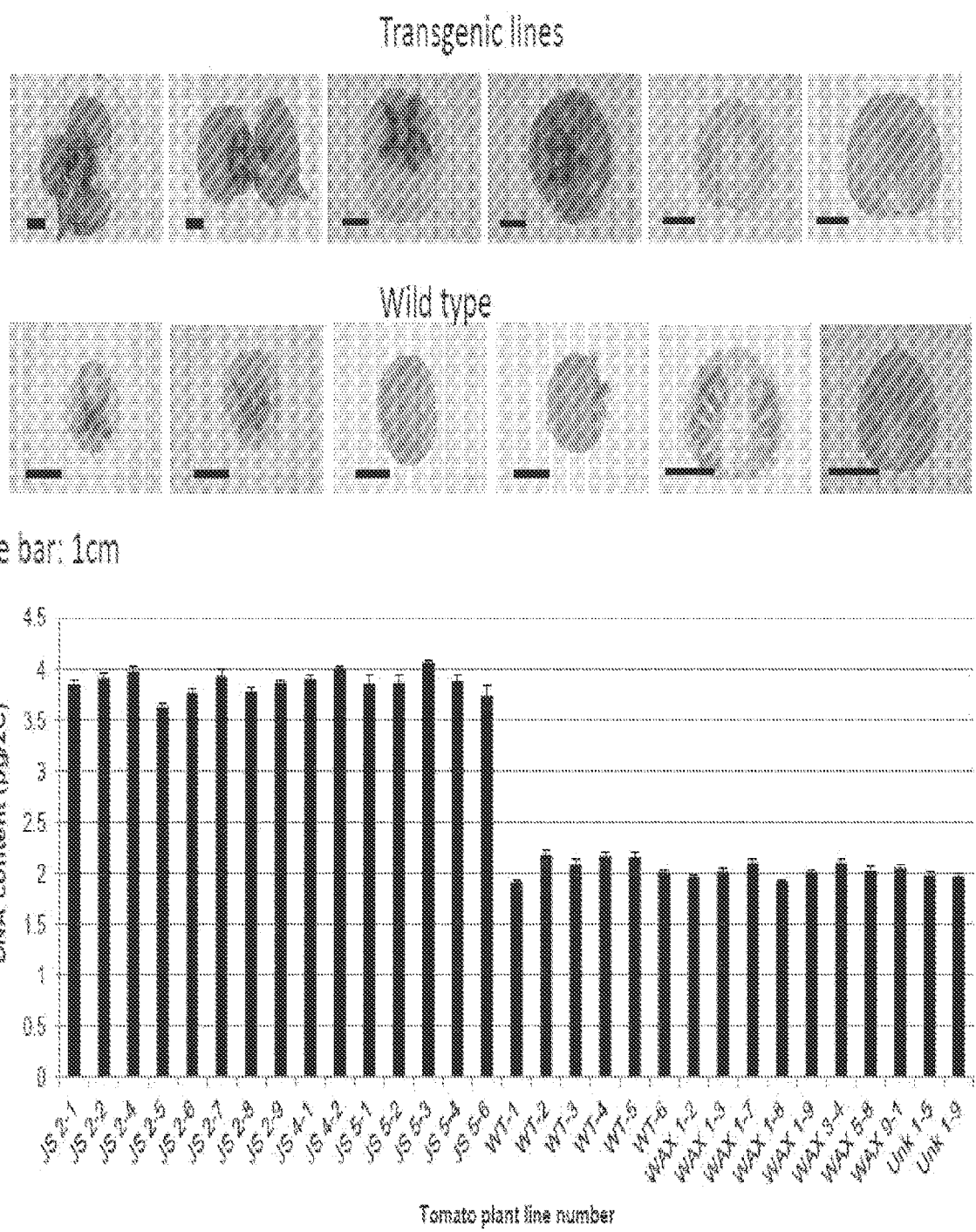
FIG. 7 shows the comparison of fruit phenotype (upper panel) and comparison of genome DNA content (lower panel) between the transgenic CitJuSacp tomato lines and wild type.

Seed and fruit development are intimately related processes controlled by internal signals and environmental cues. Interestingly, the CitJuSacp transgenic lines generated seedless fruits even though the fruit development was similar to that of WT. The CitJuSacp lines' fruits had more biomass and were larger in size compared to WT. Compared to WT, the transgenic tomato lines either did not develop seeds or developed small non-viable seeds (FIG. 6 and FIG. 7). However, upon repeating transgenic production using this same construct in *Arabidopsis* and tobacco, the seedless phenotype was not detected. The seedless nature of the CitJuSacp tomato lines may be a very specific interaction between the CitJuSacp and the tomato genome that will require further study.

A genetic method for obtaining seedless fruits is valuable for the market only if fruit quality and productivity are not curtailed. In this case, both the quality and productivity were not compromised. Furthermore, these plants did not display any vegetative or reproductive alterations except for the lack of seeds. Therefore, the seedless fruit phenotype observed in the CitJuSacp transgenic lines has valuable implications in developing seedless fruit cultivars. The nucleotide sequence of the CitJuSacp is included herein as SEQ ID NO: 4 or a certain degree of sequence identity to SEQ ID NO: 4.

Transgene Copy Number Characterization

T1 plants were germinated on kanamycin-containing media and then transferred to soil. Droplet digital PCR (ddPCR) was conducted to identify low-copy lines in T1 generation (Table 8 and Table 9). The ddPCR assay can determine transgene copy number in independent events, as well as can be used to distinguish hemizygous lines from their homozygous siblings. The tomato single-copy gene prosystemin (McGurl et al., 1992) was previously utilized in qPCR experiments as an endogenous reference for transgene copy number measurement (Collier et al., 2017). Five independent transgenic events were examined. Hemizygous and homozygous individuals were confidently identified that carry single-copy nptII transgene insertions. For each candidate promoter construct, three representative lines were selected based on ddPCR transgene copy number results and initial GUS analysis in T0 generation for further study (Table 8), ddPCR results indicate that the CitJuSacp lines only had a half or single copy of the transgene in all transgenic plants produced. These results were confirmed by the COT analysis for total genomic content when compared against WT (FIG. 7), which suggested that the CitJuSacp lines had undergone complete genome duplication.

TABLE 8

Transgene copy number of the candidate promoter transgenic tomato plants

| CitWAXp Transgenic Plants | | CitUNKp Transgenic Plants | | CitSEPp Transgenic Plants | | PfeMybAp Transgenic Plants | | CitJuSacp Transgenic Plants | | Wild type control | |
|---|---|---|---|---|---|---|---|---|---|---|---|
| Line | Copy | Line | Copy | Line | Copy | Line | Copy | Line | Copy | Line | Copy |
| WAX1-1 | 3.00 | UNK2-1 | 0.98 | SEP4-1 | 1.94 | Pfe1-1 | 0.98 | JS2-1 | 0.51 | WT1-1 | 0.02 |
| WAX1-2 | 5.91 | UNK2-2 | 1.98 | SEP4-2 | 0.97 | Pfe1-3 | 1.01 | JS2-4 | 0.98 | WT1-2 | 0.03 |
| WAX1-3 | 2.96 | UNK2-3 | 1.01 | SEP4-3 | 1.01 | Pfe1-4 | 2.01 | JS2-6 | 0.51 | | |
| WAX1-4 | 5.00 | UNK2-4 | 1.94 | SEP4-5 | 1.00 | Pfe1-5 | 0.97 | JS2-7 | 0.97 | | |
| WAX1-7 | 2.09 | UNK2-5 | 1.01 | SEP4-6 | 1.00 | Pfe1-6 | 1.95 | JS2-8 | 0.94 | | |
| WAX3-1 | 2.92 | UNK3-1 | 2.04 | SEP8-1 | 4.98 | Pfe2-2 | 1.00 | JS2-9 | 1.01 | | |
| WAX3-3 | 6.10 | UNK3-2 | 1.03 | SEP8-2 | 5.05 | Pfe2-3 | 1.94 | JS4-1 | 1.01 | | |
| WAX3-5 | 5.00 | UNK3-3 | 0.97 | SEP8-4 | 1.92 | Pfe2-4 | 0.99 | JS4-2 | 0.50 | | |
| WAX3-6 | 2.90 | UNK3-4 | 1.01 | SEP8-5 | 2.00 | Pfe2-5 | 1.96 | JS5-1 | 0.52 | | |
| WAX3-7 | 2.94 | UNK3-5 | 2.02 | SEP8-6 | 5.09 | Pfe2-6 | 2.02 | JS5-2 | 0.53 | | |
| WAX5-1 | 6.04 | UNK4-1 | 1.00 | SEP10-1 | 1.01 | Pfe9-1 | 1.90 | JS5-3 | 0.49 | | |
| WAX5-2 | 2.27 | UNK4-2 | 1.00 | SEP10-2 | 1.03 | Pfe9-3 | 0.98 | JS5-4 | 0.51 | | |
| WAX5-3 | 3.05 | UNK4-3 | 1.99 | SEP10-3 | 1.90 | Pfe9-4 | 1.92 | JS5-6 | 0.02 | | |
| WAX5-4 | 1.04 | UNK4-4 | 2.01 | SEP10-4 | 1.91 | Pfe9-5 | 1.00 | JS7-1 | 1.90 | | |
| WAX5-9 | 2.82 | UNK4-5 | 1.00 | SEP10-6 | 1.04 | Pfe9-6 | 0.99 | | | | |

TABLE 9

Transgene copy number of the control promoter transgenic tomato plants

| PGp Transgenic Plants | | E8p Transgenic Plants | | 35Sp Transgenic Plants | |
|---|---|---|---|---|---|
| Line | Copy | Line | Copy | Line | Copy |
| PG1-1 | 0.97 | E81-1 | 13.80 | 35S1-3 | 0.95 |
| PG1-2 | 1.89 | E81-2 | 10.98 | 35S1-4 | 0.91 |
| PG1-3 | 0.95 | E81-5 | 13.90 | 35S1-6 | 0.92 |

TABLE 9-continued

Transgene copy number of the control promoter transgenic tomato plants

| PGp Transgenic Plants | | E8p Transgenic Plants | | 35Sp Transgenic Plants | |
|---|---|---|---|---|---|
| Line | Copy | Line | Copy | Line | Copy |
| PG1-4 | 0.94 | E81-6 | 18.10 | 35S1-7 | 1.04 |
| PG1-5 | 1.92 | E81-9 | 10.80 | 35S1-8 | 1.97 |
| PG3-3 | 2.81 | E82-3 | 2.84 | 35S2-2 | 0.90 |
| PG3-4 | 0.91 | E82-4 | 5.07 | 35S2-3 | 1.97 |
| PG3-5 | 2.82 | E82-7 | 3.02 | 35S2-4 | 0.90 |
| PG3-6 | 1.91 | E82-8 | 5.90 | 35S2-6 | 0.92 |
| PG3-8 | 2.16 | E84-1 | 2.04 | 35S2-8 | 0.97 |
| PG6-4 | 1.03 | E84-2 | 2.04 | 35S3-1 | 0.92 |
| PG6-5 | 1.07 | E84-4 | 1.99 | 35S3-4 | 1.88 |
| PG6-6 | 1.06 | E84-3 | 1.00 | 35S3-5 | 1.85 |
| PG6-7 | 1.09 | E86-1 | 13.30 | 35S3-6 | 1.89 |
| PG6-8 | 1.09 | E86-2 | 14.20 | 35S3-7 | 2.07 |
| PG7-1 | 1.00 | E86-4 | 11.20 | | |
| PG7-2 | 1.10 | E86-5 | 11.80 | | |
| PG7-3 | 1.90 | E86-6 | 15.10 | | |
| PG7-4 | 1.00 | | | | |
| PG7-5 | 1.04 | | | | |
| PG8-2 | 12.20 | | | | |
| PG8-3 | 11.80 | | | | |
| PG8-4 | 12.00 | | | | |
| PG8-6 | 13.10 | | | | |
| PG8-7 | 11.09 | | | | |

Qualitative Analysis of Promoter Activity in Transgenic Tomato

Figure 8A:
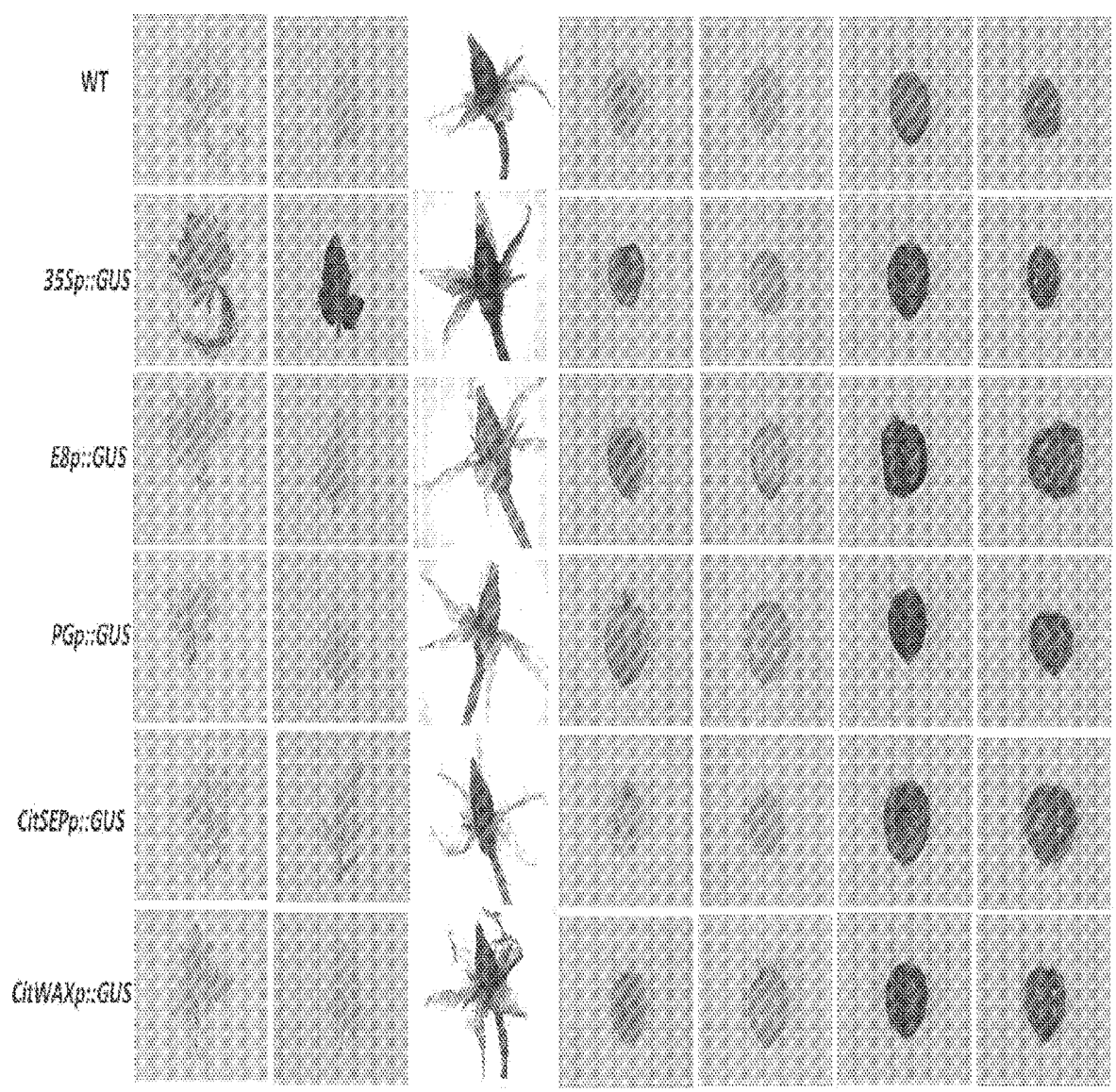
FIGS. 8A-8B show GUS staining on whole seedling (column 1), mature leaf (column 2), flower (column 3), unripe fruit cross section (column 4), unripe fruit exterior (column 5), ripe fruit cross section (column 6), and ripe fruit exterior (column 7) in wild type tomato versus in transgenic tomato lines transformed with the Promoter::GUS constructs (35Sp::GUS, E8p::GUS, PGp::GUS, CitSEPp::GUS and CitWAXp::GUS constructs in FIG. 8A; CitUNKp:: GUS, CitJuSacp::GUS and PfeMybAp::GUS constructs in FIG. 8B). Representative plant tissues are from wild type tomato (cultivar Micro-Tom) or transgenic plants after one month of cultivation in the greenhouse.
Figure 8B:
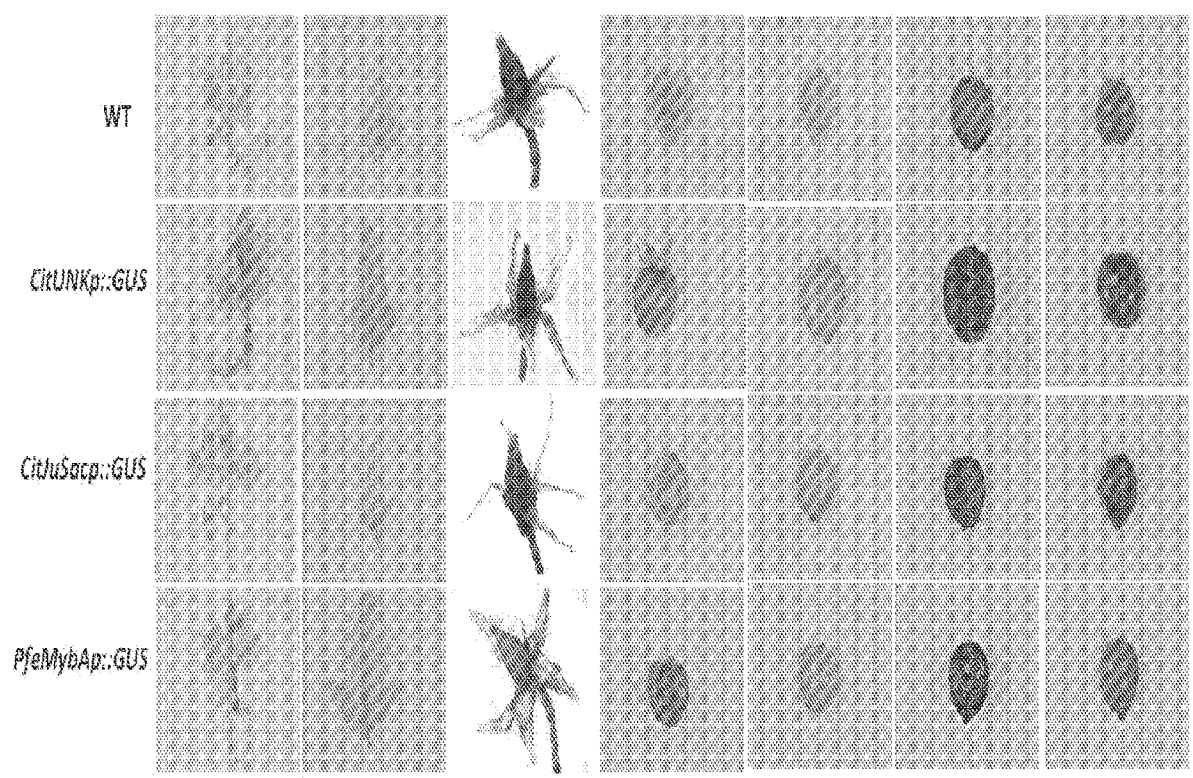

Qualitative analysis of promoter activity was conducted by comparing intensity of GUS staining between promoter transgenic lines and controls. Images showing GUS staining in various vegetative and reproductive tissues are presented in FIGS. 8A-8B. A summary of the tissue-specific expression patterns for the candidate promoters are shown in Table 10.

TABLE 10

Summary of qualitative GUS analysis in transgenic tomato

| Promoter::GUS | Seedling | Leaf | Stem | Root | Flower | Immature fruit | Mature fruit |
|---|---|---|---|---|---|---|---|
| 35Sp::GUS | Yes | Yes | Yes | Yes | Yes | Yes | Yes |
| E8p::GUS | Yes (faintly leaky sometimes) | Yes (faintly leaky sometimes) | No | Yes (leaky) | Yes (leaky) | Yes | Yes |
| PGp:GUS | Yes (faintly leaky sometimes) | No | No | No | No | Yes, weak | Yes, strong |
| CitSEPp::GUS | No | No | No | No | No | No | Yes (most strong in seeds) |
| CitWAXp::GUS | Yes (weak, mostly in leaves) | Yes (faintly leaky sometimes) | No | No | Yes | Yes | Yes |
| CitUNKp::GUS | Yes | Yes | Yes (leaky) | Yes (leaky) | Yes (leaky) | Yes | Yes |
| CitJuSacp::GUS | Yes (leaky sometimes) | Yes (faintly leaky sometimes) | No | No | Yes (leaky) | Yes | Yes |
| PfeMybAp::GUS | Yes (leaky sometimes) | Yes (leaky in midrib) | No | No | Yes | Yes | Yes |

As expected, WT plants did not display any GUS staining in either vegetative or reproductive tissues, while the positive control transgenic lines transformed with 35Sp promoter fused to reporter gene showed GUS staining in all tissues. The known fruit-specific tomato E8p promoter showed strong activity in both unripe and ripe fruits, leaky activity in flower, and leaky activity in seedling and mature leaf. Another known fruit-specific PGp promoter from tomato showed minor leaky activity in seedling but no activity in mature leaf, root or flower. However, activity of PGp promoter was very strong in ripe fruit compared to that in young immature fruit, presumably due to the involvement of the PG gene in fruit ripening process.

CitSEPp transgenic lines showed no GUS expression in leaf and petiole, no expression in root and flower, no expression in mature leaf, very faint expression in young immature fruit, but strong expression in mature fruit. The expression in the fruit was strongest in the mucosal sac surrounding the seeds, followed by locular tissue, pericarp tissue and placental tissue.

CitWAXp transgenic lines showed some weak leaky GUS expression in leaf and flower, no expression in the root and mature leaf, but strong expression in both immature and immature fruits.

CitUNKp transgenic lines showed weak GUS expression in seedling and mature leaf, and leaky expression in stem, root, and flower. Immature fruit showed stronger expression than mature fruit. The expression in the fruit was strongest in the outer epidermis and seeds, followed by locular tissue, pericarp tissue and placental tissue.

CitJuSacp transgenic lines showed some weak faint GUS expression in seedling, no expression in mature leaf, no expression in root and flower but strong expression in young immature fruit and ripe fruit. The expression in the fruit was strongest in the locular tissue, pericarp tissue, and placental tissues in the ripe fruit. Seed development was severely affected in the transgenic lines (seedless).

PfeMybAp transgenic lines showed an interesting pattern of GUS expression in leave that had blue stains in the mid-rib and the base of the leaf, while the root did not show any blue staining. The flower was mostly stained in the petals. Both unripe and ripe fruits, however, had very strong GUS expression throughout the fruit.

Quantitative Analysis of Promoter Activity

To confirm the results of the qualitative analysis, quantitative analysis of promoter activity was conducted using the quantitative GUS expression assay (Jefferson et al., 1987. Weigel and Glazebrook. 2002, and Blázquez, 2007). Quantitative GUS expression assay was performed in leaf, immature fruit, and ripe fruit of three representative transgenic tomato lines for each Promoter::GUS construct.

Results of the quantitative GUS expression assay further confirmed the promoter activity patterns concluded from the qualitative analysis. A summary of the quantitative GUS expression results is shown in FIGS. 9A-9D. WT plants did not display GUS staining in any tissue. Lines transformed with construct of positive control 35S promoter fused to reporter gene showed high level of GUS expression in all tissues as expected. CitSEPp transgenic lines showed GUS expression only in ripe fruits. CitWAXp transgenic lines showed some expression in leaves and higher expression in ripe fruits. CitUNKp transgenic lines showed high levels of expression in leaves compared to WT. Expression was also detected in both unripe and ripe fruits. CitJuSacp transgenic lines showed more fruit preferential expression compared to WT. PfeMybAp transgenic lines showed fruit preferential expression compared to leaves.

Figure 9A:
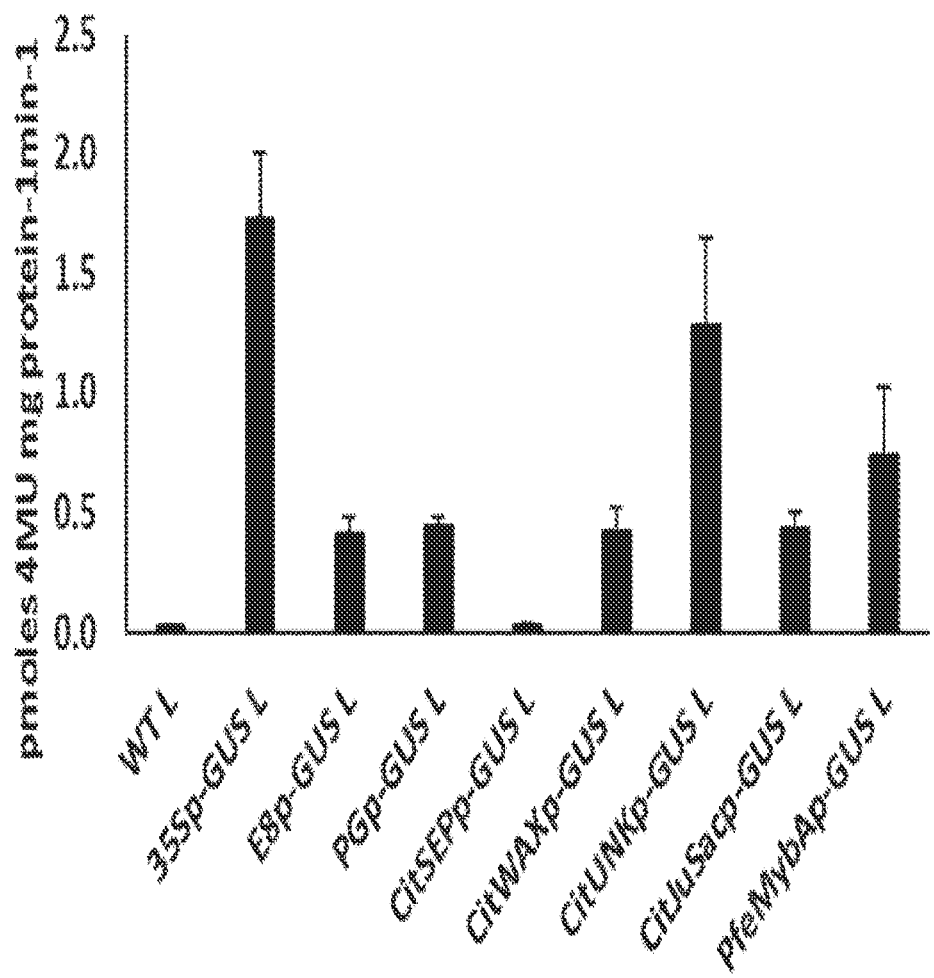
FIGS. 9A-9D show the quantitative GUS analysis on leaf (L), unripe fruit (UR) and ripe fruit (R) in representative transgenic tomato lines transformed with the Promoter:: GUS constructs as compared to wild type.
Figure 9B:
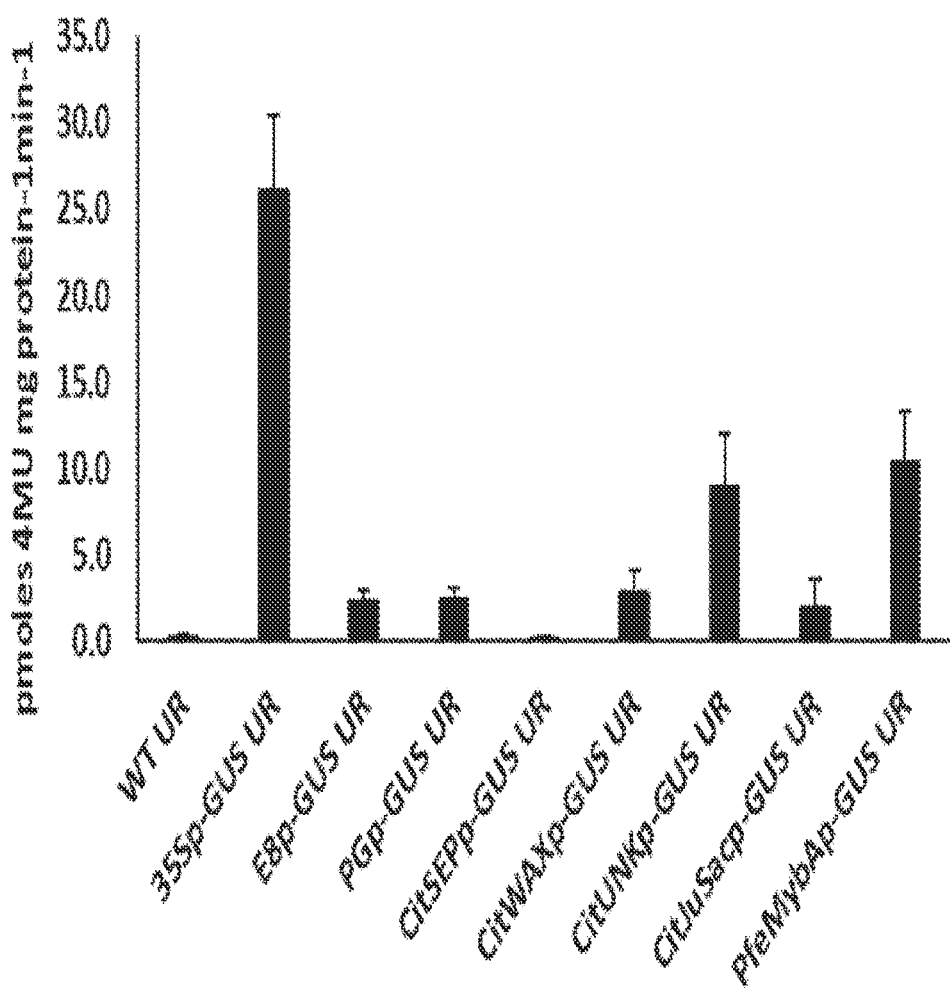
Figure 9C:
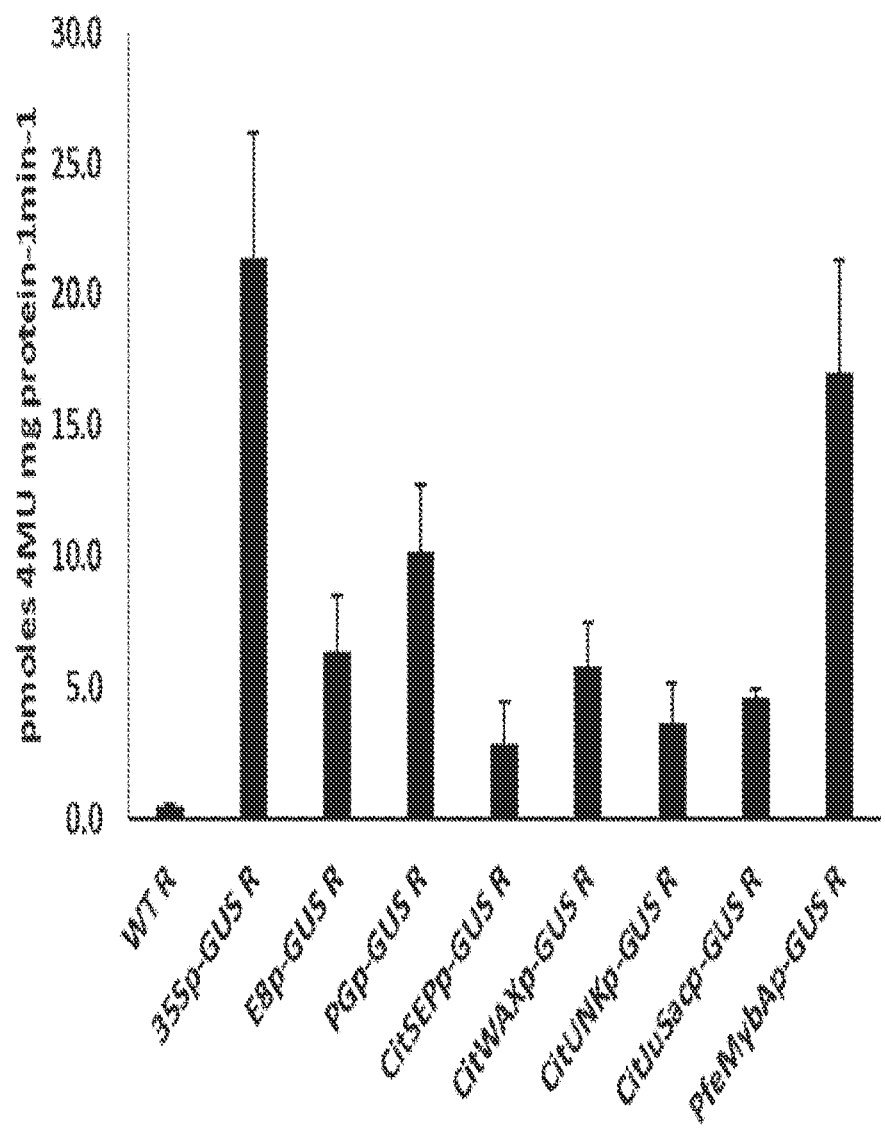
Figure 9D:
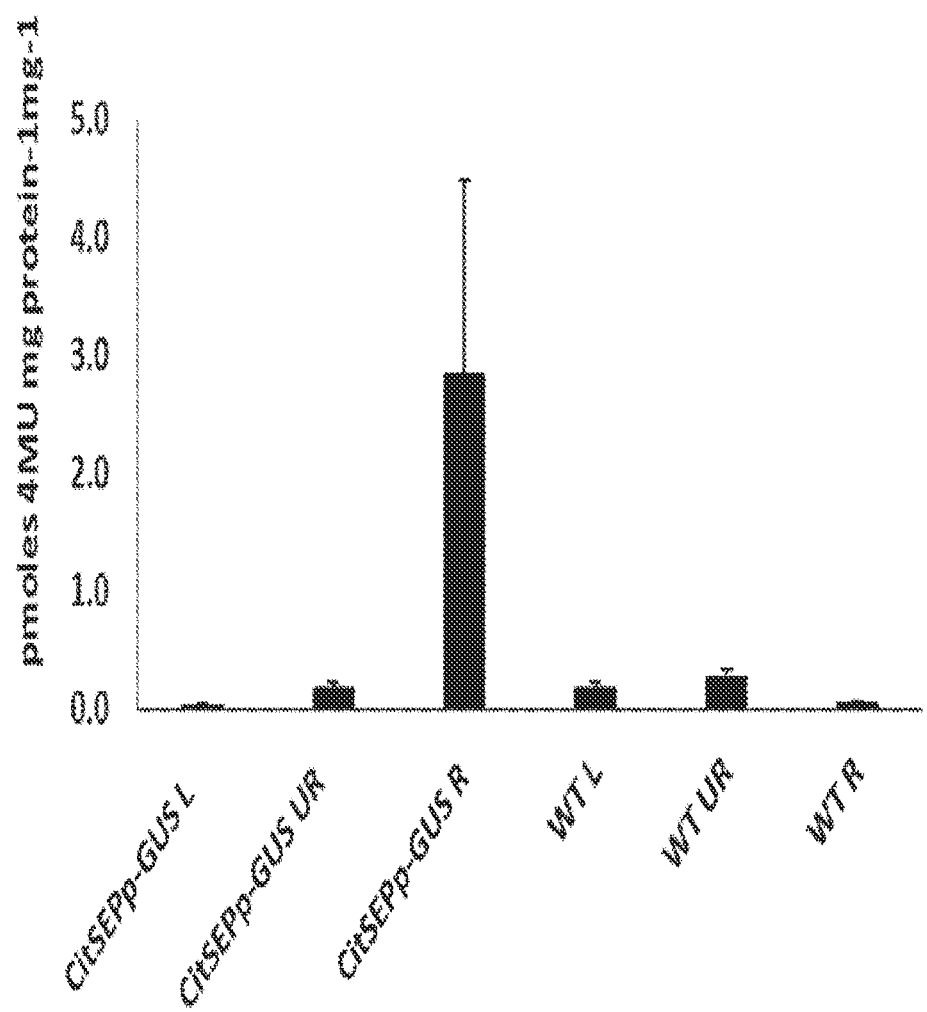

From the results, the citrus candidate promoter CitSEPp had the best fruit-specific expression pattern in tomato. Among all the candidate citrus promoters tested, CitSEPp was the only one showing GUS expression in the seeds and surrounding tomato pulp in ripe fruits only (FIGS. 8A-8B and FIGS. 9A-9D). Specifically. CitSEPp in tomato showed no GUS expression in leaves and petiole, no expression in roots and flowers, no expression in mature leaves, very faint expression in young immature fruits but strong expression in mature fruits. The expression in the fruit was strongest in the seeds followed by locular tissue, pericarp and placental tissues. The qualitative analysis correlates with the quantitative data as shown in the graph. Compared to WT, GUS activity was detected only in the ripe fruits of the CitSEPp::GUS lines (FIG. 9D).

Figure 10:
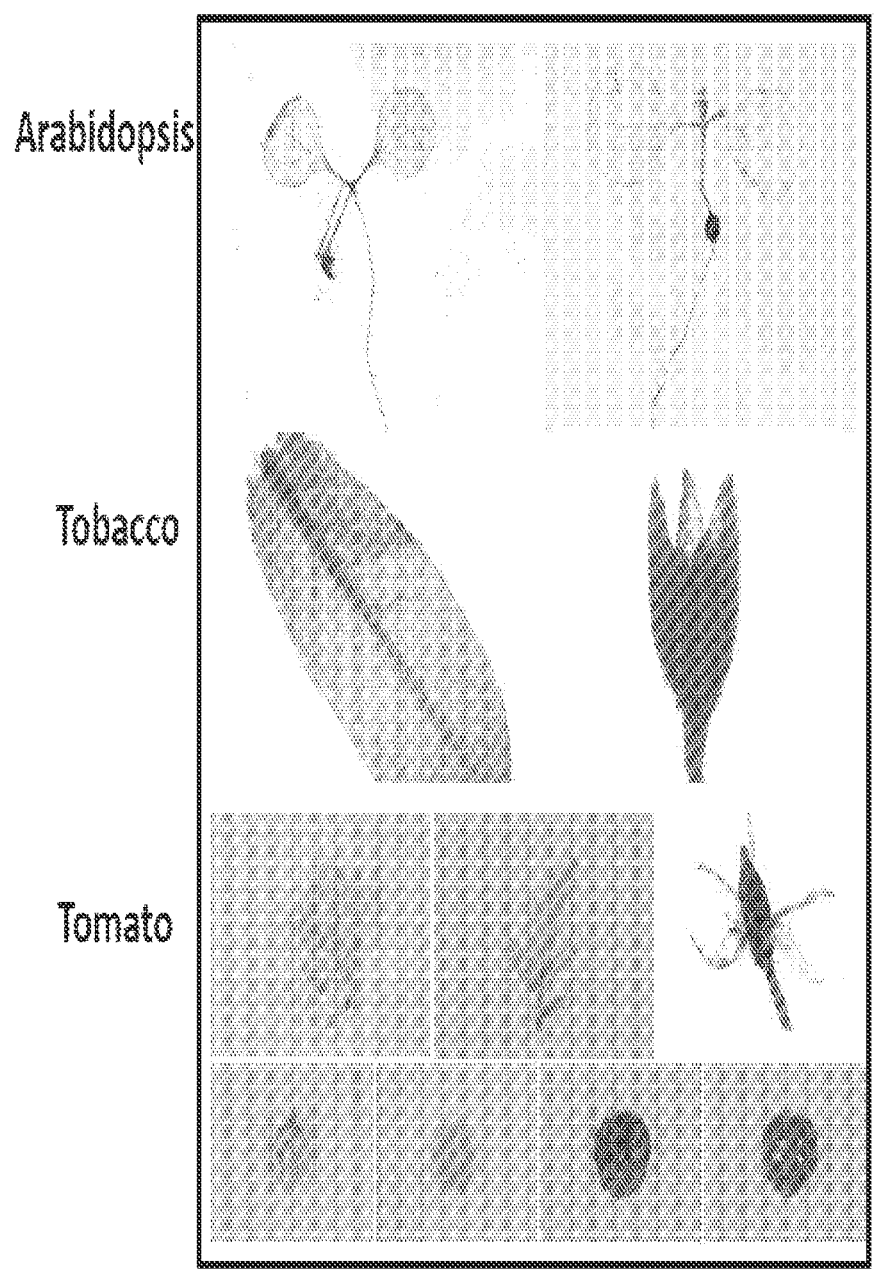
FIG. 10 shows the GUS staining results in transgenic *Arabidopsis*, tobacco and tomato plants transformed with the CitSEPp::GUS construct.

Based on the above analysis, transgenic Arabidopsis and tobacco transgenic lines were generated. FIG. 10 shows GUS staining of T1 transgenic lines on Arabidopsis seedling (top two images, no staining) and tobacco leaf and flower (middle two images, no staining), as compared to tomato (bottom images, staining in fruit only, as previously presented in FIG. 8A). The results confirmed that CitSEPp has a high fruit-specific expression pattern in Arabidopsis and tobacco as in tomato.

Conclusion

Taken together, the results indicate that the candidate promoters are functional in driving gene expression in plants with strong fruit preference, where the citrus candidate promoter CitSEPp has the strongest fruit-specific expression pattern in tomato. Additionally, it was found that CitJuSacp transgenic lines generated seedless fruits with otherwise normal development, which provides significant implications in the development of seedless fruit varieties.

Example 5: Modification of Anthocyanin Accumulation Using Fruit-Specific Promoters The following example illustrates the use of the candidate promoters in modifying anthocyanin accumulation in fruit. Plants produce a group of metabolites, such as flavonoids, that belong to a group of plant natural products, playing an important role in protection against various stresses. Anthocyanin forms the largest sub-class of flavonoids conferring different colors in fruits and flowers. Increased anthocyanin content is a desired commercial fruit trait. The objective of this study was to use the identified fruit-specific promoters for manipulation of the anthocyanin metabolic pathway to enable the generation of new plant varieties with improved fruit quality.

Methods and Materials

Molecular Constructs

The fruit-specific promoters, together with the control promoter (i.e. tomato E8 promoter E8p), were PCR amplified, digested, and cloned into pCTAG6-GUSPlus vector (deposited in GenBank at NCBI, accession number MG836292). For transgenic Arabidopsis and tobacco plants, the Promoter::MoroMybA constructs were inserted into the pCTAG6-GUSPlus vector backbone for transformation. For transgenic citrus plants, in addition to the Promoter::MoroMybA constructs, a Nosp::AtFT::NosT construct was inserted into the pCTAG6-GUSPlus vector backbone at the PspOM1 site for transformation in order to shorten the flowering time of the transgenic citrus plants. Nosp has a nucleotide sequence of SEQ ID NO: 21. AtFT has a nucleotide sequence of SEQ ID NO: 22. NosT has a nucleotide sequence of SEQ ID NO: 23. A diagram showing the molecular constructs is presented in FIG. 11.

Transgenic *Arabidopsis* Plants

*Agrobacterium tumefaciens* strain GV3101 was used for transformation of *Arabidopsis* ecotype Ler by the floral dip method (Clough and Bent 1998) that is modified by adding 0.01% Silwet L-77 (Lehle Seeds, Round Rock. Tex.) to the infiltration medium. Primary transformants were selected on MS medium (Sigma. St. Louis, Mo.). 1% sucrose, 0.7% agar with 20 µg/ml hygromycin or 50 µg/ml kanamycin as needed for 10 days prior to cultivation in soil.

Transgenic Tobacco Plants

Tobacco (*Nicotiana tabacum* L. cv. Petit Havana SR1) was used for leaf disc transformation (Horsch and Klee 1986). *Agrobacterium* cells were grown to an optical density of 1.0 at 600 nm (OD600), and a final suspension at OD600 of 0.5 was used for plant infection. Young, healthy green leaves were cut into pieces approximately 10 mm in length, and the leaf segments were incubated in an *Agrobacterium* suspension for 30 minutes. The leaf segments were then blotted dry on sterile filter paper for 5 min and placed onto MS co-cultivation medium (Sigma. St. Louis, Mo.) in sterile Petri dishes and kept in the growth chamber at 25° C. for three days in the dark. The infected leaf explants were then transferred to regeneration/selection medium (24° C. with 16 h of light and 8 h of dark at 20° C.). Primary tobacco transformants were selected on MS medium, with 100 mg/mL kanamycin. After 2-3 weeks, the infected leaf explants were transferred onto fresh regeneration/selection media. Separate shoots from explants were excised carefully and transferred into plant culture dishes containing rooting medium. Rooted plants were grown in Sunshine potting mix (Sun Gro Horticulture Ltd. Agawam, Mass.) in the greenhouse with 16 h of light at 150 photosynthetic photon flux density (µmol photons m-2 s-1) at 23° C. and 8 h of dark at 20° C. with 70% humidity. Twenty kanamycin resistant lines were obtained from the $T_0$ generation for each construct. $T_1$ seeds were collected and selected on an MS plate supplemented with kanamycin 100 mg/mL.

Transgenic Citrus Plants

The transgenic Carrizo citrange and Mexican lime citrus lines were generated using epicotyl explants protocol as previously described by de Oliveira et al., *Plant Cell Rep* (2009) 28:387-395, and de Oliveira et al., *HortTechnology* (2016) 26(3), 278-286.

Semi-Quantitative PCR (Reverse Transcription-PCR, RT-PCR)

Leaf tissues were collected from plants grown in greenhouse and homogenized using the MagNA Lyser instrument (Roche Life Science). RNA was extracted using the sample preparation kit Direct-zol RNA Miniprep Plus (Zymo Research, catalog number R2071). cDNA synthesis was performed using the Revert Aid H minus First Strand cDNA Synthesis Kit for 100 rkns (Thermo Fisher Scientific, catalog number K1632). PCR assay for gene of interest (e.g. AtFT) was performed using CitEF1a as the internal control. PCR products were loaded into 1.2% agarose gel for gel electrophoresis. Gel image was analyzed using the image processing software ImageJ (Schneider et al., *Nature methods* (2012) 9(7): 671:675). The resulting data of gel band intensity was used for calculating the relative expression of the gene of interest compared to the internal control.

Droplet Digital PCR

Genomic DNA was extracted by grinding a 1-cm$^2$ piece of tobacco leaf in 400 µL of buffer (200 mm Tris-HCl pH 7.8, 250 mm NaCl. 25 mm EDTA. 0.5% SDS). After centrifugation and isopropanol precipitation, the pellet was washed with 70% ethanol and resuspended in 50 µL of water with 1 mM RNase A. PCR amplification was performed using 2 µL of genomic DNA in reactions with a total volume of 25 µL. Presence of the transgene was confirmed by PCR using transgene specific primers, including NptII_F2819 with a nucleotide sequence of 5'-TTGCCGAATATCATGGTGGA-3' (SEQ ID NO: 24). NptII_R2931 with a nucleotide sequence of 5'-TCAGCAATATCACGGGTAGC-3' (SEQ ID NO: 25), SISys_Probe with a nucleotide sequence of 5'-TGCAACATCCTTCTTTCTFCTCGTG-3' (SEQ ID NO: 26), SiSys_F with a nucleotide sequence of 5'-GCAATAT-CAAGAGCCCCGTC-3' (SEQ ID NO: 27), SISys_R with a nucleotide sequence of 5'-ATGTGTGCTAAGCGCTCC-3' (SEQ ID NO: 28), codA_ddPCR_F1 with a nucleotide sequence of 5'-CGGGCAGATTAACGATGG-3' (SEQ ID NO: 29), codA_ddPCR_R1 with a nucleotide sequence of 5'-CGCATCAAACCCATTTTCAG-3' (SEQ ID NO: 30), and codA Probe with a nucleotide sequence of 5'-CGGCAG-GATAATCAGGTTGGC-3' (SEQ ID NO: 31). Droplet digital PCR (ddPCR) was performed following the methods in Collier et al., 2017.

Results

Figure 12:
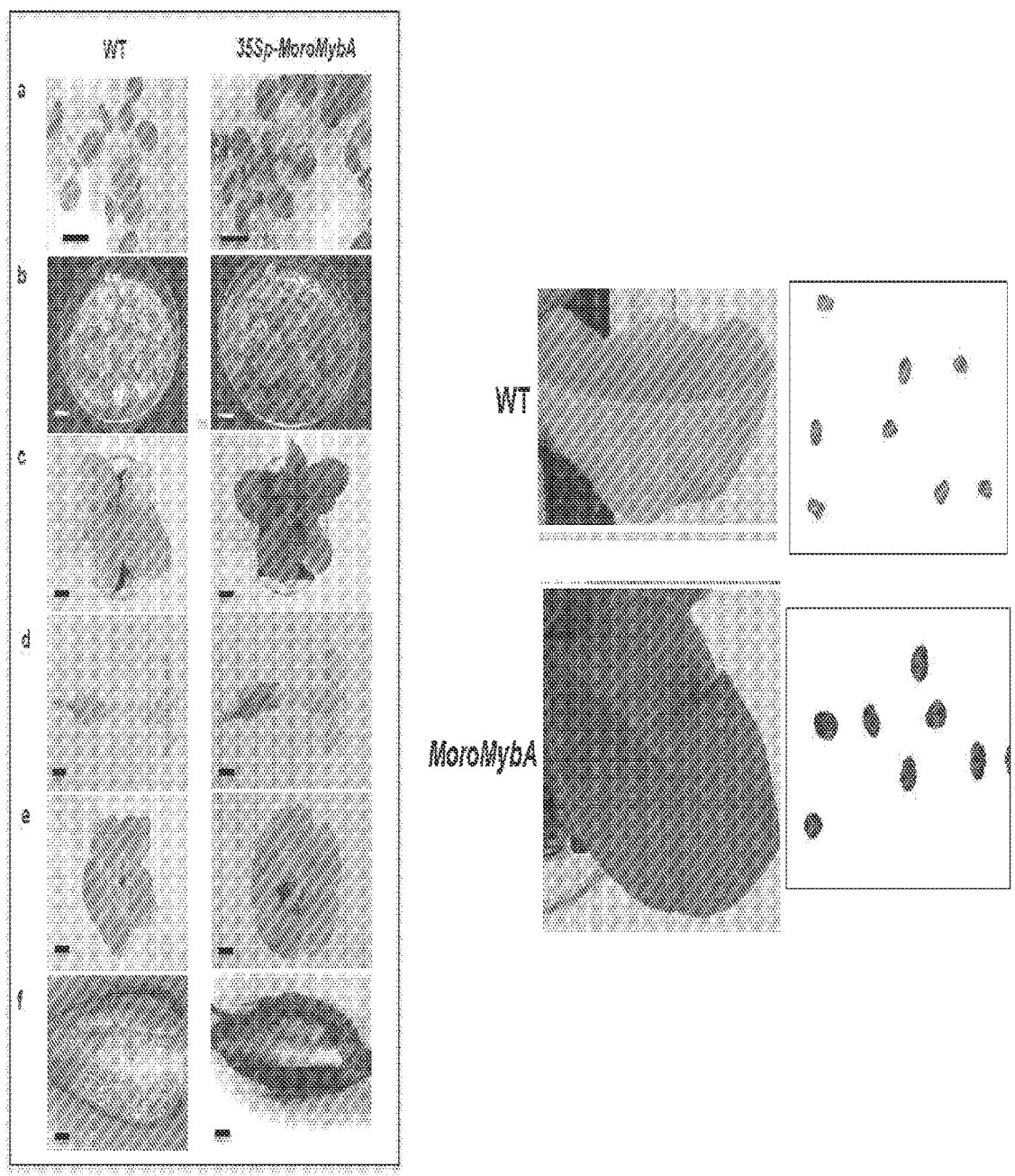
FIG. 12 shows the phenotypes of transgenic tobacco plants transformed with the 35Sp::MoroMybA construct as compared to wild type.

The MybA gene is the key player activating the anthocyanin metabolic pathway. The MoroMybA is a synthetic version of the citrus CsRuby (Butelli et al., 2012) coding sequence. MoroMybA encodes a 262-amino acid protein and was used for transgenic citrus production and MybA transgene studies as described in Dasgupta et al., 2017. In addition, the 35Sp-MoroMybA construct was shown to be functional in tobacco (FIG. 12).

Based on the promoter expression analyses in the preceding examples, three citrus fruit-specific promoters (Cit-WAXp, CitUNKp, CitJuSacp) were chosen and fused to MoroMybA gene to make an all-citrus transgene construct. In addition, the tomato control promoter E8p and candidate plum promoter PfeMybAp were fused to MoroMybA for stable transgenic testing. These Promoter::MoroMybA (MM) constructs form a novel molecular toolbox that facilitates the expression of traits specifically within fruit tissue of desired transgenic plants.

For citrus transgenic plants, there is an additional consideration. Most citrus trees need 5-15 years to begin flowering and fruiting. The long juvenile phase delays regular fruit production for years. Alternatively, early flowering has been achieved in transgenic trees, including citrus, by constitutively over-expressing flower meristem identity genes. FLOWERING LOCUS T gene (FM) is a key regulator of the flowering transition. It has already been shown that the FT overexpression system induces an extremely early fruiting phenotype and two fruiting cycles per year in sweet orange plants (Pons et al., 2013). Considering the above facts, for citrus transgenic plant generation, the *Arabidopsis* FT gene (AtFT) was added into the construct to reduce the flowering time period and quickly assess citrus fruits accumulating anthocyanin.

Phenotypic Analysis of Anthocyanin Accumulation in Transgenic *Arabidopsis* Lines Selected Promoter::MoroMybA constructs without the AtFT gene were used for *Arabidopsis* floral dip transformation. A total of 12-15 independent T1 kanamycin positive lines were generated for each construct and were analyzed for the anthocyanin accumulation phenotype. For each construct, three representative T1 lines were checked for heritability of phenotype in T2 generation.

Figure 13:
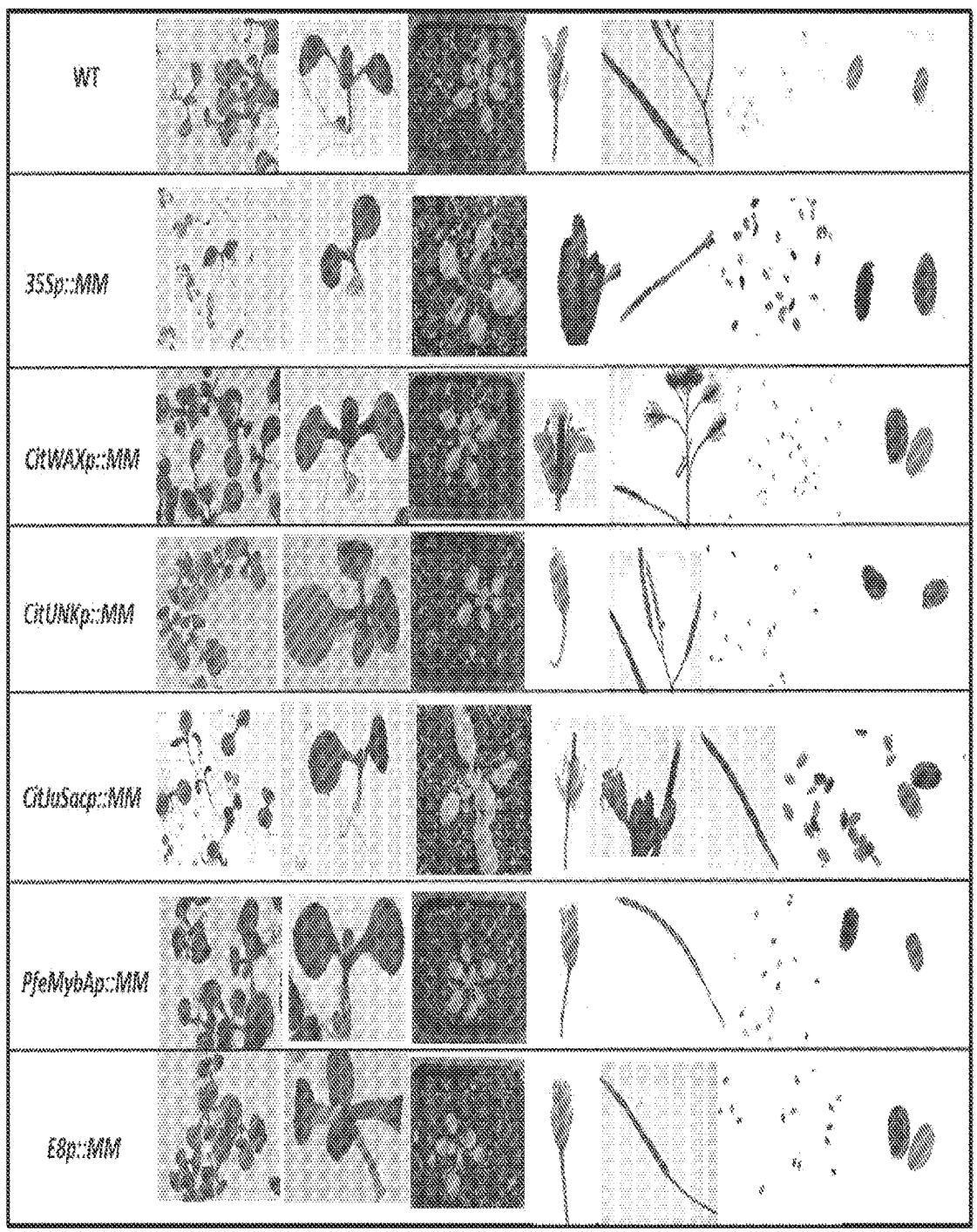
FIG. 13 shows the phenotypes of transgenic *Arabidopsis* plants transformed with the Promoter::MoroMybA constructs as compared to wild type.

Results showed that WT *Arabidopsis* lines did not show any anthocyanin accumulation whereas 35Sp::MoroMybA showed anthocyanin accumulation as expected in seeds, seedlings, young leaves, flowers and siliques. CitWAXp::MoroMybA and CitJuSacp::MoroMybA transgenic *Arabidopsis* lines showed anthocyanin accumulation in germinating seedlings, flowers, siliques and seeds but not in matured leaves and stems. Anthocyanin was not detected in any vegetative tissue of CitUNKp and PfeMybAp transgenic lines. However, these lines accumulated anthocyanin in seeds only. Tomato fruit-specific promoter E8p was used as a positive control for this study to be fused to MoroMybA, and the resulting transgenic lines also showed anthocyanin accumulation only in seeds. A summary of the *Arabidopsis* anthocyanin accumulation analysis on a representative line for each construct is shown in FIG. 13.

Phenotypic Analysis of Anthocyanin Accumulation in Transgenic Tobacco Lines

Selected Promoter::MoroMybA constructs without AtFT gene were used for tobacco transformation. A total of 12-15 independent T0 kanamycin positive lines were generated for each construct and were analyzed for the anthocyanin accumulation phenotype. For each construct, three representative lines were checked for heritability of phenotype in T1 generation.

Expression of the 35Sp::MoroMybA construct in tobacco displayed a uniform and homogenously consistent light purplish coloration throughout the entire plant compared to WT. The specificity of expression conferred by the construct CitWAXp::MoroMybA was examined in several tissues and organs of the transgenic tobacco plants. Anthocyanin was not detected in the any vegetative tissue. Anthocyanin accumulation was detected in the seedpod outer layer as well as the seeds of transgenic tobacco lines, suggesting a highly fruit-specific expression pattern of the CitWAXp promoter.

The specificity of expression conferred by the construct CitUNKp::MoroMybA was examined in several tissues and organs of the transgenic tobacco plants. Anthocyanin was not detected in any vegetative tissue. Anthocyanin accumulation was only detected in the seeds of transgenic tobacco lines, suggesting a highly fruit specific expression pattern of the CitUNKp promoter. There was no expression on the outer seedpod cover. No accumulation was detected in vegetative tissues or flower.

The specificity of expression conferred by the construct CitJuSacp::MoroMybA was examined in several tissues and organs of the transgenic tobacco plants. Anthocyanin was not detected in any vegetative tissue. Anthocyanin accumulation was detected in stigma of flowers, seedpod outer and inner layer, as well as seeds of the transgenic tobacco lines.

For the PfeMybAp::MoroMybA lines, anthocyanin was detected in the young seeds in seedpod as well as in mature seeds. No accumulation of anthocyanin was detected in vegetative tissues or flower.

For the E8p::MoroMybA lines, anthocyanin was detected only in mature seeds. Accumulation of anthocyanin was not detected in vegetative tissues, flower or immature seeds.

Figure 14:
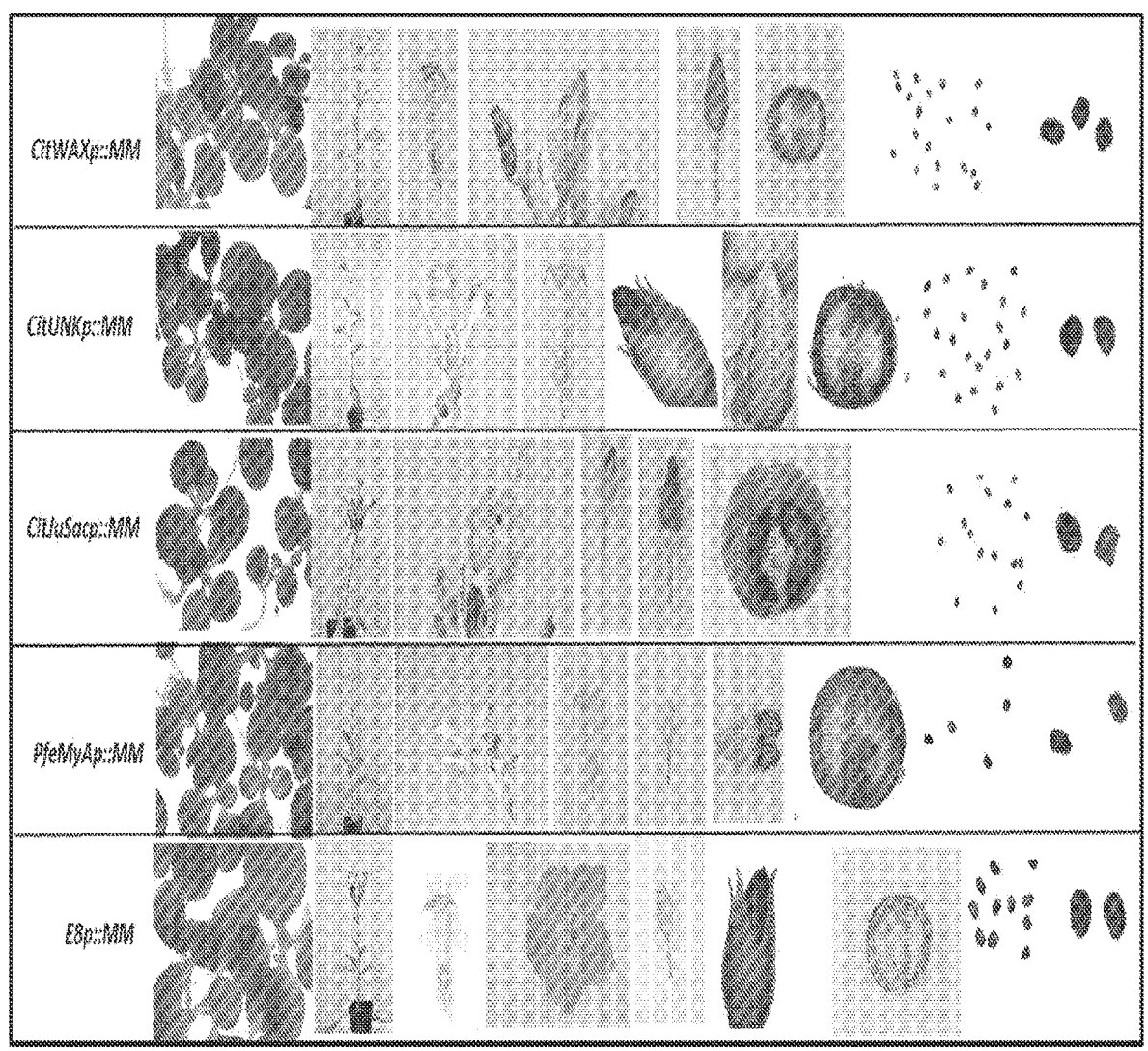
FIG. 14 shows the phenotypes of transgenic tobacco plants transformed with the Promoter::MoroMybA constructs.
Figure 15A:
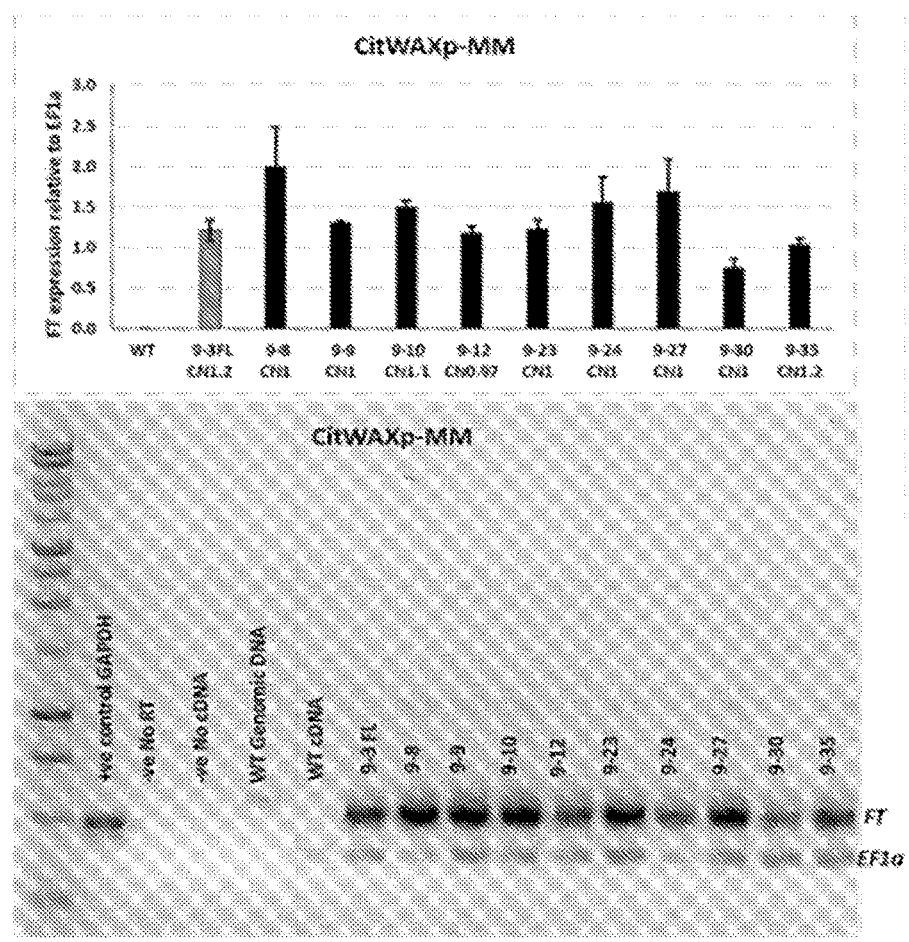
FIGS. 15A-15E show the results of semi-quantitative reverse transcription PCR (RT-PCR) for transgenic citrus plants transformed with the Promoter::MoroMybA constructs as compared to wild type. The upper panel in each figure shows in histograms the AtFT expression relative to the internal control CitEF1a (Y-axis) on transgenic citrus lines with different copy numbers (CN, X-axis) and wild type for each construct tested. The bars highlighted in pink are the early-flowering lines. The lower panel in each figure shows the corresponding agarose gel electrophoresis results.
Figure 15B:
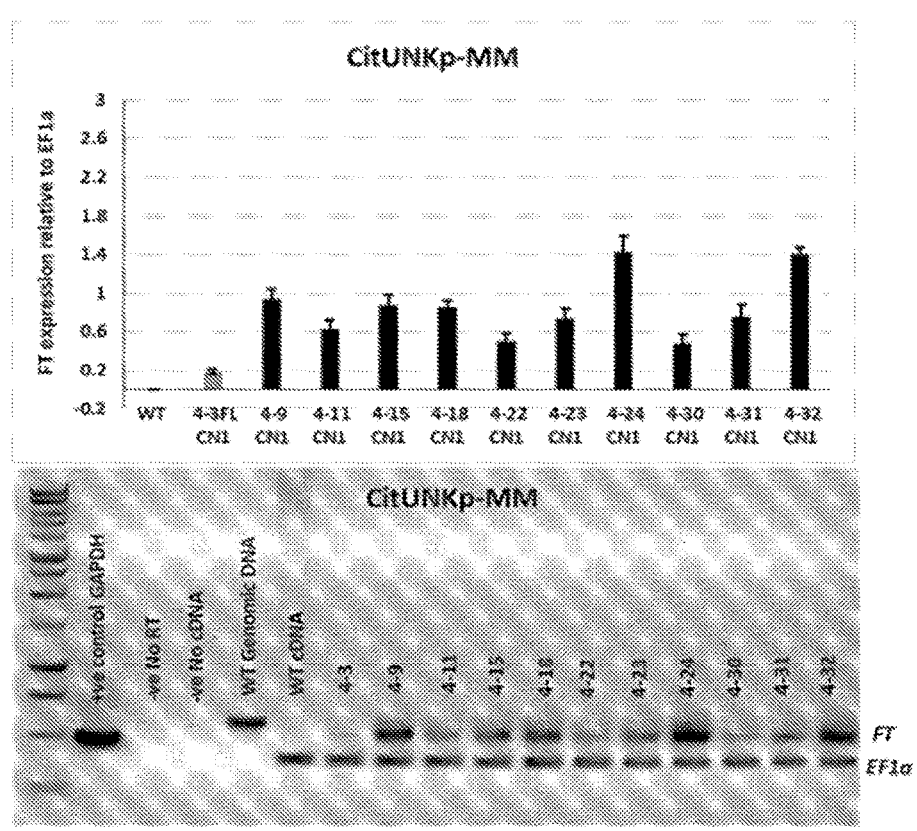
Figure 15C:
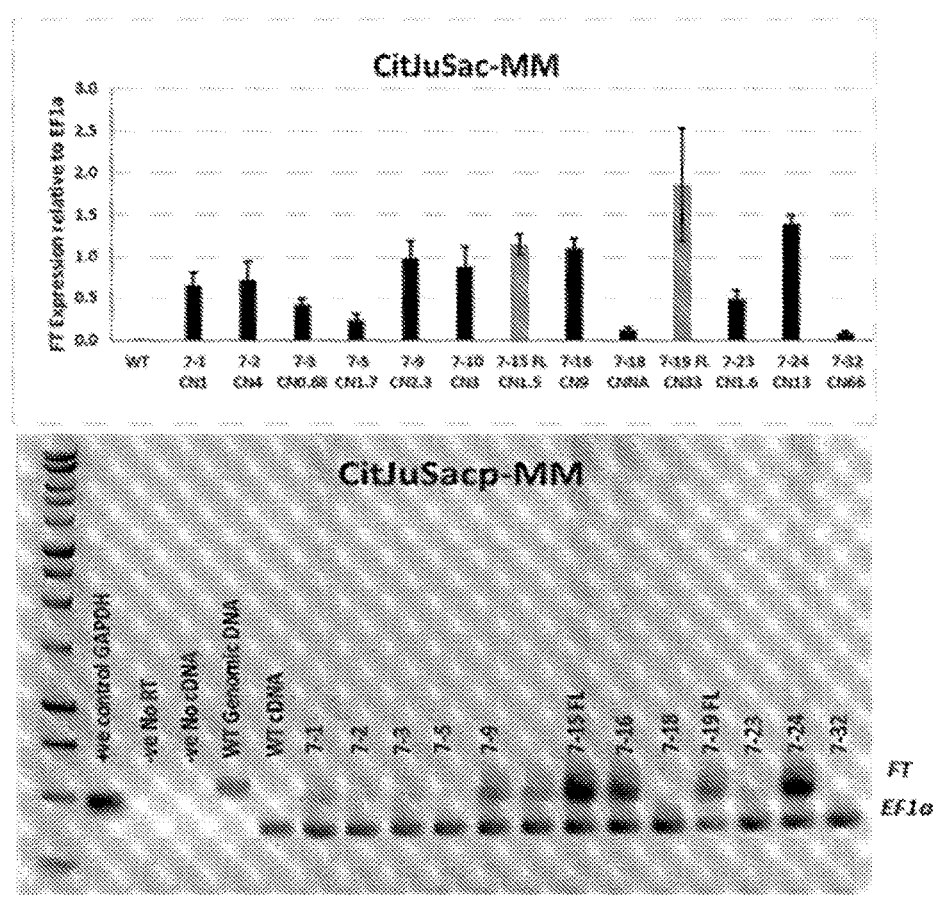
Figure 15D:
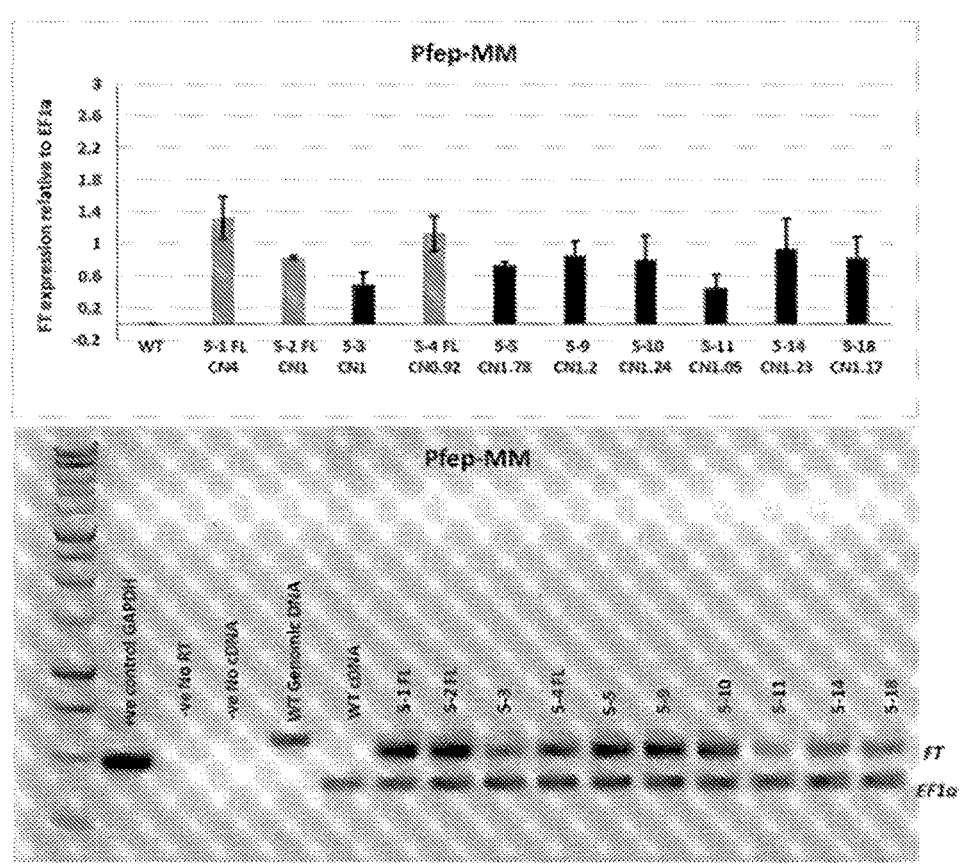
Figure 15E:
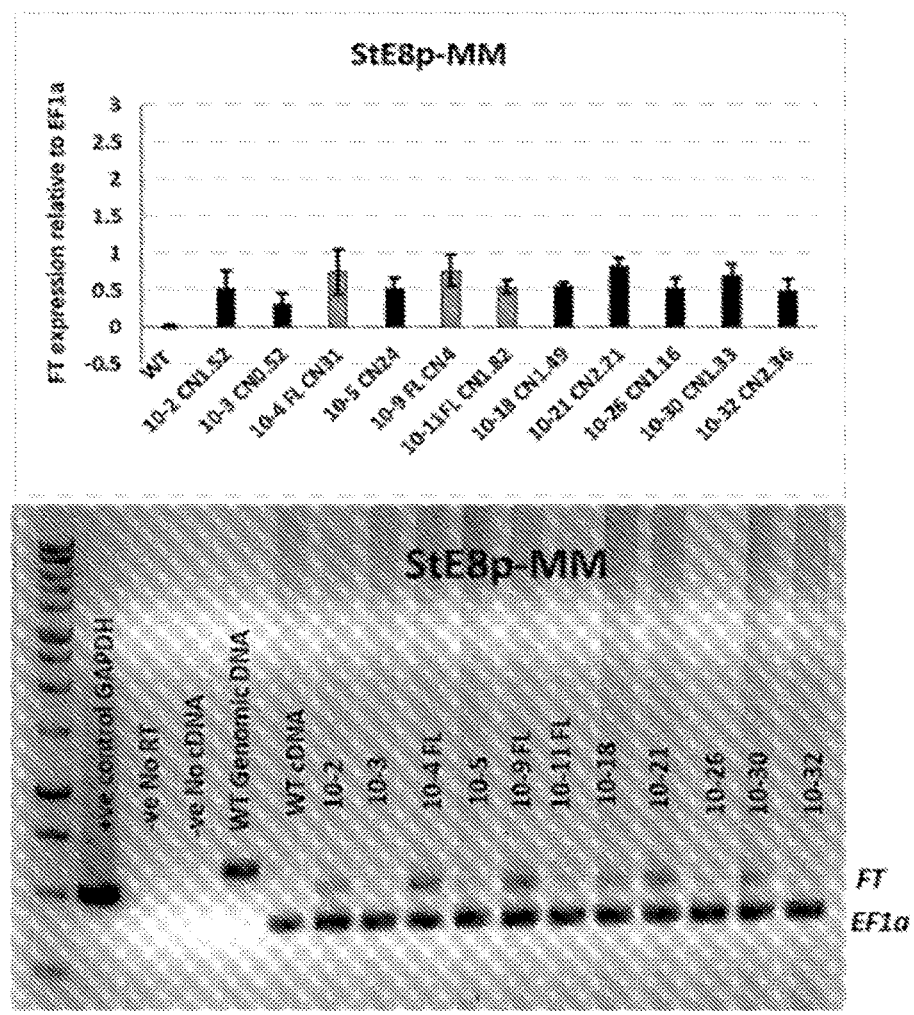

A summary of the tobacco anthocyanin accumulation analysis on a representative line for each construct is shown in FIG. 14.

Phenotypic Analysis of Flowering Time in Transgenic Citrus Lines

Fruit and forest trees have a long juvenile period, during which no reproductive development occurs. In citrus, the juvenile period ranges from 5-15 years, which has hampered traditional breeding and genetic studies. Therefore. AtFT was added to the vector constructs for citrus plants to reduce the time to flower and more quickly assess citrus fruits accumulating anthocyanin.

Figure 11:
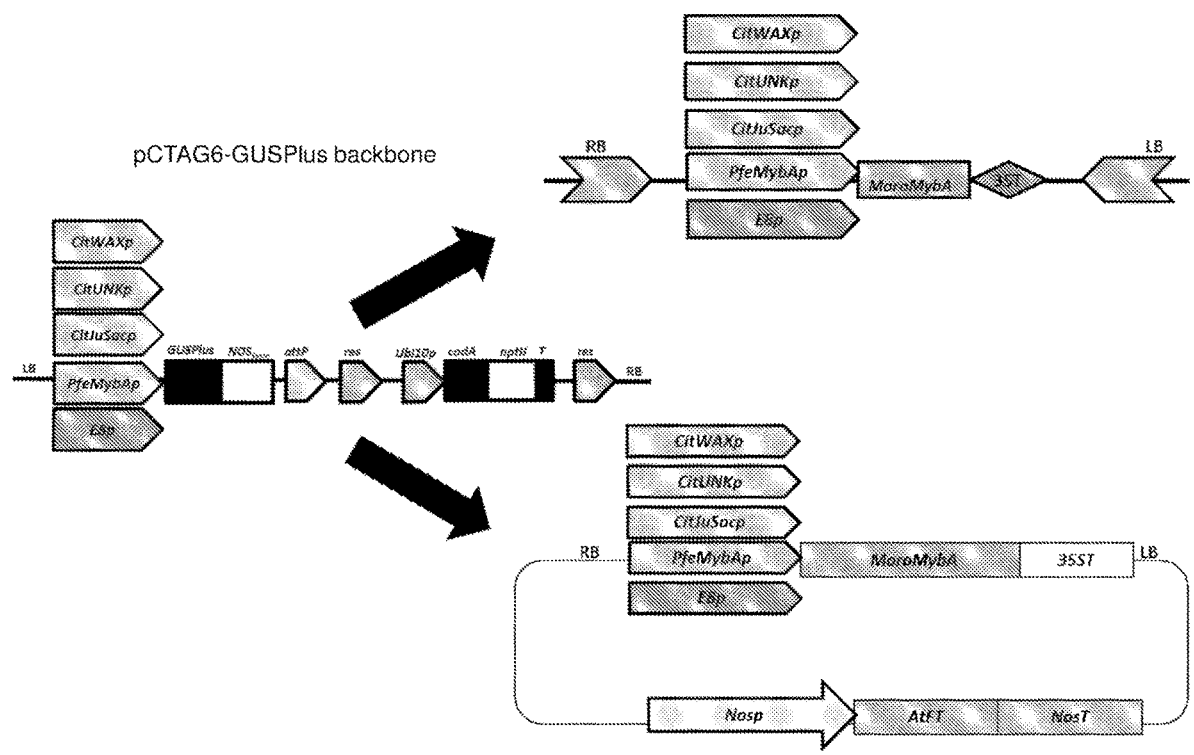
FIG. 11 shows the molecular constructs used for the anthocyanin accumulation study. For generating transgenic *Arabidopsis* and tobacco plants, the Promoter::MoroMybA constructs were inserted into the pCTAG6-GUSPlus vector backbone for transformation (upper panel). For generating transgenic citrus plants, the Promoter::MoroMybA constructs as well as the Nosp::AtFT::NosT construct were inserted into the pCTAG6-GUSPlus vector backbone for transformation (lower panel). Nosp, nopaline synthase promoter; AtFT, *Arabidopsis* FLOWERING LOCUS T gene; NosT, nopaline synthase terminator.

*Agrobacterium*-mediated transformation of Mexican lime explants resulted in the production of a large number of putative kanamycin-resistant transgenic plants. The constructs used for transformation are shown in FIG. 11 with selected Promoter::MoroMybA::AtFT constructs (promoters CitWAXp, CitUNKp. CitJuSacp, PfeMybAp and E8p). There was no difference in the ability to regenerate shoots following co-cultivation and incubation with any of the designed vectors. All plants grew normally and there was no phenotypic abnormality observed between transgenic plants and non-transgenic controls. Rooted plants developed slowly in the first six months of transferring to soil, followed by rapid plant growth. 10-15 transgenic lines from each construct were hardened off in the greenhouse, ddPCR was conducted to identify 1-2 copy lines. Genetic analysis of citrus species is challenging, while traditional methods like Southern blot can be difficult or time taking. Droplet digital PCR (ddPCR) serves as an efficient, faster method for identifying single-copy transgene insertion events from a population of transgenic lines. In this study, transgenic citrus lines with a single copy were successfully determined with ddPCR (Table 11)

TABLE 11

Days to flower and copy number comparison

| Line | Date of flowering | Date of transfer from RM | Copy number | Age in weeks during flowering |
|---|---|---|---|---|
| JS 7-2 | Nov. 14, 2017 | Aug. 16, 2016 | 2 | 65 |
| JS 7-15 | Jun. 14, 2017 | Dec. 19, 2015 | 3 | 77.6 |
| JS 7-19 | May 31, 2017 | Jan. 20, 2016 | 4 | 71 |
| JS 7-23 | Nov. 24, 2017 | Apr. 21, 2016 | 1 | 83 |
| WAX 9-3 | Jun. 7, 2017 | Dec. 29, 2015 | 4 | 75.1 |
| WAX 9-9 | Nov. 17, 2017 | Aug. 16, 2016 | 4 | 65 |
| WAX 9-14 | Nov. 16, 2017 | Apr. 21, 2016 | 3 | 82 |
| WAX 9-6 | Feb. 26, 2018 | Aug. 16, 2016 | 3 | 82 |
| UNK 4-3 | May 31, 2017 | Dec. 2, 2015 | 3 | 78 |
| PFE 5-1 | Jul. 17, 2017 | Dec. 2, 2015 | 3 | 85 |
| PFE 5-2 | Jul. 17, 2017 | Dec. 2, 2015 | 3 | 85 |
| PFE 5-3 | Jul. 17, 2017 | Dec. 2, 2015 | 1 | 85.7 |
| PFE 5-4 | Aug. 10, 2017 | Dec. 2, 2015 | 1 | 88 |
| E8 10-4 | Aug. 9, 2017 | Oct. 29, 2015 | 5 | 92 |
| E8 10-9 | Aug. 9, 2017 | Dec. 29, 2015 | 2 | 84.1 |
| E8 10-11 | Jun. 14, 2017 | Dec. 29, 2015 | 1 | 76.1 |
| E8 10-24 | Feb. 26, 2018 | Apr. 21, 2016 | 4 | 96 |

RT-PCR was done on transgenic Mexican lime lines to test the AtFT expression as compared to the internal control CitEF1a on selected low-copy (preferably single-copy) lines in T0 generation (FIGS. 15A-15E). The two negative controls were one with no reverse transcriptase enzyme added during cDNA synthesis and the other with no cDNA added during PCR. A band size of 500 bp was expected for AtFT expression, using gene-specific primers that amplifies the full cDNA of AtFT used in the construct (lower panels of the figures). All reactions were done at the same time. The upper panels of the figures show in histograms the AtFT expression relative to CitEF1a (Y-axis) on lines with different copy numbers (CN, X-axis) for each construct tested. Based on the results, transgenic Mexican limes showed varying expression levels of AtFT, which was expected due to positional effect of transgene insertion location within the genome. The bars highlighted in pink are the early-flowering lines. Table 11 further shows the comparison of flowering time of various transgenic Mexican lime lines 70-90 weeks after transferring from rooting media. Importantly, these transgenic Mexican lime lines started to flower as early as 70 weeks after transferring to deep soil containers in the greenhouse. Considering transgenic citrus lines generated through tissue culture typically need 3-5 years before they start flowering, these results indicated that AtFT is able to induce early flowering phenotype.

Phenotypic Analysis of Anthocyanin Accumulation in Transgenic Citrus Plants

The pattern, distribution and level of anthocyanin accumulation in young immature transgenic Mexican lime varied widely among different lines and developmental stages. The transgenic lines showed variation in time to rust flowering but generally appeared to require ~70 weeks in deep soil containers. Anthocyanin accumulation phenotypes of the transgenic Promoter::MoroMybA(MM) Mexican lime lines are shown in FIGS. 16-21.

Figure 16:
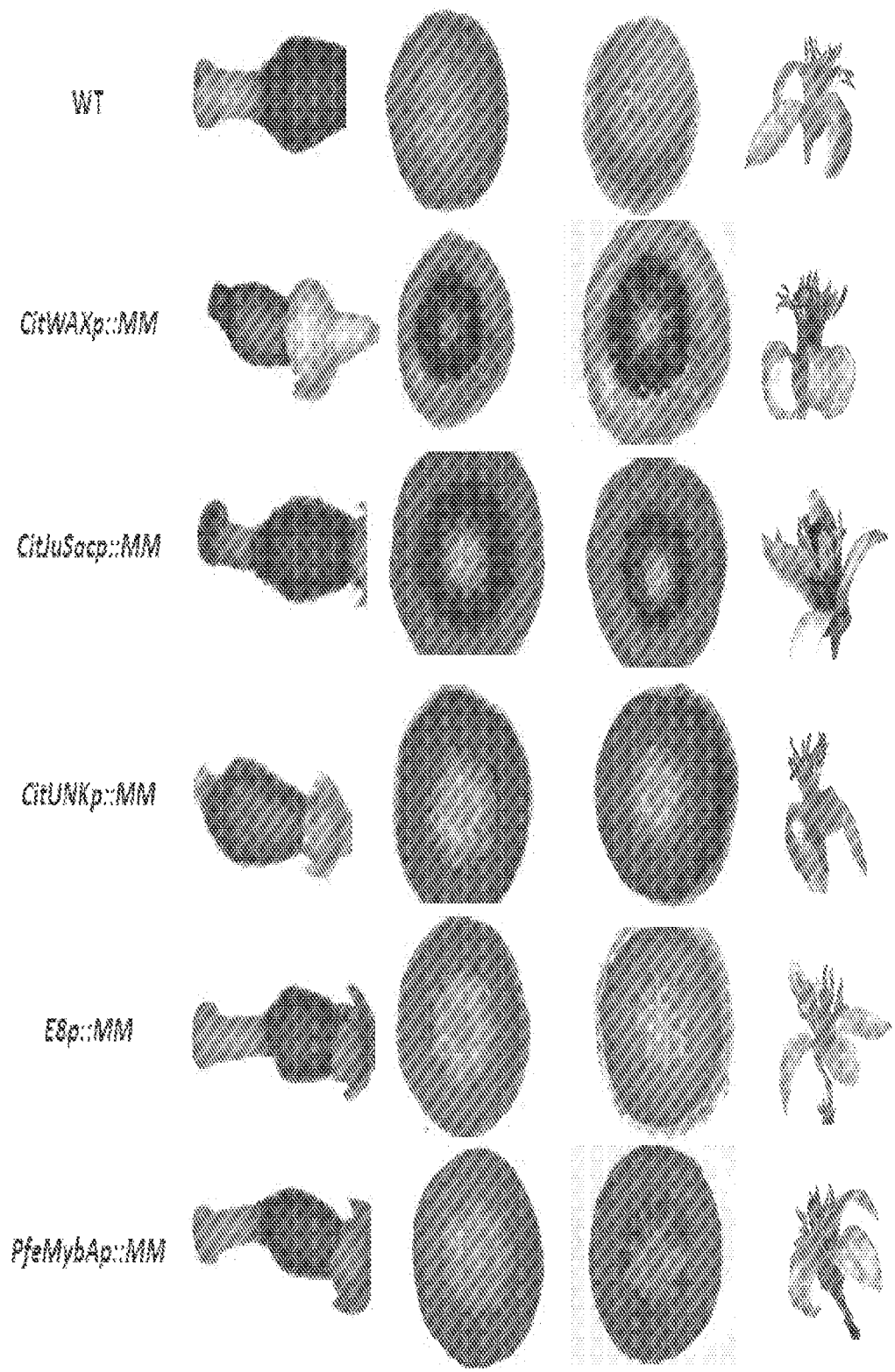
FIG. 16 shows the phenotypes of unripe fruit and flower of the transgenic citrus plants transformed with the Promoter::MoroMybA constructs as compared to wild type.
Figure 17:
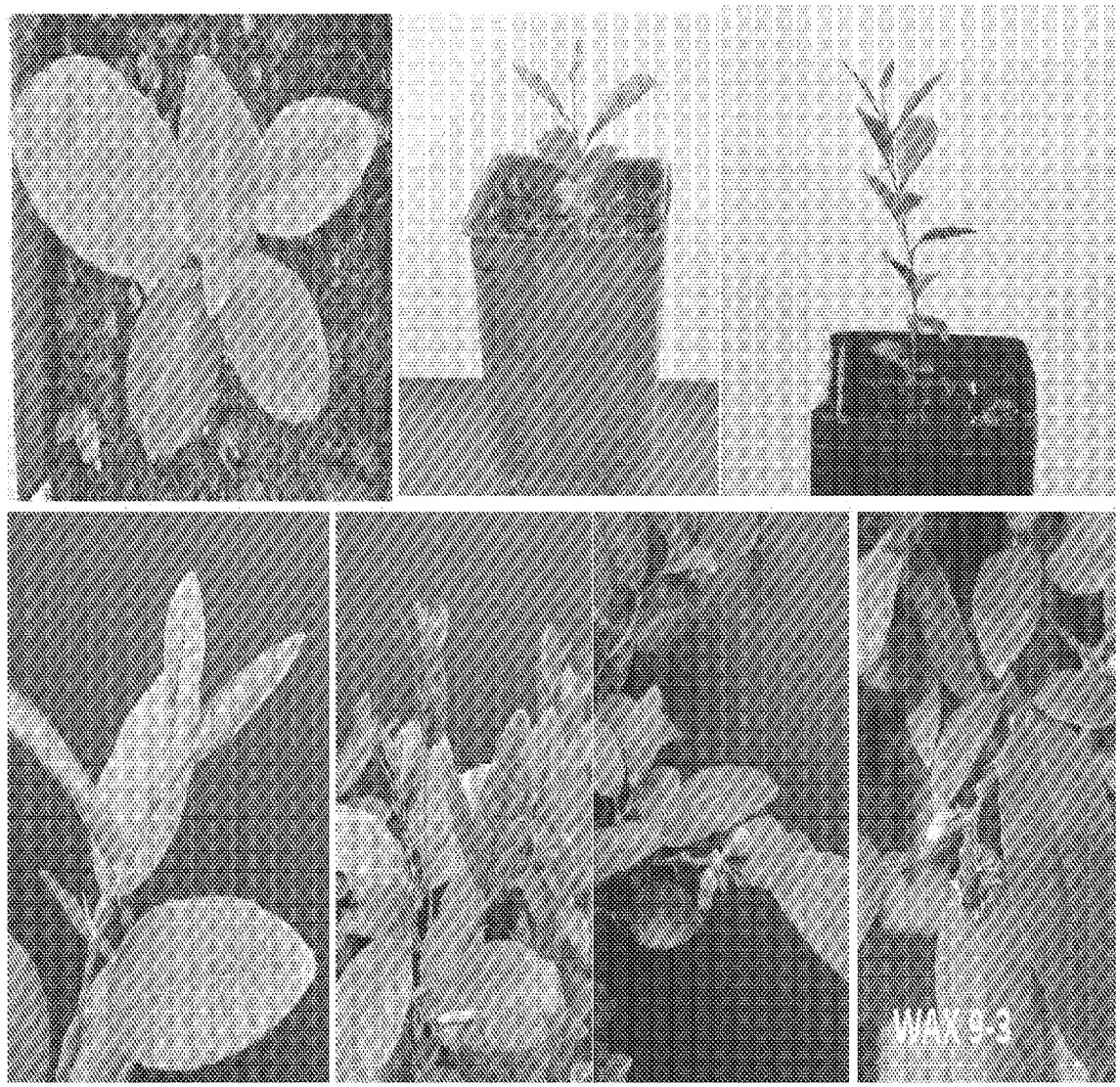
FIG. 17 shows the phenotypes of the transgenic citrus plant line #9-3 transformed with the CitWAXp::MoroMybA construct.

Results showed that transgenic CitWAXp::MoroMybA Mexican lime (line #9-3) had anthocyanin detected in the midrib of young leaves, flowers mainly in the stigma, style and petals (FIG. 16 and FIG. 17). When compared to the WT, fruits of CitWAXp::MoroMybA clearly accumulated anthocyanin in the young immature fruits mainly in juice sacs, seeds and segment membranes, but not in flavedo and albedo.

Figure 18:
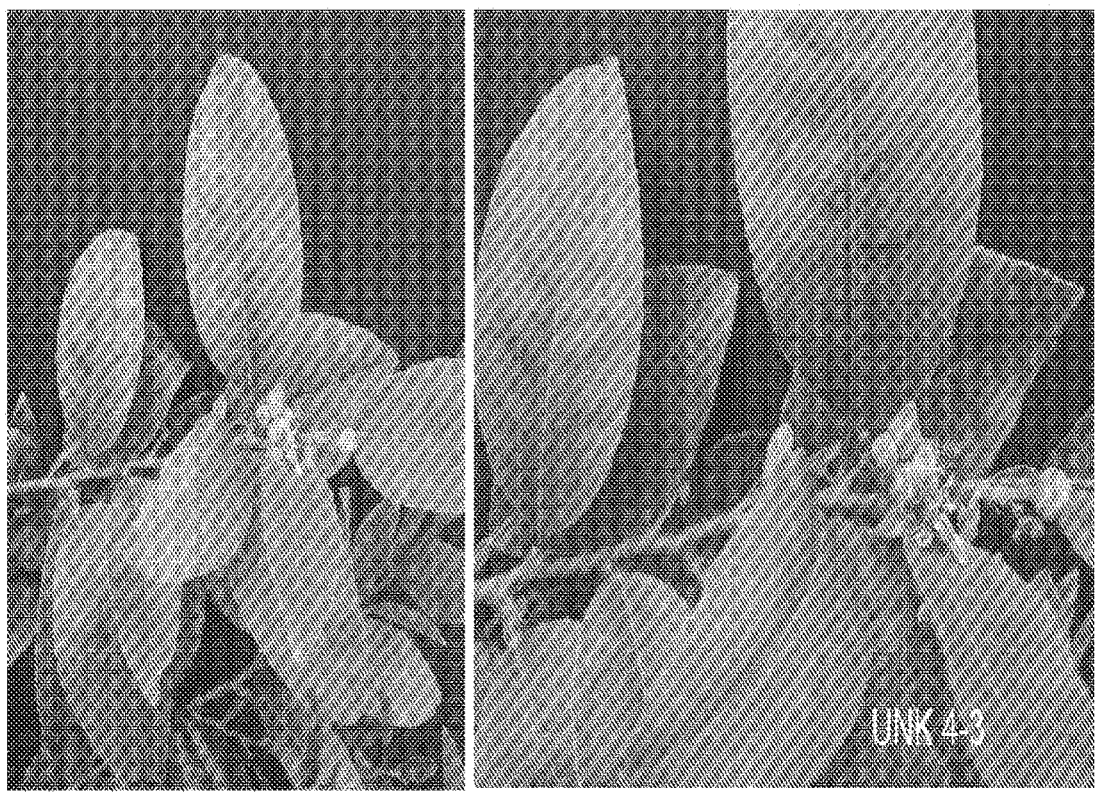
FIG. 18 shows the phenotypes of the transgenic citrus plant line #4-3 transformed with the CitUNKp::MoroMybA construct.

For transgenic CitUNKp::MoroMybA Mexican lime (line #4-3), anthocyanin was not detected in the young or mature leaves, flowers and but weakly in the juice sacs/seeds of young immature fruits (FIG. 16 and FIG. 18).

Figure 19:
FIG. 19 shows the phenotypes of the transgenic citrus plant line #7-19 transformed with the CitJuSacp::MoroMybA construct. Purple coloration indicating signs of anthocyanin accumulation in young plants is highlighted in black circle.

For transgenic CitJuSacp::MoroMybA Mexican lime (line #7-19), anthocyanin was detected in young leaves, not in mature leaves, in flowers mainly in the stigma, style and petals with a visible pink phenotype (FIG. 16 and FIG. 19). The fruits accumulated anthocyanin strongly in juice sacs and segment membranes. The flowers showed typical early flowering phenotype when FT is overexpressed. Most of the transgenic flowers developed on leafy inflorescences, apparently in place of thorns; however, WT usually develops solitary flowers in the axils of leaves.

Figure 20:
FIG. 20 shows the phenotypes of the transgenic citrus plant line #5-1 transformed with the PfeMybAp::MoroMybA construct.

Transgenic PfeMybAp::MoroMybA Mexican lime line (#5-4) did not show any anthocyanin accumulation phenotype in vegetative or immature reproductive tissues (FIG. 16 and FIG. 20). However, this phenotype is not unexpected based on the ripening pattern seen in plum where only mature fruit expressed anthocyanin.

Figure 21:
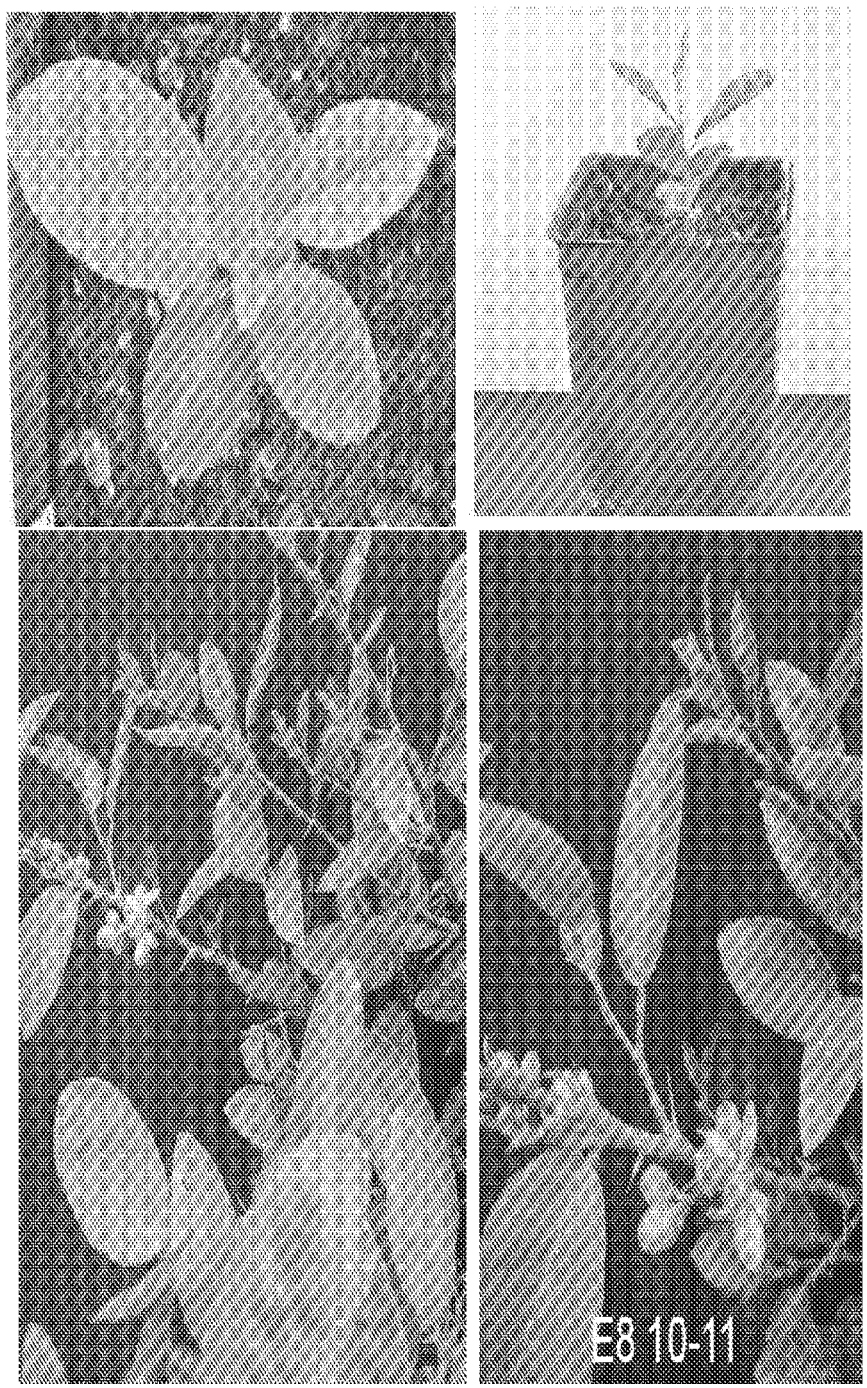
FIG. 21 shows the phenotypes of the transgenic citrus plant line #10-11 transformed with the E8p::MoroMybA construct.

For transgenic E8p::MoroMybA Mexican lime line (#10-11), anthocyanin was not detected in the young or mature leaves, flowers or immature reproductive tissues similar to WT (FIG. 16 and FIG. 21).

When compared to WT, CitWAXp::MoroMybA and CitJuSacp::MoroMybA showed anthocyanin accumulation in juice sacs, seeds and segment membranes, but not in flavedo and albedo. CitUNKp::MoroMybA showed anthocyanin accumulation in juice sacs and seeds only (FIG. 16).

No visible phenotypes in flower and fruit were observed for other Promoter::MoroMybA transgenic lines.

Conclusion

Taken together, the results of this study indicate that the candidate promoters were functional in driving expression of MoroMybA in a fruit-specific fashion. Anthocyanin accumulation was successfully modified in transgenic plants transformed with candidate fruit-specific promoters.

Example 6: Modification of Lycopene Accumulation Using Fruit-Specific Promoters The following example illustrates the use of candidate promoters to modify lycopene accumulation in fruit. During development in plants, there is a coordinated increase in both chlorophyll and carotenoid pigment content, such as the bright red color of lycopene. Increased lycopene content is usually considered a favorable fruit trait. In this study, three target genes were exploited to increase lycopene accumulation.

Methods and Materials

Molecular Constructs

A genetic construct containing the phytoene synthase (PSY) gene driven by the 35S promoter was generated for expressing PSY in *Arabidopsis*. A genetic construct 35S::β/ε cyclase RNAi-35Sp::PSY for silencing β/ε lycopene cyclase as well as overexpressing PSY was generated for transforming Carrizo citrange plants. A genetic construct having three citrus fruit promoters (CitJuSacp, CitWAXp and CitUNKp) fused to PSY, RNAi ε-&β-LCY, and DXS, respectively (CitWAXp::RNAi ε-&β-LCY-CitJuSacp::PSY-CitUNKp::DXS), together with the FT (flowering gene) construct for increased flowering time, was generated for transforming Mexican lime plants.

Transgenic *Arabidopsis* Plants

*Agrobacterium tumefaciens* strain GV3101 was used for transformation of *Arabidopsis* ecotype Ler by the floral dip method (Clough and Bent 1998) that is modified by adding 0.01% Silwet L-77 (Lehle Seeds, Round Rock, Tex.) to the infiltration medium. Primary transformants were selected on MS medium (Sigma. St. Louis, Mo.), 1% sucrose, 0.7% agar with 20 µg/ml hygromycin or 50 µg/ml kanamycin as needed for 10 days prior to cultivation in soil.

Transgenic Citrus Plants

Material used in this study was juvenile shoot of Carrizo citrange and Mexican lime plants that had been generated from seed. Technique used for transformation is described in de Oliveira et al., *HortTechnology* (2016) 26(3), 278-286.

Results

Figure 22:
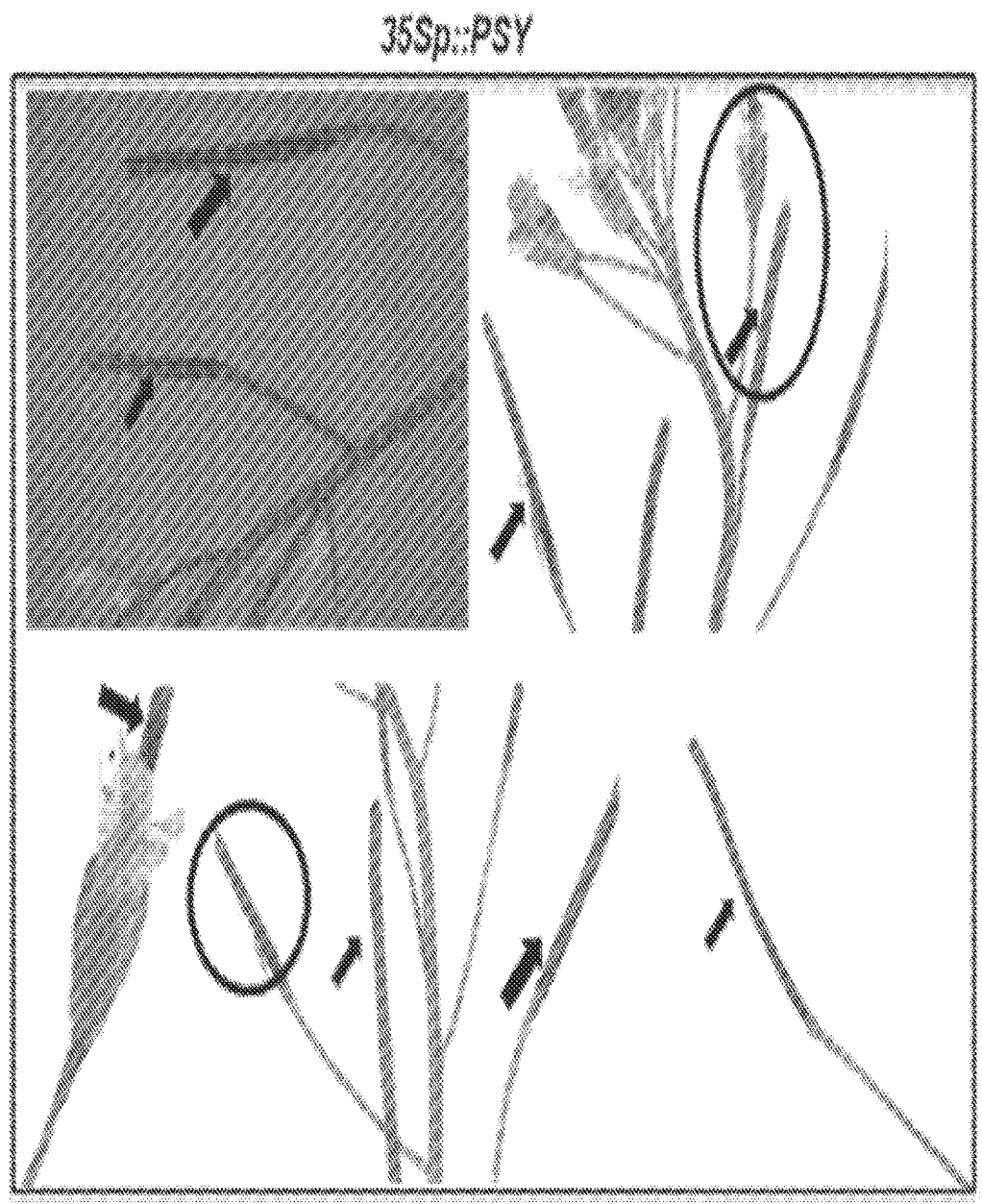
FIG. 22 shows that the transgenic *Arabidopsis* lines transformed with the 35S::PSY construct accumulated lycopene only in the siliques, giving an orange coloration (marked in black circles).

Phytoene synthase (PSY) is the first key enzyme in the carotenoid biosynthetic pathway, and increasing its activity has been shown to increase the red coloration in other plants. FIG. 22 shows the ability of this gene to accumulate lycopene in *Arabidopsis* during fruit development.

Figure 23:
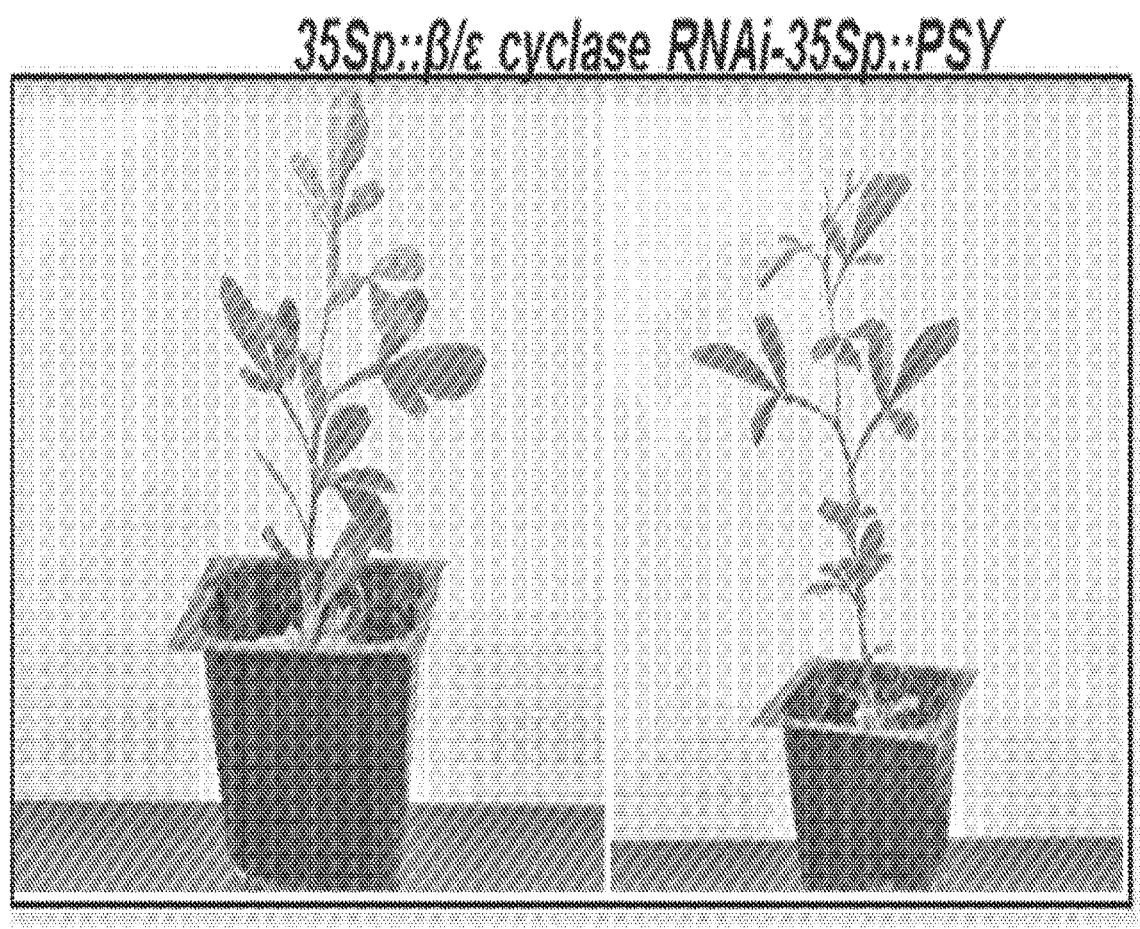
FIG. 23 shows the phenotypes of the initial transgenic Carrizo test lines transformed with the 35S::β/ε cyclase RNAi::PSY construct.

Two enzymes that convert lycopene into carotene in the carotenoid pathway were identified in citrus as ε-LCY and β-LCY. Reducing the expression of these genes should also increase lycopene accumulation in fruit for generation of Cara cara navel-like red-fleshed citrus cultivars. FIG. 23 shows the phenotypes of the transgenic Carrizo test lines transformed with the 35S:: β/ε cyclase RNAi::PSY construct.

The third target is DXP Synthase (DXS). DXS acts early in the carotenoid pathway to produce initial building blocks for lycopene synthesis. Previous research in plants indicates that the DXS gene is a bottleneck in the system and increasing its production should produce more overall lycopene.

Figure 24:
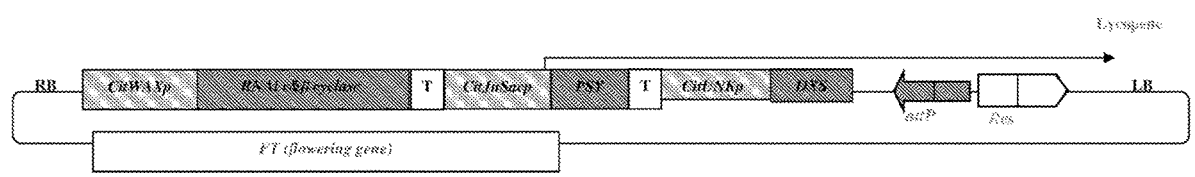
FIG. 24 shows the CitWAXp::RNAi ε-&β-LCY-CitJuSacp::PSY-CitUNKp::DXS construct and the FT (flowering gene) construct used in the transgenic citrus lycopene accumulation study.

To increase lycopene accumulation in citrus fruits, a genetic construct combining the above-described targets, together with the FT (flowering gene) construct for increased flowering time, was generated (FIG. 24), where selected candidate citrus fruit promoters were fused to the three targets (CitWAXp::RNAi ε-&β-LCY-CitJuSacp::PSY-CitUNKp::DXS).

Figure 25:
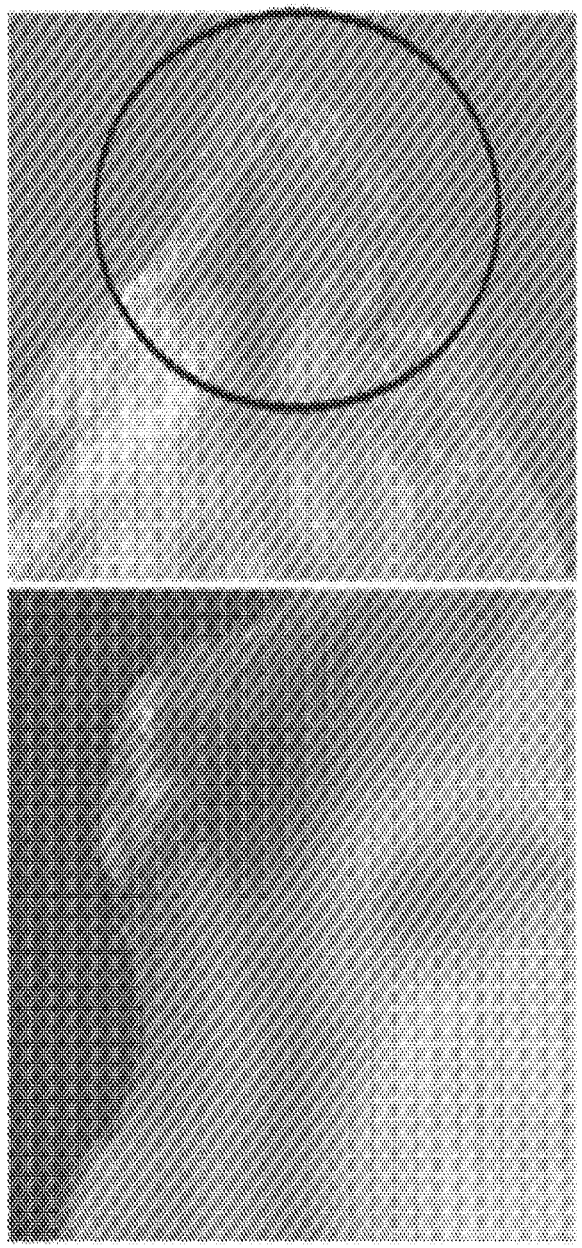
FIG. 25 shows the phenotype of lycopene accumulation in the transgenic Mexican lime callus transformed with the CitWAXp::RNAi ε-&β-LCY-CitJuSacp::PSY-CitUNKp::DXS construct and the FT (flowering gene) construct, with the signs of lycopene accumulation as light orange blush marked in black circle.
Figure 26:
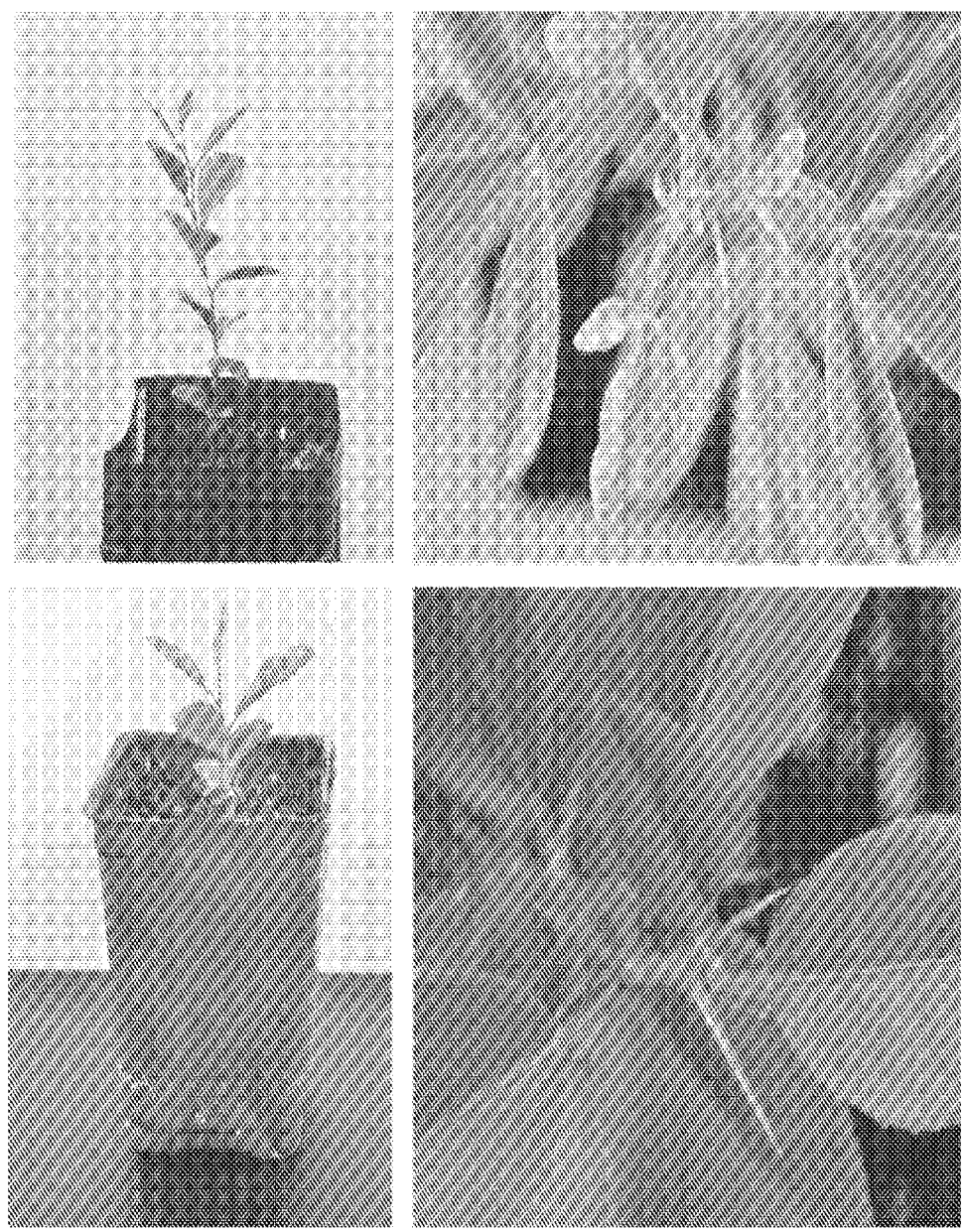
FIG. 26 shows the transgenic Mexican lime (upper panel) and Carrizo (lower panel) transformed with the CitWAXp::RNAi ε-&β-LCY-CitJuSacp::PSY-CitUNKp::DXS construct and the FT (flowering gene) construct, with no visible lycopene accumulation in the vegetative growth of the plants.

A total of 25 independent transgenic citrus lines were generated. Preliminary analysis of the transgenic Mexican lime callus showed signs of lycopene accumulation as light orange blush (FIG. 25). Preliminary analysis of the transgenic Mexican lime and Carrizo young plants showed no visible lycopene accumulation in the vegetative growth of the plants, which is an expected phenotype with the candidate fruit-specific promoters used. No flowering or fruiting has occurred yet for these transgenic citrus lines.

Conclusion

Taken together, the results of this study indicate that the candidate promoters were functional in driving expression of lycopene pathway genes in plants. Preliminary analysis of the transgenic citrus lines showed expected phenotype in modifying lycopene accumulation in plants.

REFERENCES

Blázquez, M. (2007). Quantitative GUS activity assay of plant extracts. *Cold Spring Harbor Protocols.* 2007(2), pdb-prot4690.
Collier R, Dasgupta K, Xing Y P, Hernandez B T, Shao M, Rohozinski D, Kovak E, Lin J, de Oliveira M L P, Stover E, McCue K F, Harmon F G, Blechl A, Thomson J G and Thilmony R (2017) Accurate measurement of transgene copy number in crop plants using droplet digital PCR. *Plant J* 90 (5):1014-1025.
Dasgupta K, Thilmony R and Thomson J G (2015) Developing novel Blood and Cara cara-like citrus varieties. *Citrograph* 6(3):65-69.
Dasgupta K, Shao M, Thomson J G (2016) Purple is the new orange—The development of novel Blood and Cara Cara like citrus varieties. *Citrograph* 7(3):54-58.
Dasgupta K, Thilmony R, Stover E, de Oliveira M L, Thomson J (2017) Novel R2R3-myb transcription factors from *Prunus Americana* regulate differential patterns of anthocyanin accumulation in tobacco and citrus. *GM Crops & Food* 81-21.
de Oliveira M L, Thomson J G, Stover E (2016) High-efficiency Propagation of Mature 'Washington Navel' Orange and Juvenile 'Carrizo' Citrange Using Axillary Shoot Proliferation. *HortTechnology* 26(3):278-286.
de Oliveira M L, Febres V J, Costa M G, Moore G A, Otoni W C (2009) High-efficiency *Agrobacterium*-mediated transformation of citrus via sonication and vacuum infiltration. *Plant Cell Rep.* 28(3):387-395.
Jefferson, R A, Kavanagh, T A, and Bevan, M W (1987) GUS fusions: β-Glucuronidase as a sensitive and versatile gene fusion marker in higher plants. *EMBO J.* 6:3901-3907.
Verde I, Jenkins J, Dondini L, Micali S, Pagliarani G. Vendramin E, Paris R, Aramini V, Gazza L, Rossini L, Bassi D (2017) The Peach v2.0 release: high-resolution linkage mapping and deep resequencing improve chromosome-scale assembly and contiguity. *BMC genomics* 18(1):225.
Weigel D, Glazebrook J (2002) *Arabidopsis*: A Laboratory Manual. *Cold Spring Harbor Laboratory Press*, Cold Spring Harbor, N.Y.

---

What is claimed is:

1. A genetic construct comprising a promoter operably linked to a heterologous polynucleotide having a nucleotide sequence encoding a product of interest, wherein the promoter comprises a sequence as set forth in SEQ ID NO: 2; SEQ ID NO: 3; SEQ ID NO: 4; or SEQ ID NO: 5, or a sequence having an ATCT-motif, a G-Box, an HSE element, an MBS, a CAAT box, and a TATA box, and at least 96% identity to SEQ ID NO: 2; SEQ ID NO: 3; SEQ ID NO: 4; or SEQ ID NO: 5.

2. The genetic construct of claim 1, wherein the product of interest is an RNA molecule or a polypeptide.

3. The genetic construct of claim 1, wherein the product of interest is in a metabolic pathway selected from the group consisting of an anthocyanin metabolic pathway, a tocopherol metabolic pathway, a fatty acid metabolic pathway, a carotenoid metabolic pathway, a lycopene metabolic pathway, a betalain metabolic pathway, and a flavonoid metabolic pathway.

4. The genetic construct of claim 1, wherein the product of interest is a polypeptide selected from the group consisting of a MYB transcription factor, a phytoene synthase (PSY), a lycopene cyclase (LCY), and a DXP synthase (DXS).

5. An expression vector comprising the genetic construct of claim 1.

6. A transgenic plant comprising the genetic construct of claim 1.

7. A plant part from the transgenic plant of claim 6, wherein the plant part comprises the genetic construct.

8. The plant part of claim 7, wherein the plant part is a stem, a branch, a root, a leaf, a flower, a fruit, a seed, a cutting, a bud, a cell, or a portion thereof.

9. A method for modifying a fruit phenotype in a plant, comprising:
(i) transforming a plant cell with the genetic construct of claim 1, wherein expression of the product of interest is associated with modification of the fruit phenotype;
(ii) regenerating a plant from the transformed plant cell; and
(iii) growing the regenerated plant to produce fruit of the modified phenotype.

10. The method of claim 9, wherein the fruit phenotype is selected from the group consisting of size, weight, color, shape, firmness, glossiness, flavor, aroma, secondary metabolite content, peel thickness, seed number, juice quality, juice sugar content, juice acid content, juice taste, juice color, and juice yield.

11. The method of claim 9, wherein the fruit phenotype is selected from the group consisting of anthocyanin content, tocopherol content, fatty acid content, carotenoid content, lycopene content, betalain content, and flavonoid content.

12. The method of claim 9, wherein the plant is selected from the group consisting of orange (*Citrus sinensis*), mandarin (*Citrus reticulata*), lime (*Citrus aurantifolia*), grapefruit (*Citrus paradisi*), lemon (*Citrus Ziman*), pomelo (*Citrus maxima*), citron (*Citrus medica*), *papeda* (*Citrus micrantha*), and *Prunus* sp.

* * * * *

SEQUENCE LISTING

```
<160> NUMBER OF SEQ ID NOS: 31

<210> SEQ ID NO 1
<211> LENGTH: 3401
<212> TYPE: DNA
<213> ORGANISM: Citrus sinensis

<400> SEQUENCE: 1
gagaaatctg gatttatata tatatactga tctattctta tctttgtacc ttgttttatt        60
gagaaatctg gatttatata tatatactga tctattctta tctttgtacc ttgttttatt       120
ttattttatt aagtaaaatc aatcacttgt tatctttatt tttcagacaa tcccgagggg       180
taaaccagtg aatttatata gaaaacaacg gaactacgaa gctgttctgt ttcagcttta       240
cacgtaattg gccgaaggaa atagtcaggt ggggataatc aaaaacctcg ttcacttctc       300
atctcgacac gtgtcaatgt ccatttattt aattacctca cctctcctct tctaagtctg       360
ggatttccct tatttatttt tttaagaaaa aaaatgtcta aggttccccc cccccccct       420 atggcctctc caccgtctga tcaaagaaat agggtataat aataacaaca ataaaagtaa       480
aaataaagga atgcaaagct aaaagcaaaa taacgctcca taatattcgt tttgttttac       540
atttatattt ttttttgatac attaaatcat ctagtatttg aaaatcacat tggaccctga       600
ttaattcaaa ttcgagctaa gtaggaccac taggacggta aagttctctc ccgactaatc       660
taaattcgag tcgagtaaga tcactaaggc aaattcgagc cgagtaagat cactcggcgg       720
caaaattctc ccaacaagta tttaatgcat ttgtattctc aagtctcgaa tcgaagactt       780
tggttaagtt agaacaacct catactagtt gactcacgcg cttgttagtt tgttatacac       840
ttatatgata acaataagag tcaaaatgaa gtcatacaga cctaataata ataataataa       900
taataataat agggcaaaaa gaaaaggtat aggaaagaga tcgaagaagc aatagcggag       960
gcaatataat ataactag aagtgataga ttataaatag atatatgaat atatagtgat      1020
```

```
agaagaagaa agaaaggaga agaaagacgt cgctctcatc attttctcca atagaggaaa   1080
gctgtacgag ttttgcagta gttcaaggta tacgcatatg cacacagata tgttatcacc   1140
aaaacaacta aacagctaca attaaatgaa aattatgaaa cacaacacaa aaagctctct   1200
ctttctctct ctctctctct ctcttctcac ttggcttagc tagggggggt ctatgggaga   1260
ttctttcttt tgcttggttt cttgttttga attccgactt tggatcttga aaccataaga   1320
aatattattt tttgctgttt ttgatcatcc caaagaaaaa aatattgata aagaggagaa   1380
agtattgttt ctttggagac tggagttgag tttttttgccc ttttggtgaa tgtctcggcg   1440
tttttagcag cttcactgtt tccctcttct tattcttgtt tagatctgca actgcaaaat   1500
tcatcaaaag aagatactca cacacctcac tcttacatct tttaatgtat tattatcact   1560
gttatattca ctctaattaa tttcctctct tgtttttttct ttttctccct gtctttttttc  1620
tttttttccat ttgttttcgc ctattcacac tttcatttcc attttttgttt tcttcttttt  1680
ccgttttttgc ttcattttttt ttttcttctt acttcgaaaa agttcacctg atctattaat  1740
attcaatttt tccaaagcaa atcaaaccta atttcaagta gtcaccttat tttttgttct   1800
ttataagtaa atttactggt tcttccaaat agttcaagct attttctttta ttttagttta   1860
attagatctc atgaagctta aacatacaaa ttctgataga gggagagcga ttttttttttt  1920
tttttttgggt attttatttc atgctttctg cagttttcag cccaaaaaaa aaaaaaaatc   1980
atgcttaatt tctgttttga tgagtctgac caaatcaagc caaatatttta agacatttat   2040
tagtgattta cccagctcaa attgtgttct tgatcaaggt tagttctttc tgttgtatga    2100
gagttttggt tctttccagt ggatcatagc gttgttcttt ttatggagac atctccatat    2160
ctgctgctgc tgctgctgct tcagagctt aagctagggt ttcatcttcc caaagttact     2220
tttgatttta agcttccttc tttctcacac aaacacacac atgattcaga tctgaactat    2280
ttatgatgaa ttgactattg acatgttaag actgatttaa ctacatctaa tctttaactt    2340
ctttttataa tttttatcat ttattatgta tgaaaaaaat agggtttttt tatttgtaca    2400
ttcactggat tagaagttaa tatttatcat gttcttttct gtcttttat tttatttttac     2460
ttatttttt cttgggggtt aaattcggat ggcatacaat ctacacaata acttctgagt     2520
tgtgtggaat acaaaatgga ttaacaaaga gattttaagg aaattggaaa aggtgattat    2580
aacctagata taattccccc tcccccccccc cccccaaaa aaaaaaacac tttcttacaa    2640
tacttcgcta gataaatttga tgtttattta attttttaatg tacaatgagg gaaattaaag  2700
acagcttgat ttacagtccc catatgttat ttaactttttt aaaaaaaaat tgagggacat   2760
aaaaatctca agattaaacc taaagattta ggccttttga attgaggcct atatcttctt    2820
tttctttctc tcccattcta atttaaaact tatcaataat taccttgcca gtgcaaacac   2880
tagctagtga ctgatgttca tgtccatgca tttgtggagg gttaattaat aatgtattcc   2940
tttttttcatt aataaatttt atgcagatgg aaacataata ctagaaactg aatatttatt  3000
tttctatcaa attgtttcct aagaactgaa acaggctcta aagcattaac caaaccgatc   3060
ctattggggt tccaaaattt tcttccttcc tttccagttt cacccaatat atattaatct   3120
attgtgtggt tcattcaaa gtcaaaattg ttttggtat aacctttcat gcaatagttt     3180
tcaattattt gttctctcat tgtgattgat tgttcagtaa taatagttaa tataactatc    3240
agtgcgtgag tgcgttcatt taatttgatg tgttatataa tgcctttttt ttttttttttt  3300
ttcaattcat ctttcattgt tgactaatat atttatgcaa tttgcggagg gctaatgtat   3360
tcctttttctt tgataacccc atgcgaaaat ttaattagca t                      3401
```

<210> SEQ ID NO 2
<211> LENGTH: 1274
<212> TYPE: DNA
<213> ORGANISM: Citrus sinensis

<400> SEQUENCE: 2

| | | | | | |
|---|---|---|---|---|---|
| gagaggaaga | gaacaacaaa | ttaataaagg | cggagcaatg | aatgcatgac | gtcaaaaaat | 60 |
| tcctgcagag | gttaagacag | agtgcacaag | cacagaagcg | agcaggtatc | tgaaaacatg | 120 |
| tatttgatct | ttattggggt | agcaaaagcc | ggtgagaaca | taaatggtt | gtcggtgaca | 180 |
| attataaaca | attgggccta | gttgcacctg | cactgtatgc | ttttattatt | gttttacttt | 240 |
| ttactctagc | acaatttttac | tgaaaaatgt | cttttgccct | cacaatactc | tttattcttt | 300 |
| atgcttaatt | atcatattat | catttctttc | attttttttt | gaaaaaaaaa | taattcttat | 360 |
| ttaagaattt | aaatcaacta | caatatttgt | ttaataggac | aataacagtt | ttatataaat | 420 |
| ttttttcact | cctaatttta | ttttttgag | ataagattta | aaaagaaac | accaatacac | 480 |
| cattattatt | ttttaacttc | ttattttaac | tcctctattt | tattatgata | tttacaagta | 540 |
| atttaaagtt | aatacgtcct | cttaattatc | aatgagagtg | gatttaactt | attttgaact | 600 |
| taaattttga | tttagatatt | caaactaatt | cgtataattg | atttagtata | ttcaaataat | 660 |
| ttacttgtat | aattttttt | ttaaatttaa | tgtatagtaa | tgactctata | tttttattca | 720 |
| taaaccttta | ttttttgat | taattatttt | cttaaggaaa | aaattaaaca | aatatataaa | 780 |
| ggacgattgt | gttacagaga | gcatttaata | aagcaccaat | ggagaaaagg | aacacttgtc | 840 |
| gcaggagcga | ctgaccctag | cactgctcct | attattcctt | agaagaaggg | agcgactgac | 900 |
| gctagcactg | ctcctattat | taattgtatt | ttttttttta | aaaaaagaa | agaaccctta | 960 |
| attgctgcta | cacactttaa | tgtgataatt | aaataatcac | gtgagagctg | ggggtgagct | 1020 |
| agctgtagct | gtgacatttt | taattgaggc | caacaaaata | tctccacgtg | taaccgtaat | 1080 |
| gttgaatacc | caattgggct | tcgggaaaga | aaaattcccc | attgattgat | ctctcatttg | 1140 |
| acttgaccgt | cctgatgatg | acacgacatc | taacttgaat | ccatcatccg | aatgaacaag | 1200 |
| aacattatat | aattagcacc | cctccagctc | tactagcaat | tgcatgttgc | attacctcaa | 1260 |
| agtgcaaaca | aaga | | | | | 1274 |

<210> SEQ ID NO 3
<211> LENGTH: 2036
<212> TYPE: DNA
<213> ORGANISM: Citrus sinensis

<400> SEQUENCE: 3

| | | | | | |
|---|---|---|---|---|---|
| cctcaatctg | caccactaag | acgaatgaca | agtgagctga | acaataata | taaaaatgta | 60 |
| aaactgtgaa | tcaattacaa | caattgcatc | taattagatg | cacagataga | ctttgaaagt | 120 |
| ttgcaaagtc | cagccactct | tggtaaacta | ataacggcat | taattatgtt | tattaataac | 180 |
| attaaaataa | tataagcaat | atgactcata | atctaaaata | atttgagct | aagacccttta | 240 |
| gaataaactc | tggtcgaata | gtaattcagg | attataacta | attaagtagg | ctcaaaatttt | 300 |
| ttataacaga | tttgtataaa | atattttgat | atttttatt | tatactgata | tttaatatttt | 360 |
| tataatttaa | atttcattat | tcatttatta | ataattatag | aaataaaatc | aaaattaaaa | 420 |
| atgaatacaa | ggaaatgggg | caatgggtag | gggatgggga | ttccacctcg | ttctcgtccc | 480 |
| ttcctcgaat | aagaaattga | gtatagacac | acatgtatac | atacatacat | atatcctctt | 540 |

| | |
|---|---|
| tttagaaatc tggaacaact ggtattattt ttatttcttt ttccattgaa aaaaatgaga | 600 |
| cacgaatatg gagtaaatgt gagaaactaa ttagggaaat ttggctagtt ttttatgata | 660 |
| aactacttac atcagtccaa agaaacattt atgggacata cccttattct ctagccatgc | 720 |
| attgtttgtt ttcttttcata aaagtgtgca tgactgaaat ttgtcatgtg atcggccatg | 780 |
| tcttgtatct caaactagat taaattgcaa acaattcat cacgtcgttt tctttgttta | 840 |
| atttattgtc gtataaggat ttatttctac tgtaatgatt catatacaga aaagaaact | 900 |
| gttgcaatta gggctgcaat aatggatcga tcgaaatgac aataagacaa attatgaagt | 960 |
| aaaggctgtt ttttttttt tctaaatgaa acataagcta tttaattttc cttttgtttt | 1020 |
| tatgtaaatt ggacttttac tattagagtt ggactattgg ccattggcac tcagctaatc | 1080 |
| tcttcatgaa tccttttttt tttgttatag ttattttatt ttcaaaaata tcattttctt | 1140 |
| aaacgcacta ctctaaatat tttatttaaa tttttttatt gttataactc aaagtagttt | 1200 |
| cgtactatat ttcattttt ttgcactctt attgttactg tatatacata ttaaaaagta | 1260 |
| ttatgagtga taaaatttc aagtgaagtt ttataaggat aacaaaggga tgccagtaac | 1320 |
| tttactctta ctgttatagc gattcagccc aaagtaaatg tatatatatt atttatttaa | 1380 |
| aaaaataaga gagagaaatt tagtgggtca aaacgcatta cctcaatatc ttttaagcag | 1440 |
| ataagttaga tgagtccttt aatgagaccc atcaacttaa attgatagaa ttttgaggaa | 1500 |
| gtttttgatg ttcgtgaagc aatgcttttt atccatttac tattaacttc tcgtatatgc | 1560 |
| atattagcat tattaattaa aatatacata tgccaaatag tgaattgtaa agaattattt | 1620 |
| catgaatatc caataatttt tttaatttct taaaattagt gggactcagc aaccctaccc | 1680 |
| aagtgatagc tttaattttg taggcacacc atccaaacat gatttctctg attattattg | 1740 |
| tttaaagagt gagaattact tacatgggtt aggggtcacc acctcaacat attaaaatga | 1800 |
| tgtgtttggc taataaaaac ttactagttt agtgggtaca ctgcgaaacc cactaatttt | 1860 |
| tttatttaa ataaagccta ccgaattaaa ttggatgagt cccgcggcag cacctatcta | 1920 |
| atcgagtcta atgacaaaat agagtaaaat gaaggattaa tctgaagtct gctttactgt | 1980 |
| ttcggctata agtaaaggag tagtgaccaa gactctccag tgaatgccac agacaa | 2036 |

<210> SEQ ID NO 4
<211> LENGTH: 1278
<212> TYPE: DNA
<213> ORGANISM: Citrus sinensis

<400> SEQUENCE: 4

| | |
|---|---|
| aatgatttgc agatgcacta aacatggct aattgttata aagggcataa atccaccgat | 60 |
| cacgtgatac cttgtacttt tatgaaatat tcattaattt ttttttcttta taatgtctat | 120 |
| ctgaaattta taagtatat cacttttta cctttcatt aacatcctta aaagatttaa | 180 |
| cataatattc acaaaatttt tcttctggat gtaaaaagga tatttaatct tctttaaacg | 240 |
| ataaaaaga tttcatcttg cagttgttgg gattaataat aattacaaaa ctatctataa | 300 |
| aaactcatca aattacgtat ataaaatcat aaaattacca aagaagcac tgtaactaat | 360 |
| ttgtagctta tttacaacat aaatcaagaa ctcatgctca tataattcat cttaaatgac | 420 |
| acgtctttgt caacagtaac aaactttaac agaaataaat aaaaatgatc atagttatct | 480 |
| aaaatgcatt cgaataatc ataaaatcat ttatgagaaa tcttgaacat tatactttac | 540 |
| ttccataaaa aaaaaaataa tagtataaaa ctagttaaga taatcttgga gtttacagct | 600 |
| tattcccatc aatccaaaat aataatacat tctcgaagca ttgaaaataa taatcaatga | 660 |

```
atactcttttt tatatttagg gataaaataa ttatttttta acatgttgtt aaccctctaa      720
tggtgctaat taaaaaaata aaaactaata aattttataa acttcacata aaaagctgta      780
aaataaaaaa tatttaatat aatttttataa aatataaagt attagatgat agtataaaag     840
cagtaaatat aatggagtta cttcactgta aattacaaat ttaatattta tttctataat     900
tatacagtcg ttaataatgc tgcatcgtaa aacagttata acatgattag attccagtat     960
gaaatatcgt ctatgtggct ccaatagagt aatgacagcc acccttccgg agaaaaaggc    1020
agagagcgga cgattcgaat ctggacatct tgttggcgac tggagtgggg aacgtgtaac    1080
aatgtcatca actcgtcaaa ccaaactttc attaaatcaa ttaattacat ggtagttttg    1140
atgccttaaa gtctttgtgg taagtaggaa ctacctacca actcttcccc catattttat    1200
aagaagaata agaacagcat gcgccagtgt tgctcttctt acttctgctt aaaatctgaa    1260
agaatgaaat agaaaaaa                                                  1278
```

<210> SEQ ID NO 5
<211> LENGTH: 1595
<212> TYPE: DNA
<213> ORGANISM: Prunus armeniaca

<400> SEQUENCE: 5

```
ccaagcttga tttccacct aattgcacat cgatccaaac gctatccctc tatccctcca       60
attaaattat gtagcttcct cttgttcttc acgggctaaa attctatgtt tgctatagtg     120
tagtttccac caatgccccg tttaaactac aaatcaatcg gtcgtgtttg agcttttga     180 atattatctt tttacttcat gtaaattatt gttttcctct ttcaacttaa tcatatatcg    240
tccaatatta ttcttgttga agttttgtcc ctttttttaa ctctaaagct gaattcctat    300
aaaggcttgt agtttaagtg gttaagaaca cttactcata cacaagtcct tgcttcgatt    360
ccccctctcc caatatttac gttaacattc caccaacttt agctcaagta agtattacaa    420
taatttgagg aaacaatgtt taggtgtttt agtttagtgg tttggtactt caattgtcac    480
gcgaatcttt gttttcattt tcgtaaacca gacacaacaa attacaaact aacacttcaa    540
aagtaaggca gactgttggg aacatgcaga cgaaaaatca aaagcaggat tccaggtggg    600
taatgtgttt tgactattag acaatttttat gccagttgaa aactgactttt tctgcgcatg    660 tggaaattgc acatatatat atgagtggac atcatcatct gcagacaaat ccagatcctg    720
tttcatcatt agcttagcta aagtggaata gtatgaagat tacagcctag tagttggtgg    780
aggcacgaaa gattacagct acgcatggga agtctcggtt aatgggatgc cgggtcccct    840
ttgagtgtag aaaagctgct gctcgacaaa taggataccca gcggagtcta acatcctacg    900
aataaaccgt taacgcagca gcgcatatat atatgagtta ggttgcctat gagttattta    960
cactaaggtt ttctactttt tcacaaaatt ctttaaggtt ttagaaatta cacaaacacc    1020
ccctgaggtt ttaaattgtt ttcacaaaat tcattttcat tgattttca accaaagatt    1080 gatggatttt atacaaaaaa aattctccaa atgacaaagt tgacctttga gattggattg    1140
tagatacttt attgaggtta attttctcat ttgcataagt gttttttca atgaaatcat    1200 caattttttgg acaaacaatc aacgaaaaag ggatttgtga aaataaactt aaatctcagg    1260
gggtgttcgt gtaatgtttg agacatgatg gaagttttgt gaaaacacaa gaaacctcag    1320
agggtgttag tgtaaataga aatatattta ataagtttgac tggtagctaa tttatgacag    1380
aattaataac tgttgcaatc ttttaaactt cgtcactttt tgcttatgtg gatatgaggc    1440
```

```
atgcacgtca ctggcctggt aaggtttaat ttgatggtct ccatgcggtc ggagacccTT    1500
tatttataat gctaggtggc ttctggacgc ttaactaaca ggcacaaaat aagctggctg    1560
caagcataca acgctgccca aaagaaaacg gcgcg                               1595
```

```
<210> SEQ ID NO 6
<211> LENGTH: 46
<212> TYPE: DNA
<213> ORGANISM: Artificial Sequence
<220> FEATURE:
<223> OTHER INFORMATION: Synthetic Construct

<400> SEQUENCE: 6
ttttggtacc cctgcagggc catgggagaa ggtgcacata ctttag                   46
```

```
<210> SEQ ID NO 7
<211> LENGTH: 46
<212> TYPE: DNA
<213> ORGANISM: Artificial Sequence
<220> FEATURE:
<223> OTHER INFORMATION: Synthetic Construct

<400> SEQUENCE: 7
ttttcccggg atcgattttc ttctcctttc tttcttcttc tatcac                   46
```

```
<210> SEQ ID NO 8
<211> LENGTH: 33
<212> TYPE: DNA
<213> ORGANISM: Artificial Sequence
<220> FEATURE:
<223> OTHER INFORMATION: Synthetic Construct

<400> SEQUENCE: 8
ttttatcgat ctccaataga ggaaagctgt acg                                 33
```

```
<210> SEQ ID NO 9
<211> LENGTH: 41
<212> TYPE: DNA
<213> ORGANISM: Artificial Sequence
<220> FEATURE:
<223> OTHER INFORMATION: Synthetic Construct

<400> SEQUENCE: 9
ttttgcggcc gcgtttaaac gttgcacttc tggtacctct c                        41
```

```
<210> SEQ ID NO 10
<211> LENGTH: 43
<212> TYPE: DNA
<213> ORGANISM: Artificial Sequence
<220> FEATURE:
<223> OTHER INFORMATION: Synthetic Construct

<400> SEQUENCE: 10
tttccatggt gcactttgag gtaatgcaac atgcaattgc tag                      43
```

```
<210> SEQ ID NO 11
<211> LENGTH: 42
<212> TYPE: DNA
<213> ORGANISM: Artificial Sequence
<220> FEATURE:
<223> OTHER INFORMATION: Synthetic Construct

<400> SEQUENCE: 11
tttgaattcg agaggaagag aacaacaaat taataaaggc gg                       42
```

<210> SEQ ID NO 12
<211> LENGTH: 36
<212> TYPE: DNA
<213> ORGANISM: Artificial Sequence
<220> FEATURE:
<223> OTHER INFORMATION: Synthetic Construct

<400> SEQUENCE: 12
aaaagaattc cctcaatctg caccactaag acgaat                          36

<210> SEQ ID NO 13
<211> LENGTH: 34
<212> TYPE: DNA
<213> ORGANISM: Artificial Sequence
<220> FEATURE:
<223> OTHER INFORMATION: Synthetic Construct

<400> SEQUENCE: 13
aaaaccatgg ttgtctgtgg cattcactgg agag                            34

<210> SEQ ID NO 14
<211> LENGTH: 42
<212> TYPE: DNA
<213> ORGANISM: Artificial Sequence
<220> FEATURE:
<223> OTHER INFORMATION: Synthetic Construct

<400> SEQUENCE: 14
tttgaattcg agaggaagag aacaacaaat taataaaggc gg                   42

<210> SEQ ID NO 15
<211> LENGTH: 41
<212> TYPE: DNA
<213> ORGANISM: Artificial Sequence
<220> FEATURE:
<223> OTHER INFORMATION: Synthetic Construct

<400> SEQUENCE: 15
tttccatggt tttttctatt tcattctttc agattttaag c                    41

<210> SEQ ID NO 16
<211> LENGTH: 45
<212> TYPE: DNA
<213> ORGANISM: Artificial Sequence
<220> FEATURE:
<223> OTHER INFORMATION: Synthetic Construct

<400> SEQUENCE: 16
agtccctgca gggattttcc acctaattgc acatcgatcc aaacg                45

<210> SEQ ID NO 17
<211> LENGTH: 42
<212> TYPE: DNA
<213> ORGANISM: Artificial Sequence
<220> FEATURE:
<223> OTHER INFORMATION: Synthetic Construct

<400> SEQUENCE: 17
agtcccatgg ttttcttttg ggcagcgttg tatgcttgca gc                   42

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
cgctcaggtg atataagagg                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
tgaatagggc ttcgtcaatc                                          20

<210> SEQ ID NO 20
<211> LENGTH: 24
<212> TYPE: DNA
<213> ORGANISM: Artificial Sequence
<220> FEATURE:
<223> OTHER INFORMATION: Synthetic Construct

<400> SEQUENCE: 20
aaggatgtac actagacttg cggc                                     24

<210> SEQ ID NO 21
<211> LENGTH: 180
<212> TYPE: DNA
<213> ORGANISM: Agrobacterium tumefaciens

<400> SEQUENCE: 21
gaaccgcaac gttgaaggag ccactgagcc gcgggtttct ggagtttaat gagctaagca      60
catacgtcag aaaccattat tgcgcgttca aaagtcgcct aaggtcacta tcagctagca     120
aatatttctt gtcaaaaatg ctccactgac gttccataaa ttcccctcgg tatccaatta    180

<210> SEQ ID NO 22
<211> LENGTH: 528
<212> TYPE: DNA
<213> ORGANISM: Arabidopsis thaliana

<400> SEQUENCE: 22
atgtctataa atataagaga ccctcttata gtaagcagag ttgttggaga cgttcttgat      60
ccgtttaata gatcaatcac tctaaaggtt acttatggcc aaagagaggt gactaatggc     120
ttggatctaa ggccttctca ggttcaaaac aagccaagag ttgagattgg tggagaagac     180
ctcaggaact tctatacttt ggttatggtt gatccagatg ttccaagtcc tagcaaccct     240
cacctccgag aatatctcca ttggttggtg actgatatcc ctgctacaac tggaacaacc     300
tttggcaatg agattgtgtg ttacgaaaat ccaagtccca ctgcaggtat tcatcgtgtc     360
gtgtttatat tgtttcgaca gcttggcagg caaacagtgt atgcaccagg gtggcgccag     420
aacttcaaca ctcgcgagtt tgctgaaatc tacaatctcg gccttcccgt ggccgcagtt     480
ttctataatt gtcagaggga gagtggctgc ggaggaagaa gactttag                  528

<210> SEQ ID NO 23
<211> LENGTH: 252
<212> TYPE: DNA
<213> ORGANISM: Agrobacterium tumefaciens

<400> SEQUENCE: 23
gatcgttcaa acatttggca ataaagtttc ttaagattga atcctgttgc cggtcttgcg      60
atgattatca tataatttct gttgaattac gttaagcatg taataattaa catgtaatgc     120

```
atgacgttat ttatgagatg ggttttttga ttagagtccc gcaattatac atttaatacg    180
cgatagaaaa caaaatatag cgcgcaaact aggataaatt atcgcgcgcg gtgtcatcta    240
tgttactaga tc                                                        252
```

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24

```
ttgccgaata tcatggtgga                                                 20
```

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25

```
tcagcaatat cacgggtagc                                                 20
```

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26

```
tgcaacatcc ttctttcttc tcgtg                                           25
```

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27

```
gcaatatcaa gagccccgtc                                                 20
```

<210> SEQ ID NO 28
<211> LENGTH: 18
<212> TYPE: DNA
<213> ORGANISM: Artificial Sequence
<220> FEATURE:
<223> OTHER INFORMATION: Synthetic Construct

<400> SEQUENCE: 28

```
atgtgtgcta agcgctcc                                                   18
```

<210> SEQ ID NO 29
<211> LENGTH: 18
<212> TYPE: DNA
<213> ORGANISM: Artificial Sequence
<220> FEATURE:
<223> OTHER INFORMATION: Synthetic Construct

<400> SEQUENCE: 29

```
cgggcagatt aacgatgg                                                   18
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
cgcatcaaac ccattttcag                                              20

<210> SEQ ID NO 31
<211> LENGTH: 12
<212> TYPE: DNA
<213> ORGANISM: Artificial Sequence
<220> FEATURE:
<223> OTHER INFORMATION: Synthetic Construct

<400> SEQUENCE: 31
cggcaggata at                                                      12
```